(12) United States Patent
Xu et al.

(10) Patent No.: US 10,676,474 B2
(45) Date of Patent: Jun. 9, 2020

(54) 1,6-NAPHTHYRIDINE DERIVATIVES AS CDK4/6 INHIBITOR

(71) Applicants: CSTONE PHARMACEUTICALS, Grand Cayman (KY); MEDSHINE DISCOVERY INC., Nanjing, Jiangsu (CN)

(72) Inventors: Zhaobing Xu, Shanghai (CN); Lihong Hu, Shanghai (CN); Charles Z. Ding, Shanghai (CN); Shuhui Chen, Shanghai (CN)

(73) Assignees: CSTONE PHARMACEUTICALS, Grand Cayman (KY); MEDSHINE DISCOVERY INC., Nanjing, Jiangsu (CN)

( * ) Notice: Subject to any disclaimer, the term of this patent is extended or adjusted under 35 U.S.C. 154(b) by 0 days.

(21) Appl. No.: 16/470,111

(22) PCT Filed: Dec. 15, 2017

(86) PCT No.: PCT/CN2017/116611
§ 371 (c)(1),
(2) Date: Jun. 14, 2019

(87) PCT Pub. No.: WO2018/108167
PCT Pub. Date: Jun. 21, 2018

(65) Prior Publication Data
US 2019/0315745 A1    Oct. 17, 2019

(30) Foreign Application Priority Data

Dec. 16, 2016    (CN) .......................... 2016 1 1170508
Sep. 4, 2017    (CN) .......................... 2017 1 0787583

(51) Int. Cl.
*A61K 31/497* (2006.01)
*C07D 241/20* (2006.01)
*C07D 471/04* (2006.01)
*A61P 35/00* (2006.01)
*C07D 519/00* (2006.01)

(52) U.S. Cl.
CPC ............ *C07D 471/04* (2013.01); *A61P 35/00* (2018.01); *C07D 519/00* (2013.01)

(58) Field of Classification Search
CPC .......................... A61K 31/497; C07D 241/20
USPC ...................... 514/255.06; 544/405
See application file for complete search history.

(56) References Cited

FOREIGN PATENT DOCUMENTS

| CN | 104812756 A | 7/2015 |
|---|---|---|
| CN | 105130986 A | 12/2015 |
| CN | 104470921 B | 5/2017 |
| WO | 03062236 A1 | 7/2003 |
| WO | 2005094830 A1 | 10/2005 |
| WO | 2005117980 A1 | 12/2005 |
| WO | 2008032157 A2 | 3/2008 |
| WO | 2009126584 A1 | 10/2009 |
| WO | 2010075074 A1 | 7/2010 |
| WO | 2011101409 A1 | 8/2011 |
| WO | 2011130232 A1 | 10/2011 |
| WO | 2012018540 A1 | 2/2012 |
| WO | 2012129344 A1 | 9/2012 |
| WO | 2014052365 A1 | 4/2014 |
| WO | 2014128588 A1 | 8/2014 |
| WO | 2014183520 A1 | 11/2014 |
| WO | 2017101763 A1 | 6/2017 |
| WO | WO 18/108167 | * 6/2018 |

OTHER PUBLICATIONS

Jordan, V. C. Nature Reviews: Drug Discovery, 2, 2003, 205.*
Hackam, et al. JAMA, 296(14), 2006, 1731-1732.*
Berge, et al., "Pharmaceutical Salts", Journal of Pharmaceutical Science 66: 1-19 (1977).
Remington: The Science and Practice of Pharmacy, 21st Ed., Lippincott, Williams & Wilkins (2005).
International Search Report and Written Opinion of PCT/CN2017/116611 dated Feb. 26, 2018.
Extended European Search Report issued in European patent application No. 17880229.4 dated Aug. 8, 2019.
English translation of Chinese priority application No. 201611170508.1.
English translation of Chinese priority application No. 201710787583.0.

* cited by examiner

*Primary Examiner* — Douglas M Willis
(74) *Attorney, Agent, or Firm* — Harness, Dickey & Pierce, P.L.C.

(57) ABSTRACT

Disclosed is a series of compounds acting as CDK4/6 inhibitors. Specifically disclosed are compounds as represented by formula (I), pharmaceutically acceptable salts or isomers thereof, pharmaceutical compositions containing same, and the use thereof in the preparation of drugs for treating cancers.

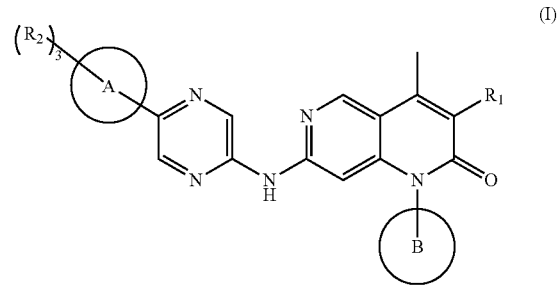

20 Claims, No Drawings

1,6-NAPHTHYRIDINE DERIVATIVES AS CDK4/6 INHIBITOR

CROSS-REFERENCE TO RELATED APPLICATIONS

This application is a 371 National Phase of PCT/CN2017/116611 filed Dec. 15, 2017, which claims priority to Chinese Patent Application No. CN201611170508.1 filed on Dec. 16, 2016 and Chinese Patent Application No. CN201710787583.0 filed on Sep. 4, 2017. The entire disclosures of the above applications are incorporated herein by reference.

BACKGROUND OF THE INVENTION

Field of the Invention

The present invention relates to a series of compounds as CDK4/6 inhibitors. Specifically disclosed a compound as represented by formula (I), a pharmaceutically acceptable salt thereof or an isomer thereof, a pharmaceutical composition comprising the same, and a use thereof in manufacturing a medicament for treating cancers.

Description of Related Art

The cell cycle refers to the continuous dynamic process that normal continuous dividing cells undergo from the end of the previous mitosis to the end of the next mitosis. The mammalian cell cycle consists of four phases: G1 phase (pre-DNA synthesis phase), S phase (DNA synthesis phase), G2 phase (post-DNA synthesis phase), and M phase (mitosis phase). Cytokinesis begins immediately after the M phase, forming two daughter cells. Although the nascent cells produced by cell cycle division re-enter the cell cycle, at some point in the late G1 (called the restriction point or R point), the cell cycle regulation mechanism determines the final fate of the cells: continue to participate in the cell cycle or withdraw from the active proliferative state to a static state (G0). The regulation of the cell cycle is mainly influenced by a series of serine/threonine kinases. The series of serine/threonine kinases are also called cyclin-dependent kinases (CDKs), which combine with their corresponding regulatory subunits cyclins to achieve the purpose of regulating the cell cycle. So far, at least 10 cyclin-dependent kinases (CDKs) and 15 cyclins have been identified, which can form pairing complexes as follows: CDK1 paired with cyclin A or B; CDK2 paired with cyclin A or E; CDK3 paired with an unknown cyclin; CDK4 paired with cyclin D (1-3); CDKS paired with Cyclin D or p35Nck5A; CDK6 paired with cyclin D; CDK7 paired with cyclin H; CDK8 paired with cyclin C; CDK9 paired with cyclin T.

Abnormal proliferation of cancer cells and dysregulation of normal cell cycle are common characteristics of all types of cancer. Therefore, the inhibitors of the key cell cycle regulators have become an attractive novel anti-tumor target. In the early G1 phase of the cell cycle, a complex of CDK4/6 and cyclin D is activated by extracellular growth factors. The retinoblastoma protein (RB) is phosphorylated by the activated complex, thereby releasing the transcription factor E2F which is tightly bound to the complex in the unphosphorylated state. E2F activates the further transcription and promotes the cell cycle beyond the R point and progressing from G1 phase to S phase. Once beyond the point R, other cyclins are activated sequentially to regulate the whole cell cycle. For example, binding of CDK2 to cyclin E controls cells entering S phase; binding of CDK2 to cyclin A controls the process of S phase, and then CDK1 binds cyclin A in the G2 phase; finally, binding of CDK1 to cyclin B controls cells entering the mitosis phase. The complex formed by CDK4/6 and cyclin D is a key "master switch" in cell cycle regulation, inhibiting CDK4/6 and preventing the formation of Cyclin D-CDK4/6 complex, it can block the progression of the cell cycle from G1 phase to S phase in order to achieve the purpose of inhibiting the tumor proliferation. Therefore, CDK4/6 has become an important anti-cancer target.

In recent years, several small molecular CDK4/6 inhibitors have entered the clinical trial phase for the treatment of cancer, either alone or in combination. Based on the interim data from Phase II clinical trial PALOMA-1, Palbociclib was approved by FDA for the request of marketing in February 2015 and used in combination with letrozole as a first-line treatment for ER-positive/HER2-negative postmenopausal metastatic breast cancer. Besides, the study of Palbociclib in the treatment of non-small cell lung cancer is also in Phase III clinical trial. In addition, based on the results of the phase III clinical trial MONALEESA-2, the US FDA granted a Breakthrough Therapy designation for the CDK4/6 inhibitor Ribociclib (LEE-011) in August 2016, which can be combined with letrozole for first-line treatment of advanced or metastatic hormones receptor-positive/HER2-negative breast cancer. CDK4/6 inhibitor Abemaciclib (LY2835219) from Eli Lilly & Co. is also in phase III clinical trial MONARCH2, and expected to receive the final clinical trial results of MONARCH2 in the first half of 2017. In addition to being useful in the treatment of breast cancer, these small molecular heterocyclic compounds are clinically useful in the treatment of a variety of other cancers. These patents include WO2014128588, WO2012018540, WO2012129344, WO2011101409, WO2011130232, WO2010075074, WO2009126584, WO2008032157, WO2005094830, WO2005117980 and WO2003062236.

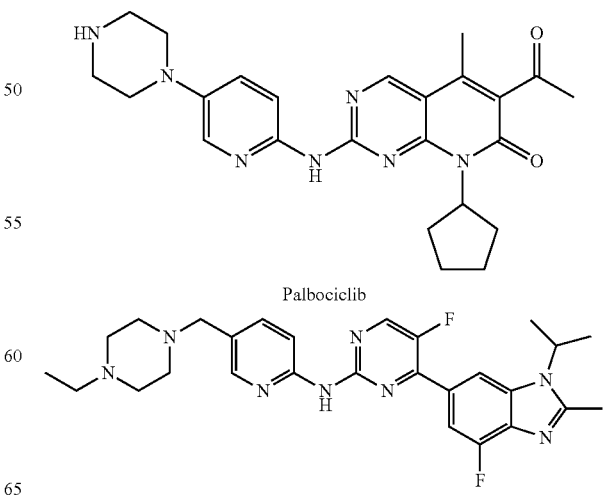

Palbociclib

LY-2835219

-continued

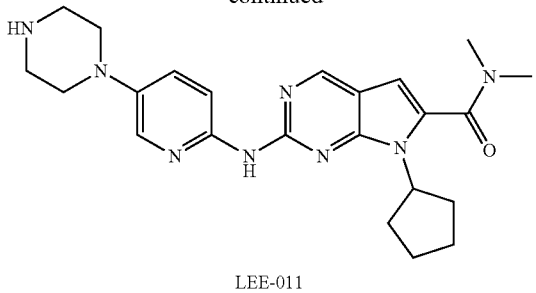

LEE-011

Although many efforts have been made on developing CDK4/6 inhibitors for the treatment of cancer and other diseases, only one drug (Palbociclib) for this target has been launched so far, and the indication is only ER-positive/HER2-negative postmenopausal metastatic breast cancer. Although the clinical studies of lung cancer with CDK4/6 inhibitors have progressed to phase III clinical trials, there are no drugs launched so far. Therefore, there is still an urgent need to develop a novel, safer and more effective CDK4/6 inhibitor that can treat a variety of cancers, including lung cancer. On the other hand, although Palbociclib has been approved for marketing, it has been reported that the brain permeability thereof is poor, which makes it difficult to penetrate the blood-brain barrier and unable to treat the brain metastasis.

BRIEF SUMMARY OF THE INVENTION

In one aspect, the present invention provides a compound of formula (I), a pharmaceutically acceptable salt thereof or an isomer thereof,

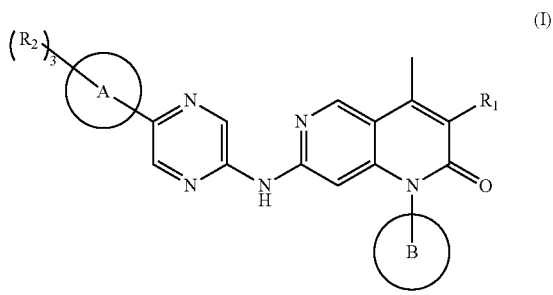

wherein, $R_1$ is H, or selected from the group consisting of $C_{1-3}$ alkyl, $C_{1-3}$ heteroalkyl,

each of which is optionally substituted by 1, 2 or 3 R;

each of $R_2$ is independently H, OH, CN, halogen, or selected from the group consisting of $C_{1-5}$ alkyl, $C_{1-5}$ heteroalkyl, $C_{3-6}$ cycloalkyl and 3-6 membered heterocycloalkyl, each of which is optionally substituted by 1, 2 or 3 R;

ring A is 4-11 membered heterocycloalkyl;

ring B is selected from the group consisting of $C_{3-6}$ cycloalkyl, 3-6 membered heterocycloalkyl, phenyl and 5-6 membered heteroaryl, each of which is optionally substituted by 1, 2 or 3 R;

R is halogen, OH, CN, $NH_2$, $NO_2$, or selected from the group consisting of $C_{1-3}$ alkyl and $C_{1-3}$ heteroalkyl, each of which is optionally substituted by 1, 2 or 3 R';

R' is selected from the group consisting of F, Cl, Br, I, OH, CN and $NH_2$;

each of the "hetero" in the $C_{1-3}$ heteroalkyl, $C_{1-5}$ heteroalkyl, 3-6 membered heterocycloalkyl, 4-11 membered heterocycloalkyl and 5-6 membered heteroaryl is independently selected from the group consisting of N, —O—, —S—, —NH—, —(C=O)—, —(S=O)— and —(S=O)$_2$—;

in any of the above cases, the number of the heteroatom or the heteroatomic group is independently 1, 2 or 3.

In some embodiments of the present invention, the above R is selected from F, Cl, Br, OH, CN, $NH_2$, $CH_3$, $CH_3CH_2$, $CH_3O$, $CF_3$, $CHF_2$, $CH_2F$, and other variables are as defined in the present invention.

In some embodiments of the present invention, the above $R_1$ is H, or selected from the group consisting of $CH_3$, $CH_3CH_2$, $CH_3(C=O)$—,

each of which is optionally substituted by 1, 2 or 3 R, and R and other variables are as defined in the present invention.

In some embodiments of the present invention, the above $R_1$ is selected from $CH_3$, $CHF_2$, $CH_3(C=O)$—,

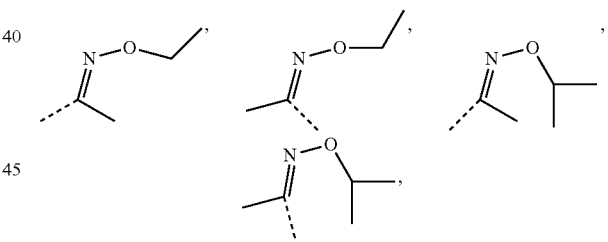

and other variables are as defined in the present invention.

In some embodiments of the present invention, the above ring B is selected from the group consisting of cyclobutyl, cyclopentyl, cyclohexyl and phenyl, each of which is optionally substituted by 1, 2 or 3 R, and R and other variables are as defined in the present invention.

In some embodiments of the present invention, the above ring B is selected from cyclopentyl, cyclohexyl, phenyl, and other variables are as defined in the present invention.

In some embodiments of the present invention, each of the above $R_2$ is independently selected from H, OH, CN, F, Cl, or selected from the group consisting of $CH_3$,

oxetanyl, piperazinyl and morpholinyl, each of which is optionally substituted by 1, 2 or 3 R, and R and other variables are as defined in the present invention.

In some embodiments of the present invention, each of the above $R_2$ is independently H or selected from the group consisting of $CH_3$,

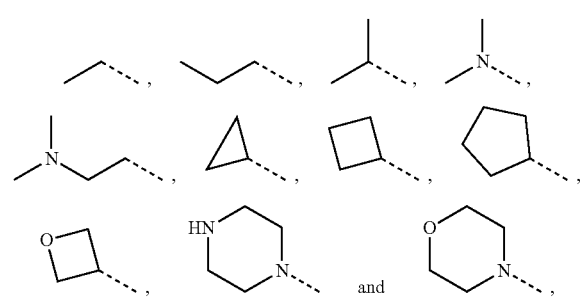

each of which is optionally substituted by 1, 2 or 3 R, and R and other variables are as defined in the present invention.

In some embodiments of the present invention, each of the above $R_2$ is independently selected from the group consisting of H, $CH_3$,

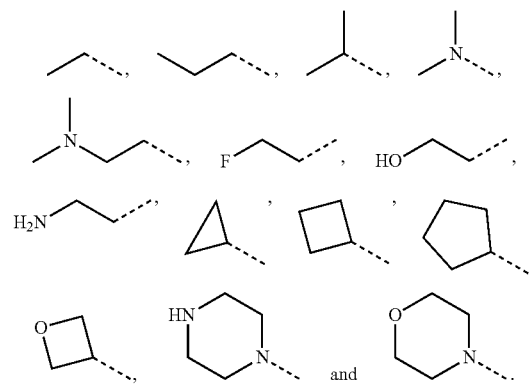

and other variables are as defined in the present invention.

In some embodiments of the present invention, the above ring A is 5-9 membered heterocycloalkyl, and other variables are as defined in the present invention.

In some embodiments of the present invention, the above moiety

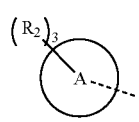

is selected from the group consisting of

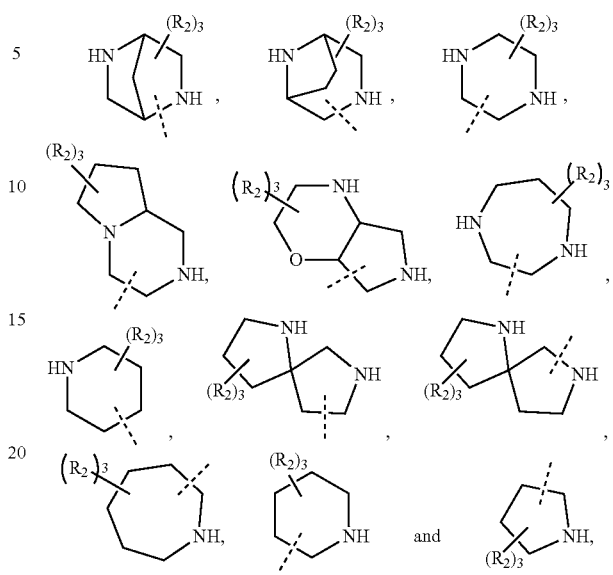

and $R_2$ and other variables are as defined in the present invention.

In some embodiments of the present invention, the above moiety

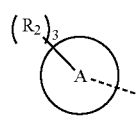

is selected from the group consisting of

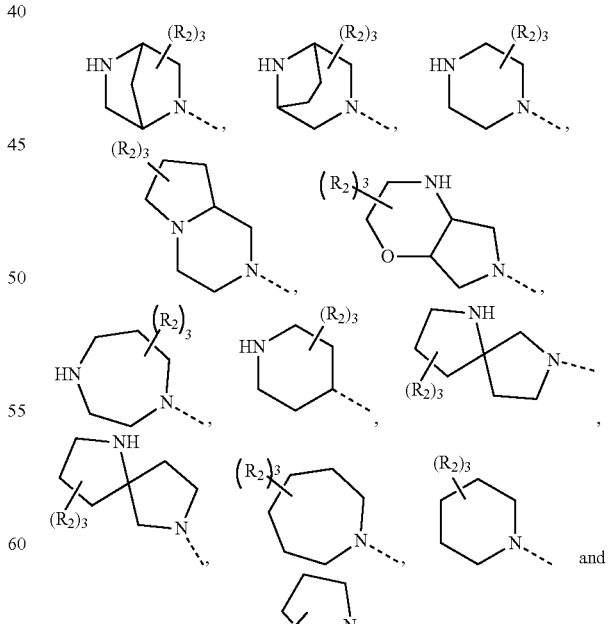

and $R_2$ and other variables are as defined in the present invention.

In some embodiments of the present invention, the above moiety
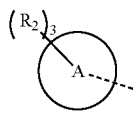
is selected from the group consisting of
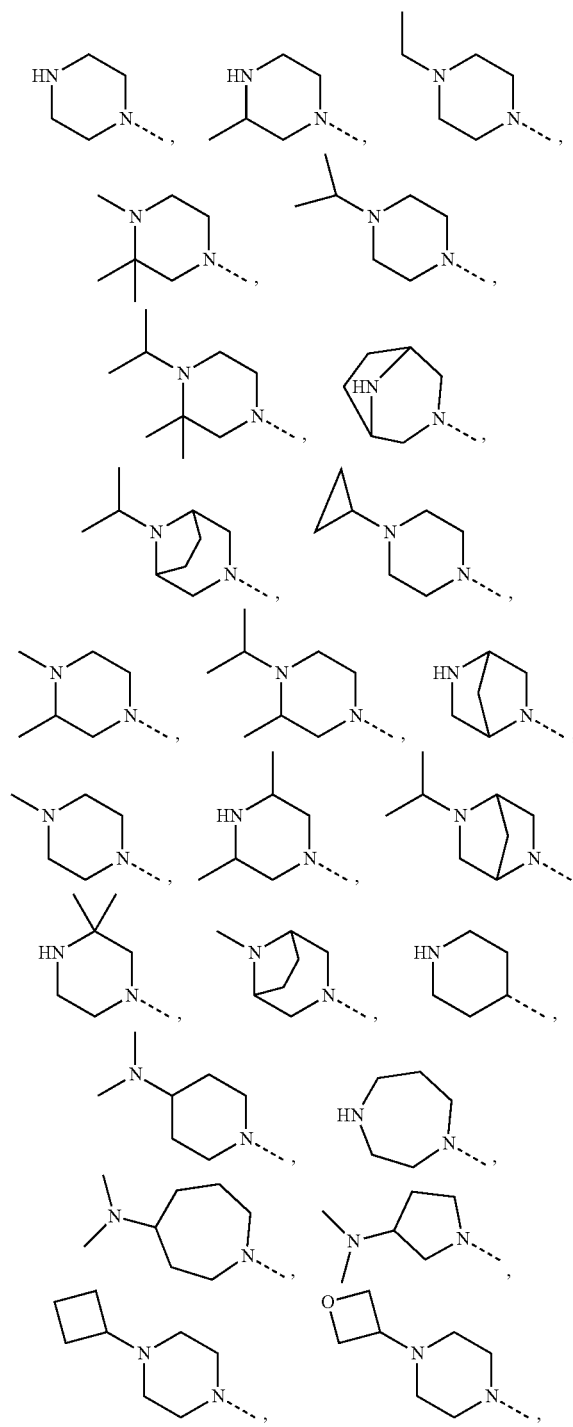
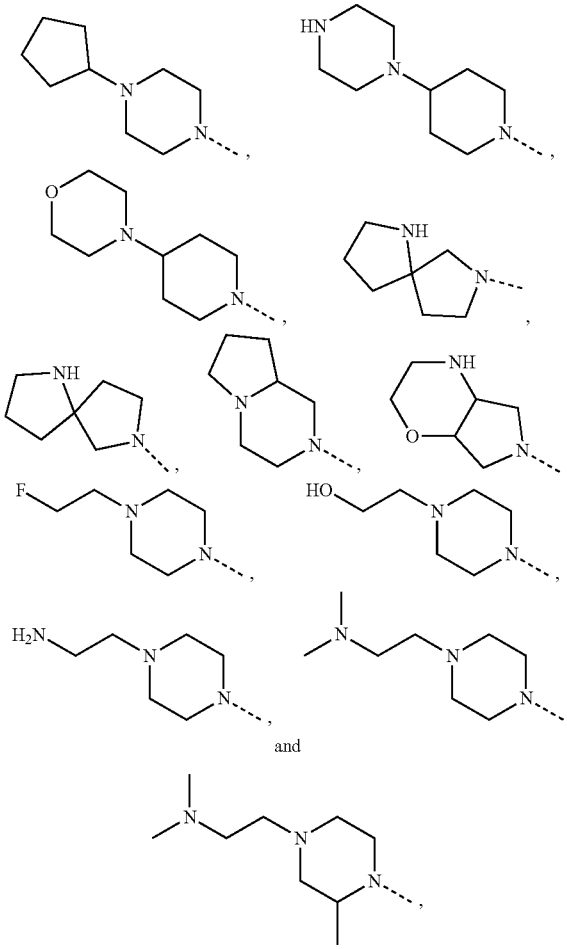
and other variables are as defined in the present invention.
In some embodiments of the present invention, the above compound, the pharmaceutically acceptable salt thereof or the isomer thereof is selected from the group consisting of
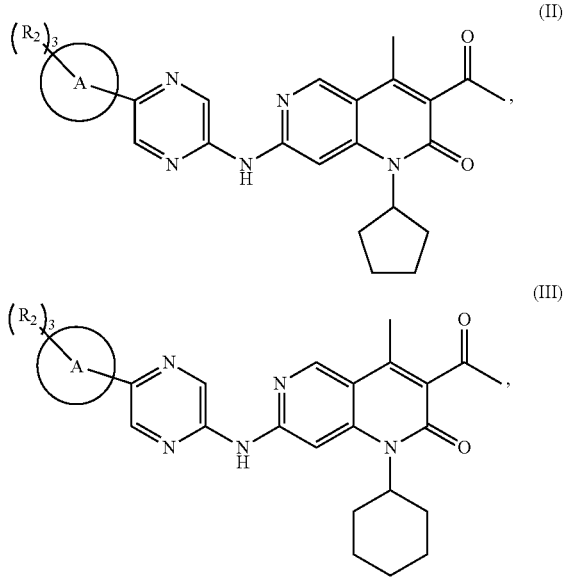

-continued

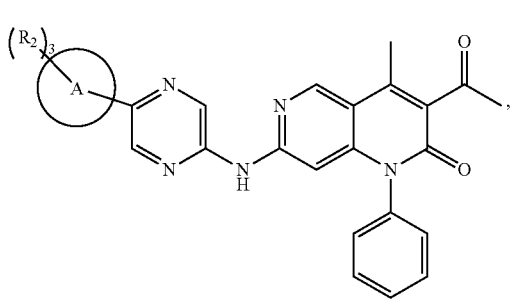
(IV)

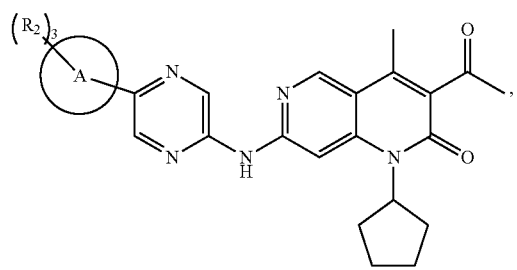
(V)

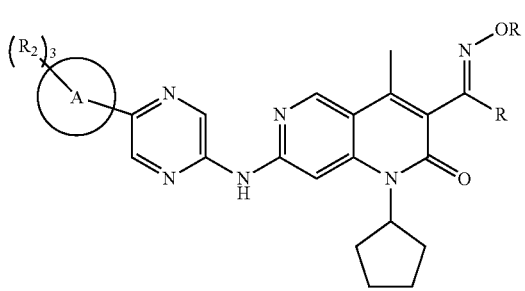
(VI)

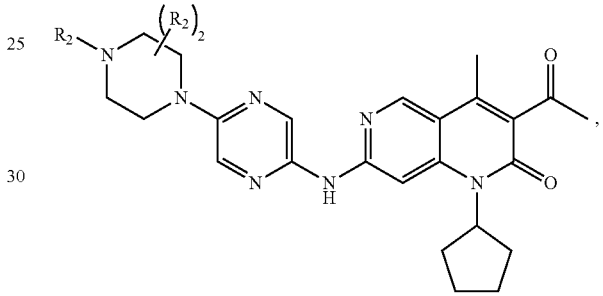
(VI')

wherein, R₂, R and ring A are as defined in the present invention.

In some embodiments of the present invention, the above compound, the pharmaceutically acceptable salt thereof or the isomer thereof is

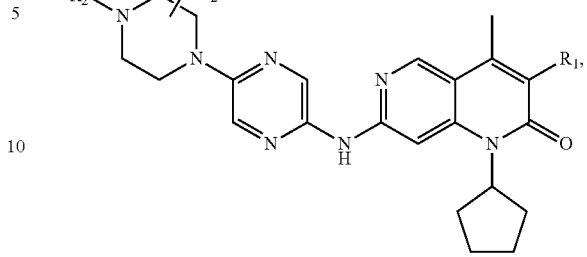
(VII)

wherein, R₁ and R₂ are as defined in the present invention.

In some embodiments of the present invention, the above compound, the pharmaceutically acceptable salt thereof or the isomer thereof is (VIII)

wherein, R₂ is as defined in the present invention.

In some embodiments of the present invention, R₁ is H, or selected from the group consisting of $C_{1-3}$ alkyl and $C_{1-3}$ heteroalkyl, each of which is optionally substituted by 1, 2 or 3 R; each of R₂ is independently selected from H, OH, CN, halogen, or selected from the group consisting of $C_{1-5}$ alkyl, $C_{1-5}$ heteroalkyl, $C_{3-6}$ cycloalkyl and 3-6 membered heterocycloalkyl, each of which is optionally substituted by 1, 2 or 3 R;

ring A is 4-11 membered heterocyclohydrocarbyl;

ring B is selected from the group consisting of $C_{3-6}$ cycloalkyl, 3-6 membered heterocycloalkyl, phenyl and 5-6 membered heteroaryl, each of which is optionally substituted by 1, 2 or 3 R;

R is selected from halogen, OH, CN, NH₂, or selected from the group consisting of $C_{1-3}$ alkyl and $C_{1-3}$ heteroalkyl, each of which is optionally substituted by 1, 2 or 3 R';

R' is selected from the group consisting of F, Cl, Br, I, OH, CN and NH₂;

each of the "hetero" in the $C_{1-3}$ heteroalkyl, $C_{1-5}$ heteroalkyl, 3-6 membered heterocycloalkyl, 4-11 membered heterocyclohydrocarbyl and 5-6 membered heteroaryl is independently selected from the group consisting of N, —O—, =O, —S—, —NH—, —(C=O)—, —(S=O)— and —(S=O)₂—;

in any of the above cases, the number of the heteroatom or the heteroatomic group is independently 1, 2 or 3.

In some embodiments of the present invention, the above R is selected from F, Cl, Br, OH, CN, NH₂, CH₃, CH₃CH₂, CH₃O, CF₃, CHF₂, CH₂F, and other variables are as defined in the present invention.

In some embodiments of the present invention, the above R₁ is H, or selected from the group consisting of CH₃, CH₃CH₂ and CH₃(C=O), each of which is optionally substituted by 1, 2 or 3 R.

In some embodiments of the present invention, the above R₁ is CH₃, CHF₂ or CH₃(C=O), and R and other variables are as defined in the present invention.

In some embodiments of the present invention, the above ring B is selected from the group consisting of cyclobutyl, cyclopentyl, cyclohexyl and phenyl, each of which is optionally substituted by 1, 2 or 3 R, and R and other variables are as defined in the present invention.

In some embodiments of the present invention, the above ring B is cyclopentyl, cyclohexyl or phenyl, and other variables are as defined in the present invention.

In some embodiments of the present invention, the above R₂ is selected from H, OH, CN, F, Cl, or selected from the group consisting of CH₃,

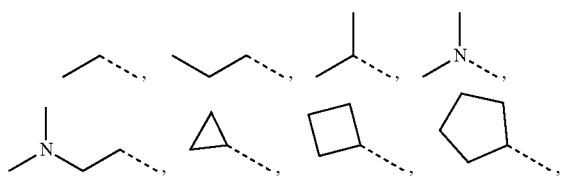

oxetanyl, piperazinyl and morpholinyl, each of which is optionally substituted by 1, 2 or 3 R, and R and other variables are as defined in the present invention.

In some embodiments of the present invention, the above R₂ is H or selected from the group consisting of CH₃,

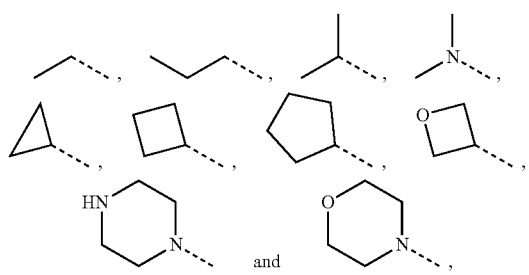

each of which is optionally substituted by 1, 2 or 3 R, and R and other variables are as defined in the present invention.

In some embodiments of the present invention, the above R₂ is selected from the group consisting of H, CH₃,

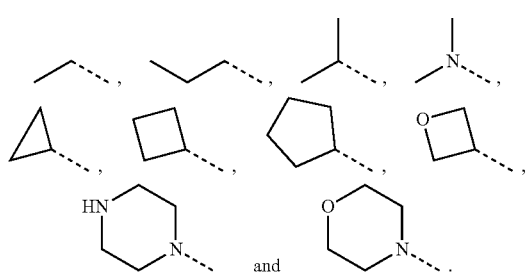

In some embodiments of the present invention, the above ring A is selected from the group consisting of

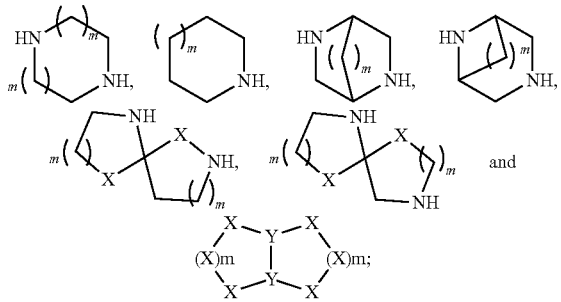

each of m is independently 0, 1 or 2; each of X is independently CH₂, NH or O; each of Y is independently CH or N, and other variables are as defined in the present invention.

In some embodiments of the present invention, the above ring A is selected from the group consisting of

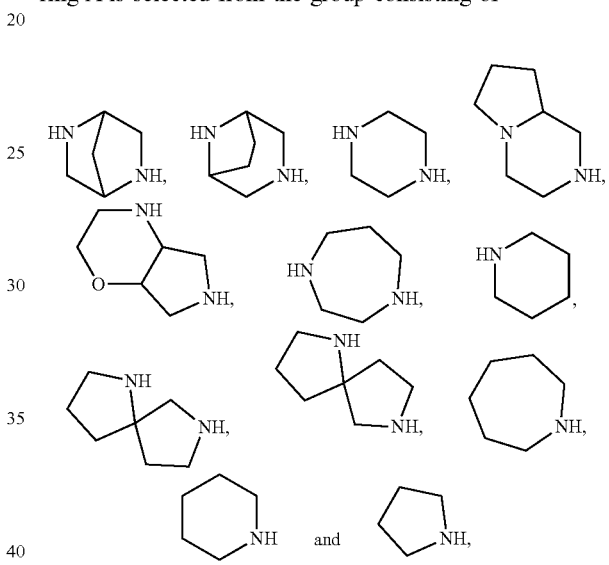

and other variables are as defined in the present invention.

In some embodiments of the present invention, the above moiety

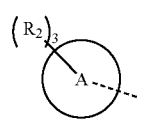

is selected from the group consisting of

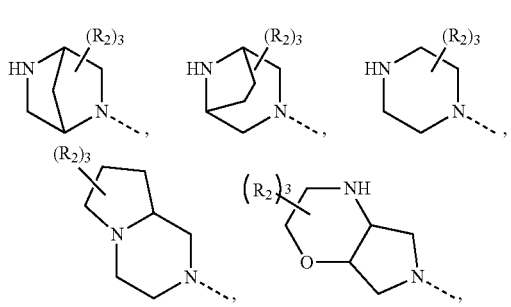

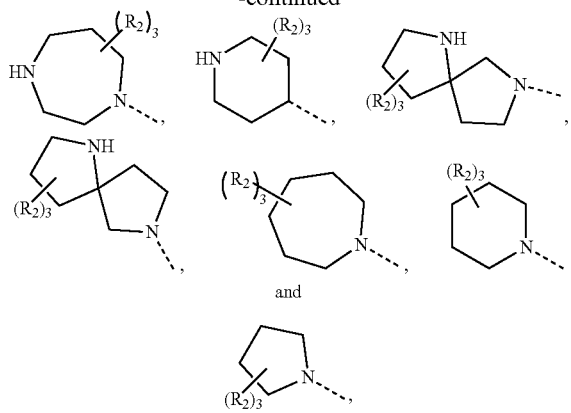
and R$_2$ and other variables are as defined in the present invention.
In some embodiments of the present invention, the above moiety
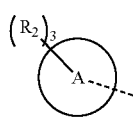
is selected from the group consisting of
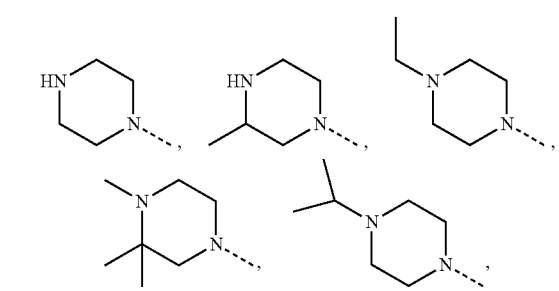
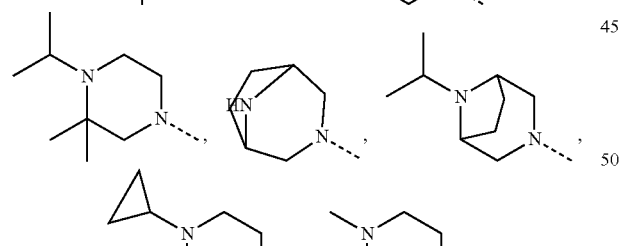
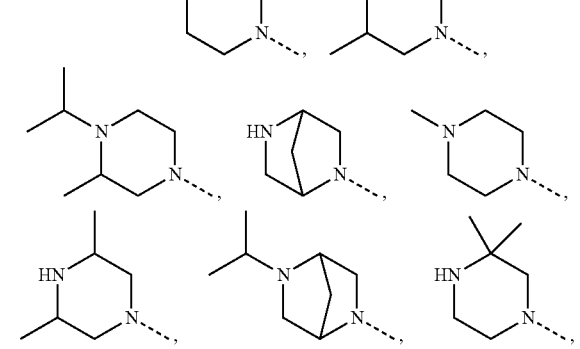
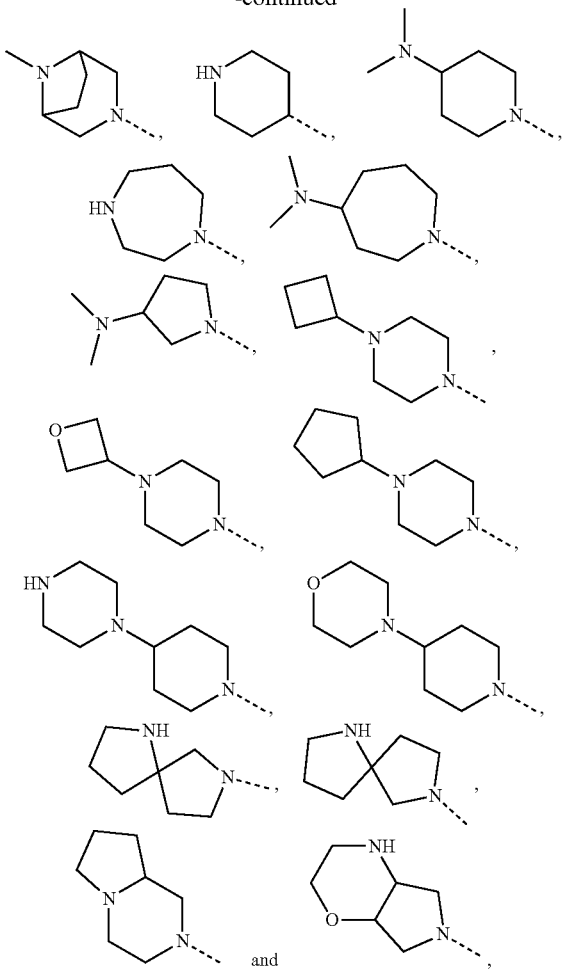
and other variables are as defined in the present invention.
In some embodiments of the present invention, the above compound is selected from the group consisting of
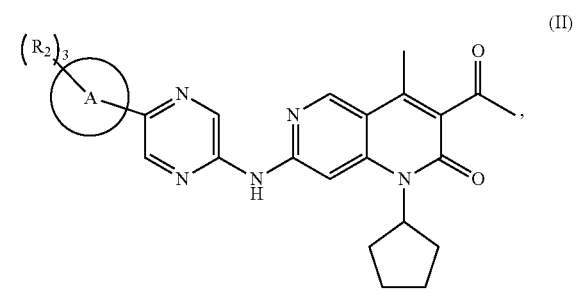
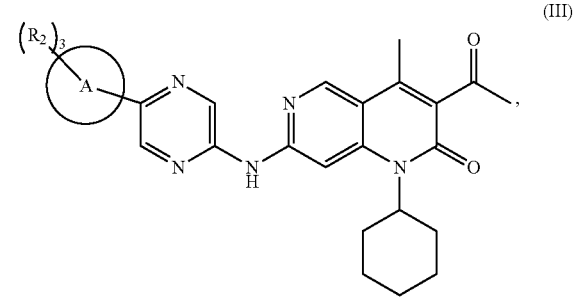

-continued

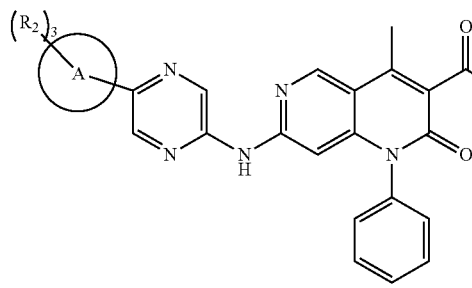
(IV)

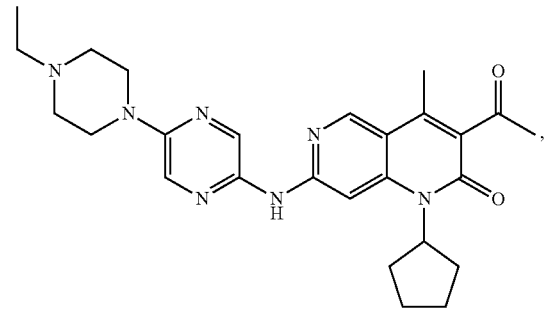

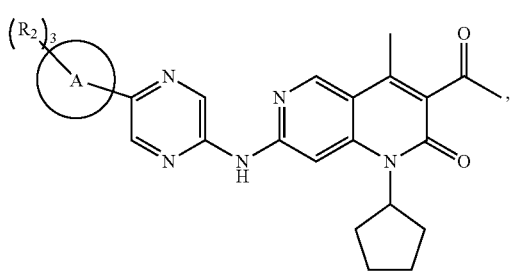
(V)

wherein, R₂ and ring A are as defined in the present invention.

In some embodiments of the present invention, the above compound is selected from

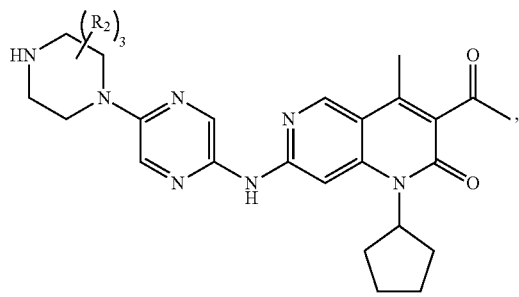
(IX)

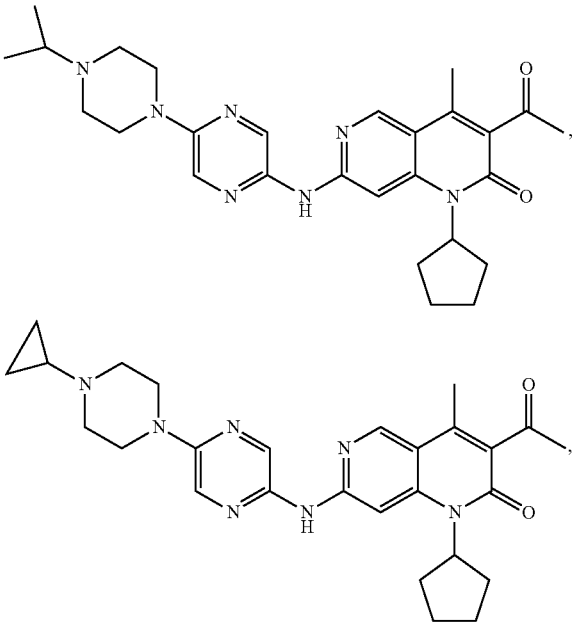

wherein, R₂ is as defined in the present invention.

In some embodiments of the present invention, the above compound, the pharmaceutically acceptable salt thereof or the isomer thereof is selected from the group consisting of

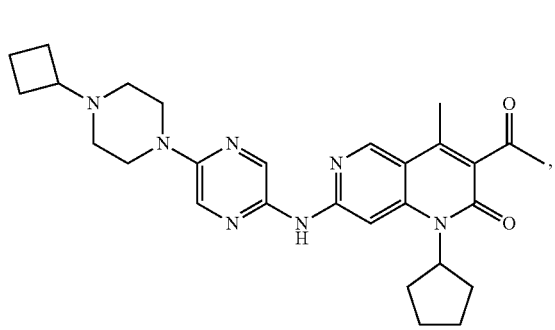

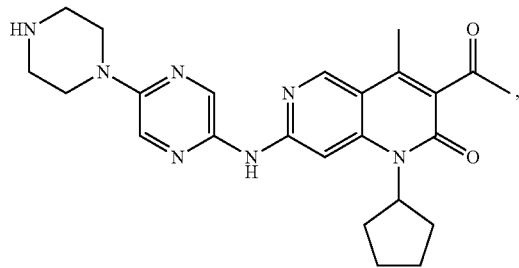

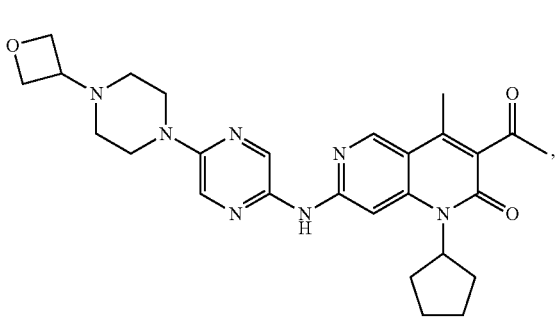

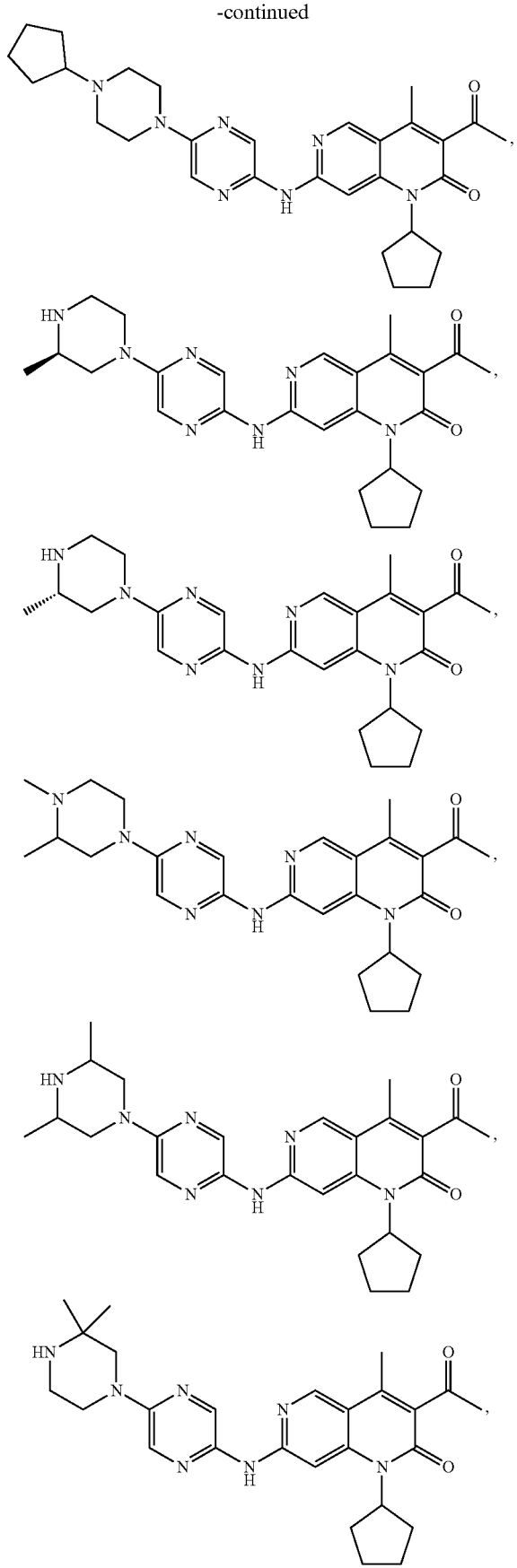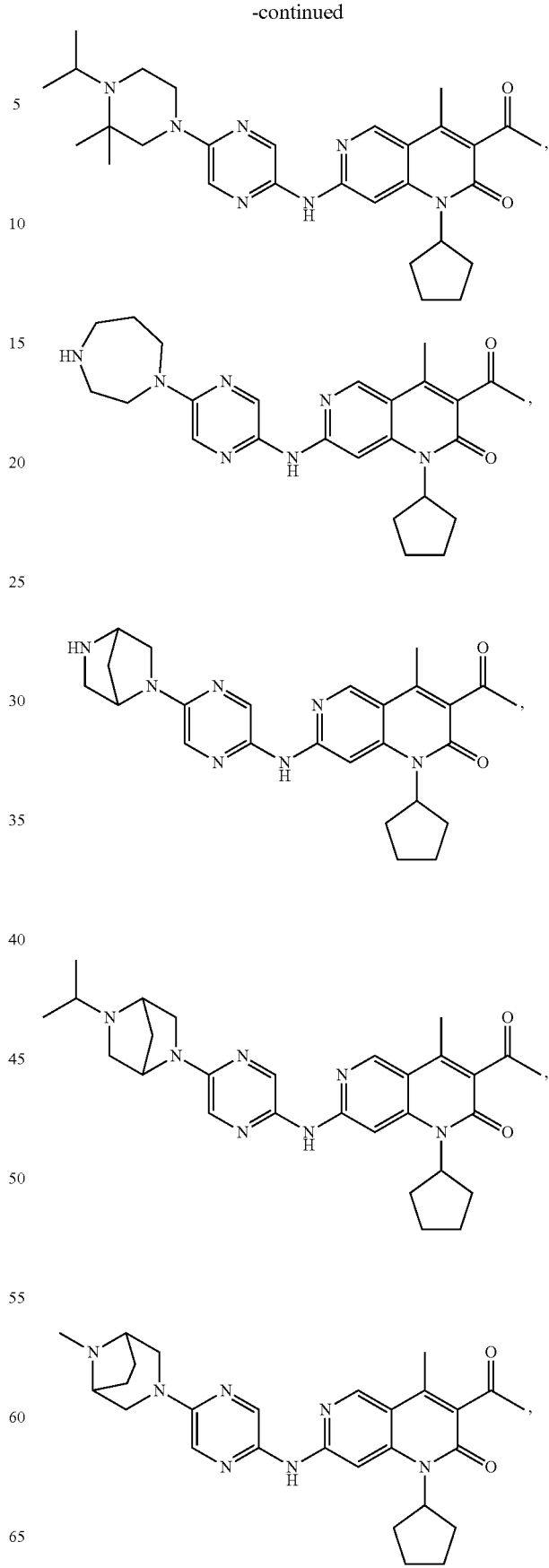

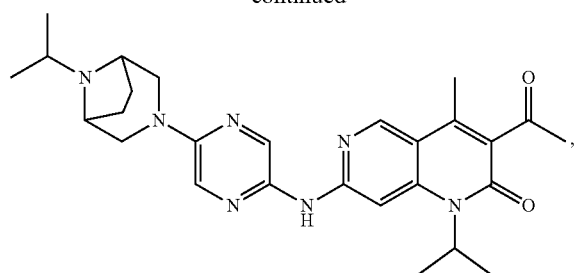
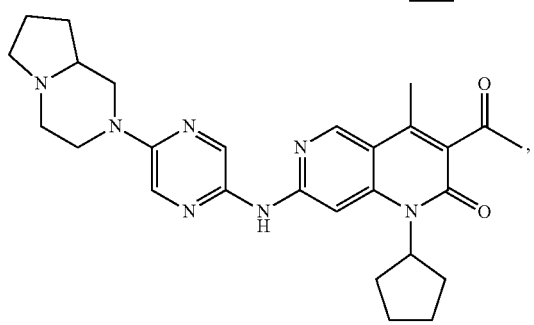
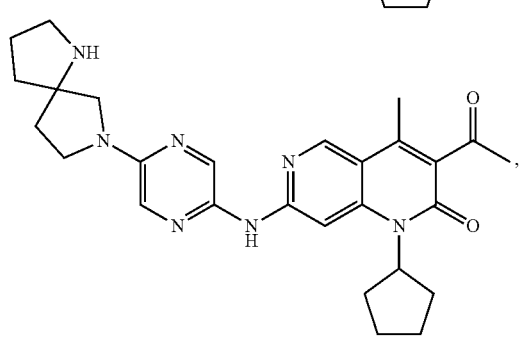
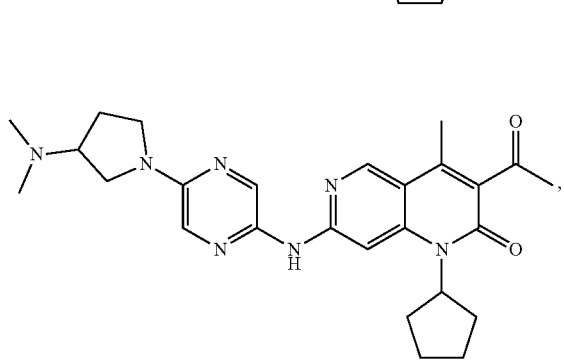
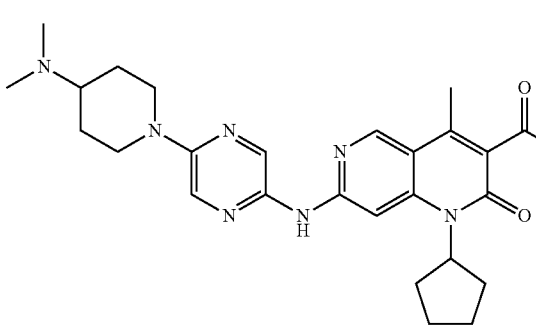
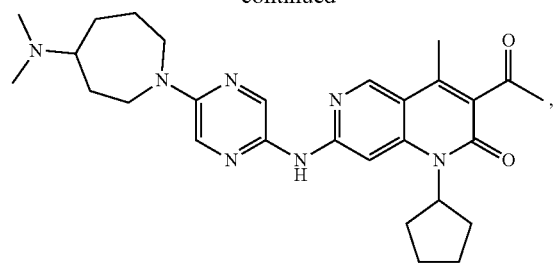
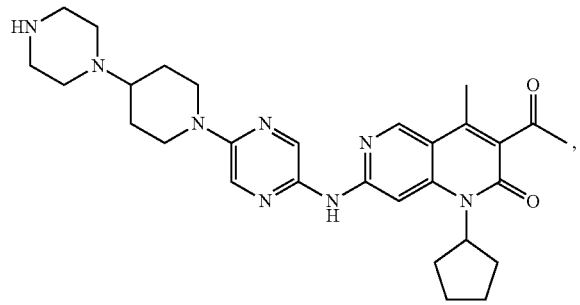
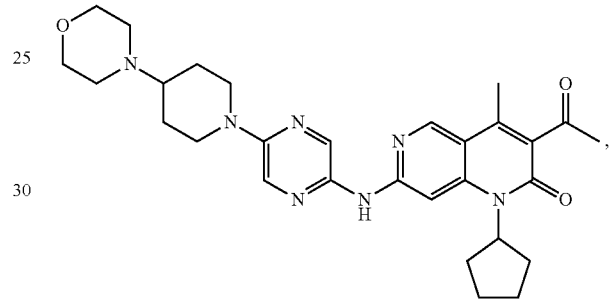
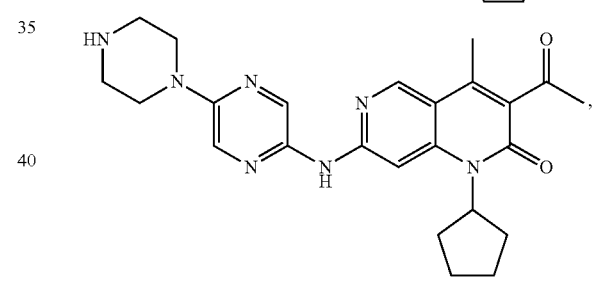
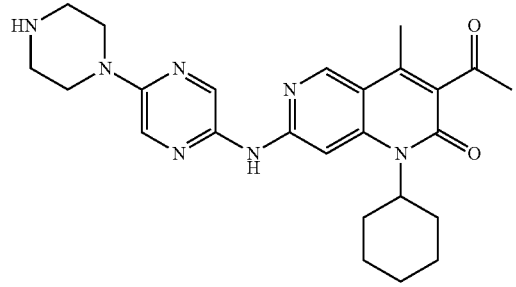
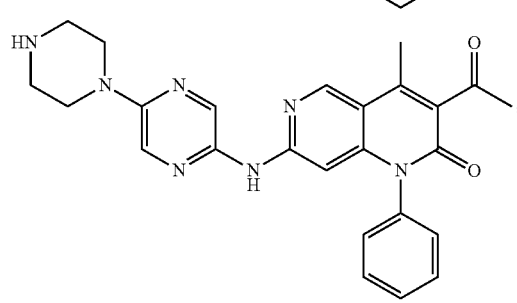

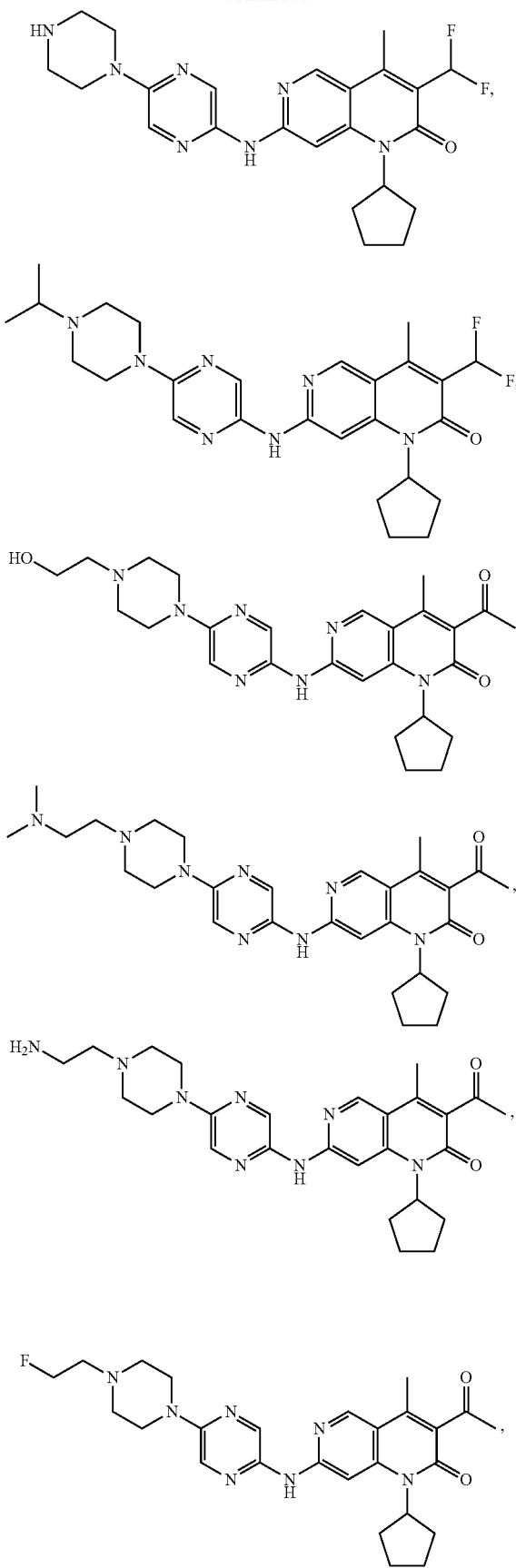
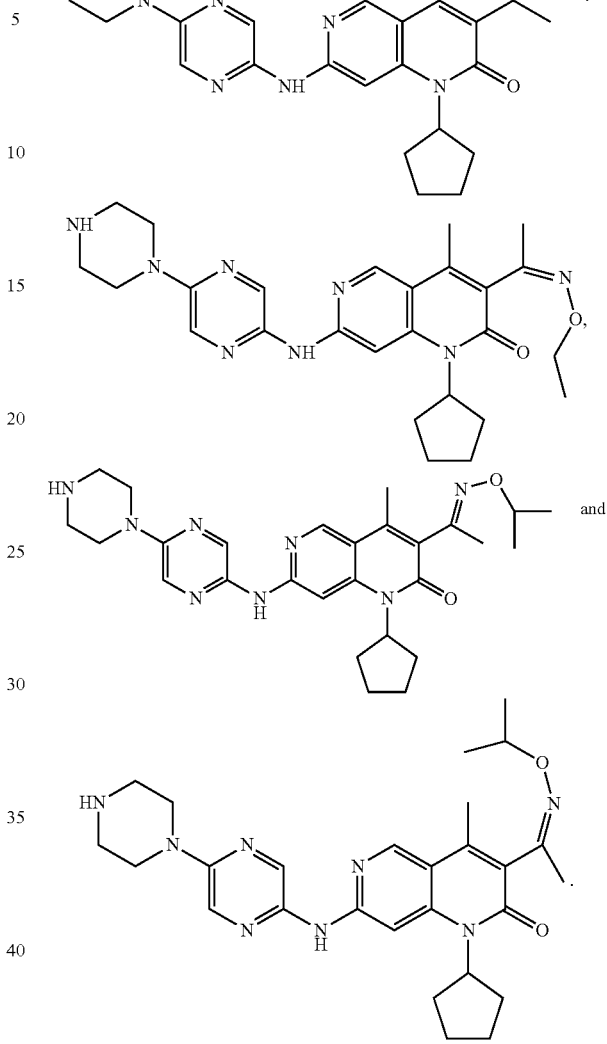

Other embodiments of the present invention can be obtained by the arbitrary combination of the above variables.

The present invention also provides a pharmaceutical composition, comprising a therapeutically effective amount of the above compound, the pharmaceutically acceptable salt thereof or the isomer thereof, and a pharmaceutically acceptable carrier.

The present invention also provides a use of the above compound, the pharmaceutically acceptable salt thereof or the isomer thereof in manufacturing a medicament for treating a cancer.

DEFINITION AND DESCRIPTION

Unless otherwise indicated, the following terms when used in the descriptions and the claims of the present invention have the following meanings. A specific term or phrase should not be considered indefinite or unclear in the absence of a particular definition, but should be understood in the ordinary sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present invention that is prepared by reacting the compound having a specific substituent of the present invention with a relatively non-toxic acid or base. When the compound of the present invention contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present invention contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like (refer to Berge et al., "*Pharmaceutical Salts*", *Journal of Pharmaceutical Science* 66: 1-19 (1977)). Certain specific compounds of the present invention that contain both basic and acidic functional groups can be converted to any base or acid addition salt.

Preferably, through bringing the salt into contact with a base or an acid in a conventional manner, then separating the parent compound, the neutral form of the compound is thereby regenerated. The difference between the parent form of the compound and its various salt forms lies in specific physical properties, such as different solubility in a polar solvent.

"Pharmaceutically acceptable salt" used herein belongs to a derivative of the compound of the present invention, wherein, the parent compound is modified by forming a salt with an acid or a base. Examples of the pharmaceutically acceptable salt include but are not limited to an inorganic acid or organic acid salt of a basic moiety such as amine, an alkali metal salt or an organic salt of an acidic moiety such as carboxylic acid, and the like. The pharmaceutically acceptable salt includes conventional non-toxic salt or quaternary ammonium salt of the parent compound, such as a salt formed by a non-toxic inorganic acid or an organic acid. The conventional non-toxic salt includes but is not limited to the salt derived from an inorganic acid and an organic acid, wherein the inorganic acid or organic acid is selected from the group consisting of 2-acetoxybenzoic acid, 2-hydroxyethanesulfonic acid, acetic acid, ascorbic acid, benzenesulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionic acid, lactic acid, lactose, dodecyl sulfonic acid, maleic acid, malic acid, mandelic acid, methanesulfonic acid, nitric acid, oxalic acid, pamoic acid, pantothenic acid, phenylacetic acid, phosphoric acid, polygalactanal acid, propionic acid, salicylic acid, stearic acid, subacetic acid, succinic acid, sulfamic acid, sulfanilic acid, sulfuric acid, tannin, tartaric acid and p-toluenesulfonic acid.

The pharmaceutically acceptable salt of the present invention can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof. Generally, non-aqueous media such as ether, ethyl acetate, ethanol, isopropanol or acetonitrile are preferred.

In addition to the salt form, the compound provided by the present invention also exists in prodrug form. The prodrug of the compound described herein is the compound that readily undergoes chemical change under physiological condition to be converted into the compound of the present invention. Additionally, the prodrug can be converted to the compound of the present invention by a chemical or biochemical method in vivo environment.

Certain compounds of the present invention can exist in a nonsolvated form or a solvated form, including hydrated form. Generally, the solvated form is equivalent to the nonsolvated form, and both are encompassed within the scope of the present invention.

Certain compounds of the present invention can have an asymmetric carbon atom (optical center) or a double bond. The racemate, diastereomer, geometric isomer and individual isomer are all encompassed within the scope of the present invention.

Unless otherwise specified, the absolute configuration of a stereogenic center is represented by a wedged solid bond ($\nearrow$) and a wedged dashed bond ($\nwarrow$), and the relative configuration of a stereogenic center is represented by a straight solid bond ($\nearrow$) and a straight dashed bond ($\nwarrow$). A wave line ($\sim$) represents a wedged solid bond ($\nearrow$) or a wedged dashed bond ($\nwarrow$), or represents a straight solid bond ($\nearrow$) or a straight dashed bond ($\nwarrow$).

When the compound described herein contains an olefinic double bond or other geometric asymmetric centers, E and Z geometric isomers are included unless otherwise specified. Likewise, all tautomeric forms are encompassed within the scope of the present invention.

The compound of the present invention may have a specific geometric or stereoisomeric form. The present invention contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope of the present invention. The substituent such as alkyl may have an additional asymmetric carbon atom. All these isomers and mixtures thereof are encompassed within the scope of the present invention.

Unless otherwise specified, the term "enantiomer" or "optical isomer" refers to stereoisomers that are mirror images of each other.

Unless otherwise specified, the term "cis-trans isomer" or "geometric isomer" is caused by the inability of a double bond or a single bond of carbon atoms on the ring to freely rotate.

Unless otherwise specified, the term "diastereomer" refers to stereoisomers in which the molecules have two or more chiral centers and are not mirror images of each other.

Unless otherwise specified, "(D)" or "(+)" stands for dextrorotation, "(L)" or "(−)" stands for levorotation, "(DL)" or "(±)" stands for racemization.

The compounds of the invention may be present in particular. Unless otherwise indicated, the terms "tautomer" or "tautomeric form" refer to the fact that the different functional isomers are in dynamic equilibrium at room temperature and can be rapidly converted into each other. If tautomers are possible (as in solution), the chemical equilibrium of the tautomers can be achieved. For example, proton tautomers (also known as prototropic tautomers) include interconversions by proton transfer, such as keto-enol isomerization and imine-enamine isomerization. The valence tautomer includes the mutual transformation of some bonding electrons. A specific example of keto-enol tautomerization is the interconversion between two tautomers of pentane-2,4-dione and 4-hydroxypent-3-en-2-one.

Unless otherwise specified, the terms "enriched in one isomer", "isomer enriched", "enriched in one enantiomer" or "enantiomer enriched" refer to the content of one of the isomers or enantiomers is less than 100%, and the content of the isomer or enantiomer is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless otherwise specified, the terms "excess of isomer" or "excess of enantiomer" refers to the difference between the relative percentages of the two isomers or enantiomers. For example, wherein, the content of one of the isomers or enantiomers is 90%, and the other one is 10%, then the excess of isomer or enantiomer (ee value) is 80%.

Optically active (R)- and (9-isomer, or D and L isomer can be prepared using chiral synthesis or chiral reagents or other conventional techniques. If one kind of enantiomer of certain compound of the present invention is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine).

The compound of the present invention may contain an unnatural proportion of atomic isotope at one or more than one atom(s) that constitute the compound. For example, the compound can be radiolabeled with a radioactive isotope, such as tritium ($^3H$), iodine-125 ($^{125}I$) or C-14 ($^{14}C$). For another example, hydrogen can be replaced by heavy hydrogen to form a deuterated drug, and the bond composed of barium and carbon is stronger than the bond composed of common hydrogen and carbon. Compared with undeuterated drugs, deuterated drugs have reduced side effects and increased drug stability, enhanced the efficacy and prolonged the biological half-life of the drug. All isotopic variations of the compound of the present invention, whether radioactive or not, are encompassed within the scope of the present invention.

The term "pharmaceutically acceptable carrier" refers to any agent or carrier medium which is capable of delivering an effective amount of the active substance of the present invention, does not interfere with the biological activity of the active substance and has no toxic side effect on the host or patient. The representative carrier includes water, oil, vegetable and mineral, cream base, lotion base, ointment base and the like. The base includes a suspending agent, a thickener, a penetration enhancer and the like. Their formulations are well known to the skilled in the cosmetic field or the topical pharmaceutical field. The additional information about the carrier can be referred to *Remington: The Science and Practice of Pharmacy,* 21*st Ed., Lippincott, Williams & Wilkins* (2005), the contents of which are incorporated herein by reference.

For a medicament or a pharmacologically active agent, the term "effective amount" or "therapeutically effective amount" refers to a nontoxic but sufficient amount to achieve a desired effect of the medicament or the agent. For the oral dosage form of the present invention, an "effective amount" of the active substance in the composition refers to an amount required for achieving a desired effect when combining with another active substance in the composition. The effective amount varies from person to person and is determined depending on the age and general condition of the recipient as well as the specific active substance. The appropriate effective amount in an individual case can be determined by the skilled in the art based on routine experiment.

The term "active ingredient", "therapeutic agent", "active substance" or "active agent" refers to a chemical entity which can effectively treat the target disorder, disease or condition.

"Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variants, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A.

When a bond of a substituent can be cross-linked to more than one atom on a ring, such substituent can be bonded to any atom of the ring. When an enumerative substituent does not indicate by which atom it is attached to a compound included in the general chemical formula but not specifically mentioned, such substituent can be bonded by any of its atoms. A combination of substituents and/or variants thereof is allowed only when such combination can result in a stable compound. For example, the structural unit

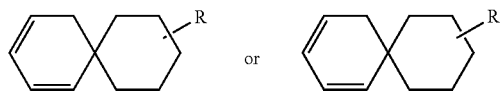

means that the substituent R can be located at any position on cyclohexyl or cyclohexadiene.

When the enumerative linking group does not indicate the direction for linking, the direction for linking is arbitrary, for example, the linking group L contained in

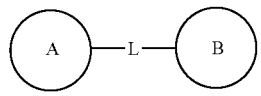

is -MW-, then -MW- can link ring A and ring B to form

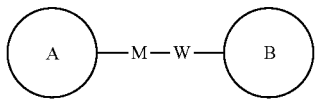

in the direction same as left-to-right reading order, and form

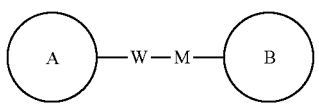

in the direction contrary to left-to-right reading order.

Unless otherwise specified, the term "hetero" represents a heteroatom or a heteroatomic group (e.g., an atomic group containing a heteroatom), including the atom except carbon (C) and hydrogen (H) and the atomic group containing the above heteroatom, for example, including oxygen (O), nitrogen (N), sulfur (S), silicon (Si), germanium (Ge), aluminum (Al), boron (B), —O—, —O—, =O, =S, —C(=O)O—, —C(=O)—, —C(=S)—, —S(=O), —S(=O)$_2$—, and the group consisting of —C(=O)N(H)—, —N(H)—, —C(=NH)—, —S(=O)$_2$N(H)— and —S(=O)N(H)—, each of which is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called ring includes a single ring, a double ring, a spiral ring, a fused ring or a bridged ring. The number of the atom on the ring is usually defined as the member number of the ring, for example, a "5-7 membered ring" means that 5 to 7 atoms are arranged on a ring. Unless otherwise specified, the ring optionally contains 1 to 3 heteroatoms. Therefore, a "5-7 membered ring" includes, for example, phenyl, pyridinyl and piperidinyl; on the other hand, the term "5-7 membered heterocycloalkyl ring" includes pyridyl and piperidinyl, but excluding phenyl. The term "ring" also includes a ring system containing at least one ring, wherein each ring independently meets the above definition.

Unless otherwise specified, the term "heterocycle" or "heterocyclo" refers to a stable monocyclic, bicyclic or tricyclic ring containing a heteroatom or a heteroatom group, which can be saturated, partially unsaturated or unsaturated (aromatic) and can contain carbon atoms and 1, 2, 3 or 4 ring heteroatoms independently selected from N, O and S, wherein any of the above heterocycle can be fused to a benzene ring to form a bicyclic ring. Nitrogen and sulfur heteroatoms can optionally be oxidized (i.e., NO and S(O)p, p is 1 or 2). Nitrogen atom can be substituted or unsubstituted (i.e., N or NR, wherein R is H or other substituents already defined herein). The heterocycle can be attached to the pendant group of any heteroatom or carbon atom to form a stable structure. If the resulting compound is stable, the heterocycle described herein may have a substitution at a carbon or nitrogen position. Nitrogen atom on the heterocycle is optionally quaternized. In a preferred embodiment, when the total number of S and O atom of the heterocycle is more than 1, the heteroatom is not adjacent to each other. In another preferred embodiment, the total number of S and O atom of the heterocycle is not more than 1. As used herein, the term "aromatic heterocyclic group" or "heteroaryl" refers to a stable 5-, 6- or 7-membered monocyclic or bicyclic or 7-, 8-, 9- or 10-membered bicyclic heterocyclic aromatic ring which contains carbon atoms and 1, 2, 3 or 4 ring heteroatoms independently selected from N, O, and S. Nitrogen atom can be substituted or unsubstituted (i.e., N or NR, wherein R is H or other substituents already defined herein). Nitrogen and sulfur heteroatoms may optionally be oxidized (i.e., NO and S(O)$_p$, p is 1 or 2). It is worth noting that the total number of S and O atom of an aromatic heterocycle is not more than one. The bridged ring is also included in the definition of the heterocycle. A bridged ring is formed when one or more than one atom (i.e, C, O, N or S) link two non-adjacent carbon or nitrogen atoms. A preferred bridged ring includes, but not limited to one carbon atom, two carbon atoms, one nitrogen atom, two nitrogen atoms and one carbon-nitrogen group. It is worth noting that a bridge always converts a monocyclic ring to a tricyclic ring. In a bridged ring, the substituent on the ring may also be present on the bridge.

Examples of the heterocyclic compound include, but are not limited to: acridinyl, azocinyl, benzimidazolyl, b enzofuranyl, benzomercaptofuranyl, benzomercaptophenyl, benzoxazolyl, b enxoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxindolyl, pyrimidinyl, phenanthridinyl, phenanthrolinyl, phenazine, phenothiazine, benzoxanthinyl, phenoloxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyrido-oxazolyl, pyrido-imidazolyl, pyrido-thiazolyl, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthi enyl, thieno-oxazolyl, thieno-thiazolyl, thieno-imidazolyl, thienyl, triazinyl, 1,2,3-triazolyl, 1,2,4-triazolyl, 1,2,5-triazolyl, 1,3,4-triazolyl and xanthenyl. Also included are fused-ring compounds and spiro compounds.

Unless otherwise specified, the term "hydrocarbyl" or its hyponyms (e.g., alkyl, alkenyl, alkynyl, and aryl, etc.), by itself or as part of another substituent, refers to a linear, branched chain or cyclic hydrocarbon radical or any combination thereof. They can be fully saturated (e.g., alkyl), mono- or polyunsaturated (e.g., alkenyl, alkynyl, and aryl), can be mono-, di- or poly-substituted, can be monovalent (e.g., methyl), divalent (e.g., methylene) or multivalent (e.g., methenyl), can also include a divalent or multivalent group, have a specified number of carbon atom (for example, $C_1$-$C_{12}$ indicates 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes, but is not limited to aliphatic hydrocarbyl and aromatic hydrocarbyl. The aliphatic hydrocarbyl includes linear and cyclic hydrocarbyl, specifically includes but not limited to alkyl, alkenyl, and alkynyl. The aromatic hydrocarbyl includes but is not limited to 6-12 membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl, tert-butyl, isobutyl, sec-butyl, cyclohexyl, (cyclohexyl)methyl, cyclopropylmethyl, and the homolog or isomer of n-amyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and more higher homologs and isomers.

Unless otherwise specified, the term "heterohydrocarbyl" or its hyponyms (such as heteroalkyl, heteroalkenyl, heteroalkynyl, and heteroaryl, etc.), by itself or as part of another substituent, refers to a stable linear, branched or cyclic hydrocarbon group or any combination thereof, which has a specified number of carbon atoms and at least one heteroatom. In some embodiments, the term "heteroalkyl" by itself or in combination with another term refers to a stable linear, branched hydrocarbon radical or a combination thereof which has a specified number of carbon atoms and at least one heteroatom. In a specific embodiment, a heteroatom is selected from B, O, N and S, wherein nitrogen and sulfur atoms are optionally oxidized and the nitrogen atom is optionally quaternized. The heteroatom or heteroatom group can be located at any interior position of a heterohydrocarbyl, including the position where the hydrocarbyl attaches to the rest part of the molecule. But the terms "alkoxy", "alkylamino" and "alkylthio" (or thioalkyl) are used by the conventional meaning and refer to an alkyl group connected to the rest part of the molecule via an oxygen atom, an amino or a sulfur atom respectively. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$—$CH_3$. Up to two consecutive heteroatoms can be present, such as, —$CH_2$—NH—$OCH_3$.

Unless otherwise specified, the term "cyclohydrocarbyl", "heterocyclohydrocarbyl" or its hyponyms (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g., heteroalkyl, and heterocycloalkyl), one heteroatom can occupy the position where the heterocycle attaches to the remainder position of the molecule. Examples of the cycloalkyl include, but are not limited to, cyclopentyl, cyclohexyl, 1-cyclohexenyl, 3-cyclohexenyl, cycloheptyl and the like. Non-limiting examples of heterocycloalkyl include 1-(1,2, 5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydro-thiophen-2-yl, tetrahydro-thiophen-3-yl, 1-piperazinyl and 2-piperazinyl.

Unless otherwise specified, the term "alkyl" refers to a linear chain or branched saturated hydrocarbon group, can be mono-substituted (e.g., —$CH_2F$) or poly-substituted (e.g., —$CF3$), can be monovalent (e.g. methyl), divalent (e.g., methylene) or multivalent (e.g., methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, the term "alkenyl" refers to an alkyl group having one or more than one carbon-carbon double bonds at any position on the chain, can be mono-substituted or poly-substituted, and can be monovalent, divalent or multivalent. Examples of alkenyl include ethenyl, propenyl, butenyl, pentenyl, hexenyl, butadienyl, pentadienyl, hexadienyl, and the like.

Unless otherwise specified, the term "alkynyl" refers to an alkyl group having one or more than one carbon-carbon triple bonds at any position on the chain, can be mono-substituted or poly-substituted, and can be monovalent, divalent or multivalent. Examples of alkynyl include ethynyl, propynyl, butynyl, pentynyl, and the like.

Unless otherwise specified, cycloalkyl includes any stable cyclic or polycyclic hydrocarbyl, and any carbon atom is saturated, can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

Unless otherwise specified, cycloalkenyl includes any stable cyclic or polycyclic hydrocarbyl having one or more than one unsaturated carbon-carbon single bonds at any position on the ring, can be mono-substituted or poly-substituted, and can be monovalent, divalent or multivalent.

Examples of the cycloalkenyl include, but are not limited to, cyclopentenyl, cyclohexenyl and the like.

Unless otherwise specified, cycloalkynyl includes any stable cyclic or polycyclic hydrocarbyl having one or more carbon-carbon triple bonds at any position on the ring, can be mono-substituted or poly-substituted, and can be monovalent, divalent or multivalent.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo($C_1$-$C_4$)alkyl" is meant to include, but not limited to, trifluoromethyl, 2,2,2-trifluoroethyl, 4-chlorobutyl, 3-bromopropyl and the like. Examples of haloalkyl include, but not limited to trifluoromethyl, trichloromethyl, pentafluoroethyl and pentachloroethyl.

The term "alkoxy" represents any alkyl defined above having a specified number of carbon atoms attached by an oxygen bridge. Unless otherwise specified, $C_{1-6}$ alkoxy includes $C_1$, $C_2$, $C_3$, $C_4$, $C_5$ and $C_6$ alkoxy. Examples of alkoxy include, but not limited to methoxy, ethoxy, n-propoxy, isopropoxy, n-butoxy, sec-butoxy, tert-butoxy, n-pentyloxy and S-pentoxy.

Unless otherwise specified, the term "aryl" refers to a polyunsaturated aromatic substituent, can be mono-, di- or poly-substituted, can be a monovalent, divalent or multivalent, can be a single ring or a multiple ring (e.g. one to three rings; wherein at least one ring is aromatic), which are fused together or connected covalently. The term "heteroaryl" refers to an aryl (or ring) containing one to four heteroatoms. In an illustrative example, the heteroatom is selected from B, O, N and S, wherein nitrogen and sulfur atoms are optionally oxidized and nitrogen atom is optionally quaternized. A heteroaryl may attach to the rest part of a molecule via a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furanyl, thienyl, pyridyl, pyrimidinyl benzothiazolyl, purinyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of the above aryl and heteroaryl ring system is selected from the acceptable substituent described below.

Unless otherwise specified, when aryl combines with other terms (such as aryloxy, arylthio, arylalkyl), the aryl includes the aryl and heteroaryl ring as defined above. Thus, the term "aralkyl" is meant to include the group (e.g., benzyl, phenethyl, pyridylmethyl, etc.) where an aryl is attached to an alkyl, including an alkyl where the carbon atom (e.g, methylene) has been replaced by an atom such as oxygen, for example, phenoxymethyl, 2-pyridyloxy, 3-(1-naphthyloxy)propyl, and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzene-sulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g, acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl)methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g, acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compound of the present invention can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment of the present invention.

Compounds are named manually or by ChemDraw® software, the commercially available compounds use their vendor directory names.

All of the solvents used in the present invention are commercially available. This present invention adopts the abbreviating words as followed: "MeCN" refers to acetonitrile; "DCM" refers to dichloromethane; "THF" refers to tetrahydrofuran; "AcOH" refers to acetic acid; "TFA" refers to trifluoroacetic acid; "DMF" refers to N,N-dimethylformamide; "$H_2O$" refers to water; "Boc" refers to t-butoxycarbonyl, and "Bn" refers to benzyl, both of which are amine protecting groups; "DIPEA" refers to diisopropylethylamine; "$MnO_2$" refers to manganese dioxide; "DIBAL-H" refers to diisobutylaluminum hydride; "NaH" refers to sodium hydride; "MeMgBr" refers to methylmagnesium bromide; "LiHMDS" refers to lithium hexamethyldisilazide; "$Pd_2(dba)_3$" refers to tris(dibenzylideneacetone)dipalladium; "$Pd(dppf)Cl_2$" refers to [1,1'-bis(diphenylphosphino)ferrocene]dichloropalladium; "$Pd(OAc)_2$" refers to palladium acetate; "$Pd(PPh_3)_4$" refers to tetrakis(triphenylphosphine)palladium; "$Pd(PPh_3)_2Cl_2$" represents bis(triphenylphosphine)palladium dichloride; "PO" refers to oral intake; "Xphos" refers to 2-dicyclohexylphosphine-2',4',6'-triisopropylbiphenyl; "BINAP" refers to (±)-2,2'-bis-(diphenylphosphino)-1,1'-binaphthyl; "Xphos-Pd-G1" refers to chloro(2-dicyclohexylphosphino-2',4',6'-triisopropyl-1,1'-biphenyl)[2-(2'-aminoethylphenyl)]palladium(II); "Xphos-PD-$G_2$" refers to chloro(2-dicyclohexylphosphino-2',2',6'-triisopropyl-1,1'-biphenyl)[2-(2'-amino-1,1'-biphenyl)]palladium(II); "Xphos-Pd-G3" refers to methanesulfonic acid(2-dicyclohexylphosphino-2',4',6'-triisopropyl-1,1'-biphenyl)[2-(2'-amino-1,1'-biphenyl)]palladium(II); "NIS" refers to N-iodoibutylimide; "NBS" refers to N-bromosuccinimide; "$Br_2$" refers to liquid bromine; "$NH_2OH.HCl$" refers to hydroxylamine hydrochloride; "NaOAc" refers to sodium acetate; "$Cs_2CO_3$" refers to cesium carbonate;

"OsO$_4$" refers to osmium tetroxide; "NaIO$_4$" refers to sodium periodate; "DAST" refers to diethylaminosulfur trifluoride; "PO" refers to intragastric administration; "QD" refers to once a day.

TECHNICAL EFFECT

The compounds of the present invention have significant inhibitory activity against CDK4 and CDK6 kinase. Meanwhile, the compounds of the present invention have significant proliferation inhibitory activity against H358 lung cancer cells. Some compounds of the present invention have higher inhibitory activity against NCI-H358 cell proliferation than the reference compound Palbociclib.

Compared with the reference compounds Palbociclib and LY2835219, the compounds of the present invention have higher permeability, and the absorption and transport in vivo are less likely to be affected by the efflux transporters. The better permeability allows the compounds of the present invention to be more wildly distributed in the tissues in vivo, such as in the lung, resulting in better anti-tumor efficacy in vivo. Meanwhile, better permeability makes it possible for the compounds of the present invention to penetrate the blood-brain barrier and achieve the purpose of treating brain metastasis (including lung cancer).

The compounds of the present invention have higher kinetic solubility than Palbociclib. The kinetic solubility can help us better understand the data from in vitro and in vivo biotest. Furthermore, the compounds of the present invention have improved liver microsome stability in human, rats and mice, and the clearance rate thereof is low. In the subcutaneously implanted colorectal cancer HCT-116 model assay, the weight loss of the animals treated with the compounds of the present invention was smaller, indicating that the compounds of the present invention have better safety.

The compounds of the present invention exhibit significant anti-tumor activity on LU-01-0393 lung cancer patient-derived tumor tissue xenograft (PDX). Although some compounds of the present invention have similar effect in inhibiting the growth of the tumor volume compared to the reference compound Palbociclib, the dosage thereof is only ½ of that of the reference compound. It can be indicated that the compounds of the present invention have superior anti-tumor activity at the same dose. From the point of view of administration, it is possible to reduce the dosage of the medicament used by patients and improve the compliance. In addition, in the subcutaneously implanted non-small cell lung cancer NCI-H358 model assay, the weight of the animals treated with the compound of the present invention did not only decrease significantly, but also gradually increased at the same dose, indicating that the compound of the present invention is more advanced and have considerably improved safety than the prior art. To sum up, the compounds of the present invention have better pharmaceutical prospects than the prior art.

DETAILED DESCRIPTION OF THE INVENTION

The following examples further illustrate the present invention, but the present invention is not limited thereto. The present invention has been described in detail in the text, and its specific embodiments have also been disclosed, for one skilled in the art, it is obvious to modify and improve the embodiments of the present invention within the spirit and scope of the present invention.

The compounds of the present invention can be prepared by a series of synthetic procedures, wherein, R$_1$, R$_2$, ring A and ring B are as defined above.

Reaction Scheme 1: Preparation of the compound of formula (I)

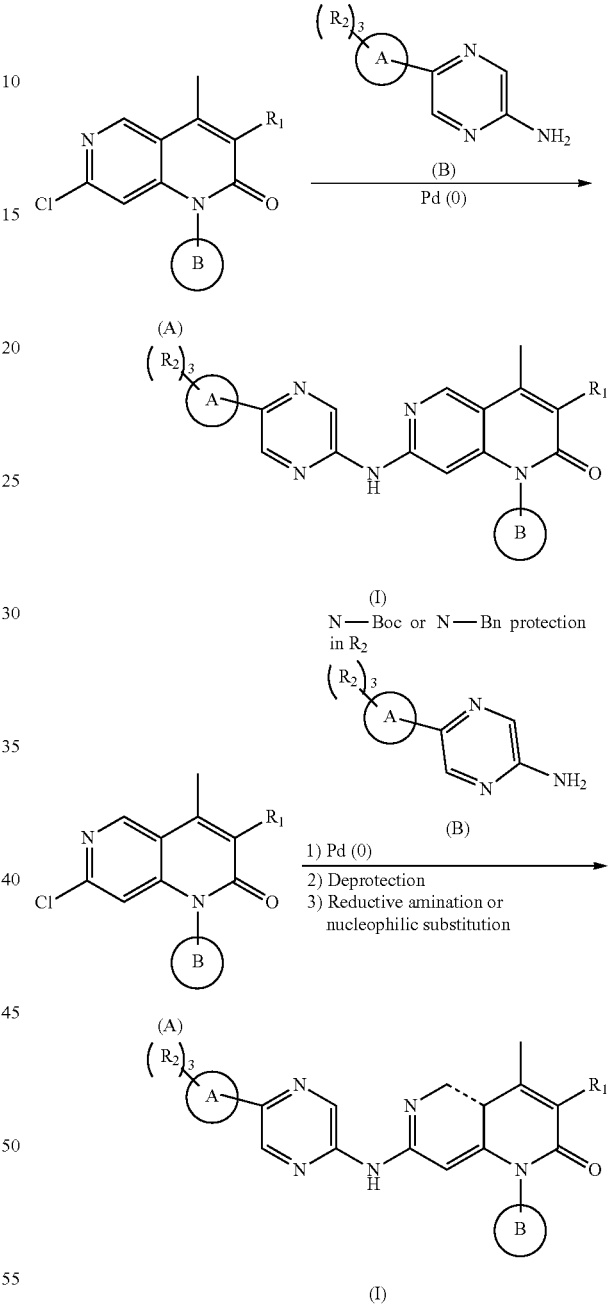

When no N-Boc or N-Bn protecting group is present in the heterocyclic aromatic amine (B), the compound of formula (I) is given by the reaction of 2-chloro-1,6-naphthyridin-2-one (A) and the heterocyclic aromatic amine (B) according to the above reaction shown in Reaction Scheme 1. The reaction requires a suitable catalyst (such as palladium acetate), a suitable ligand (such as Xphos), a suitable base (such as cesium carbonate) and a suitable solvent (such as 1,4-dioxane). According to Reaction Scheme 1, the reaction is more suitably carried out at high temperature.

When an N-Boc or N-Bn protecting group is present in the heterocyclic aromatic amine (B), the compound of formula (I) can still be given by the reaction of 2-chloro-1,6-naphthyridin-2-one (A) and the heterocyclic aromatic amine (B) according to the below reaction shown in Reaction Scheme 1. The Boc group is removed under strong acid conditions (such as trifluoroacetic acid), while the Bn group is removed under reducing conditions (such as palladium on carbon (wetted with water)/ammonium formate). The final deprotected intermediate is subjected to the reductive amination under reducing conditions (such as sodium cyanoborohydride) or the nucleophilic substitution reaction under basic conditions (such as potassium carbonate) to give the compound of formula (I).

reaction is more suitably carried out at high temperature. Afterwards, Compound (E) is deprotected under strongly acidic conditions (such as trifluoroacetic acid) to give 2-chloro-1,6-naphthyridin-2-one (A).

When $R_1$ is difluoromethyl, in terms of the below reaction shown in Reaction Scheme 2, Compound (G) can be given by the coupling reaction of 2-chloro-3-bromo-1,6-naphthyridin-2-one (C) and a vinyl boron reagent (F). The reaction requires a suitable catalyst (such as $Pd(PPh_3)_2Cl_2$), a suitable base (such as cesium carbonate) and a suitable solvent (such as 1,4-dioxane/water). According to Reaction Scheme 2, the reaction is more suitably carried out at high temperature. Compound (H) is prepared by the oxidation reaction of Reaction Scheme 2: Preparation of 2-chloro-1,6-naphthyridin-2-one (A)

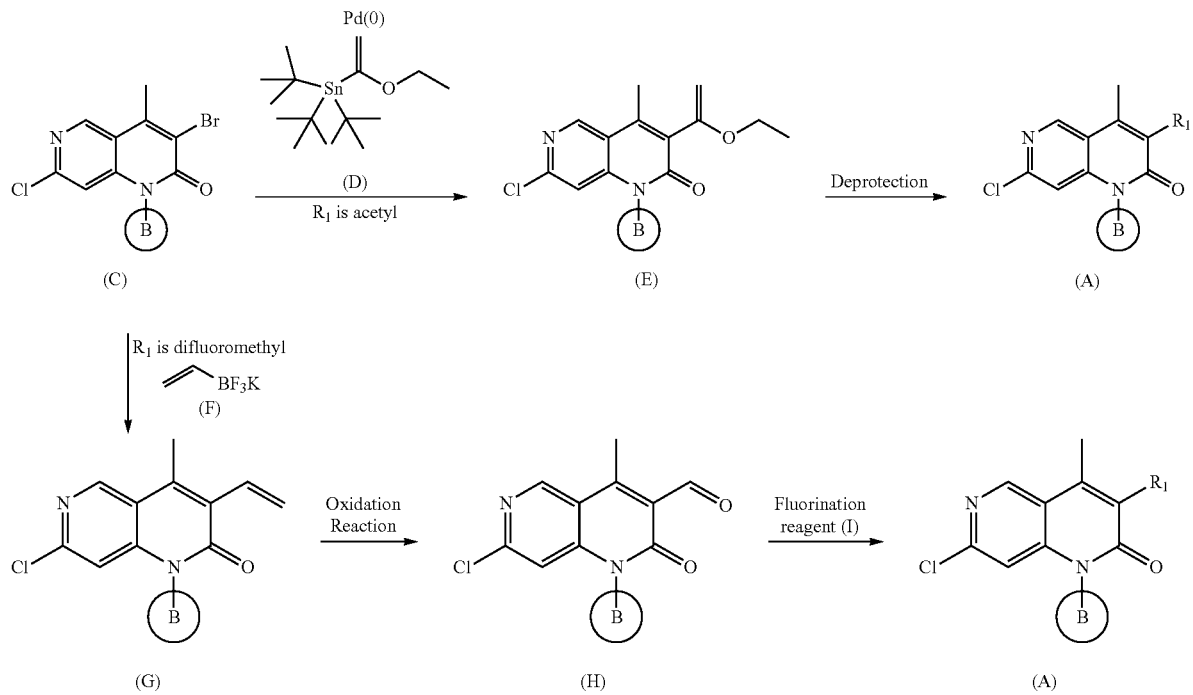

When $R_1$ is acetyl, in terms of the above reaction shown in Reaction Scheme 2, Compound (E) can be given by the coupling reaction of 2-chloro-3-bromo-1,6-naphthyridin-2-one (C) and a tin reagent (D). The reaction requires a suitable catalyst (such as $Pd(PPh_3)_4$) and a suitable solvent (such as toluene). According to Reaction Scheme 2, the Compound (G) in the presence of an oxidizing agent, and the reaction requires a suitable oxidizing agent (such as sodium periodate). Afterwards, 2-chloro-1,6-naphthyridin-2-one (A) is given by the reaction of Compound (H) with a fluorination reagent (I), and the reaction requires a suitable fluorinating reagent (such as DAST).

Reaction Scheme 3: Preparation of 2-chloro-3-bromo-1,6-naphthyridin-2-one (C)

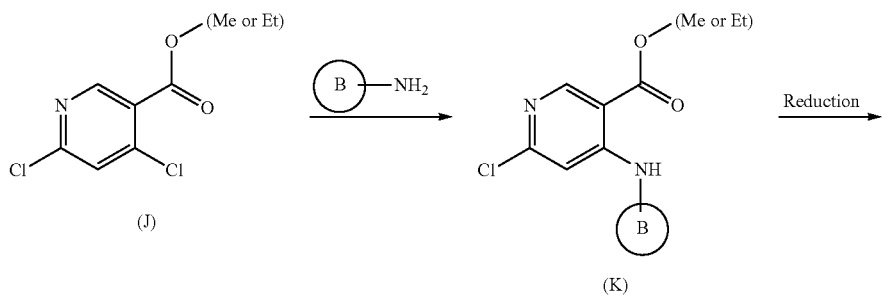

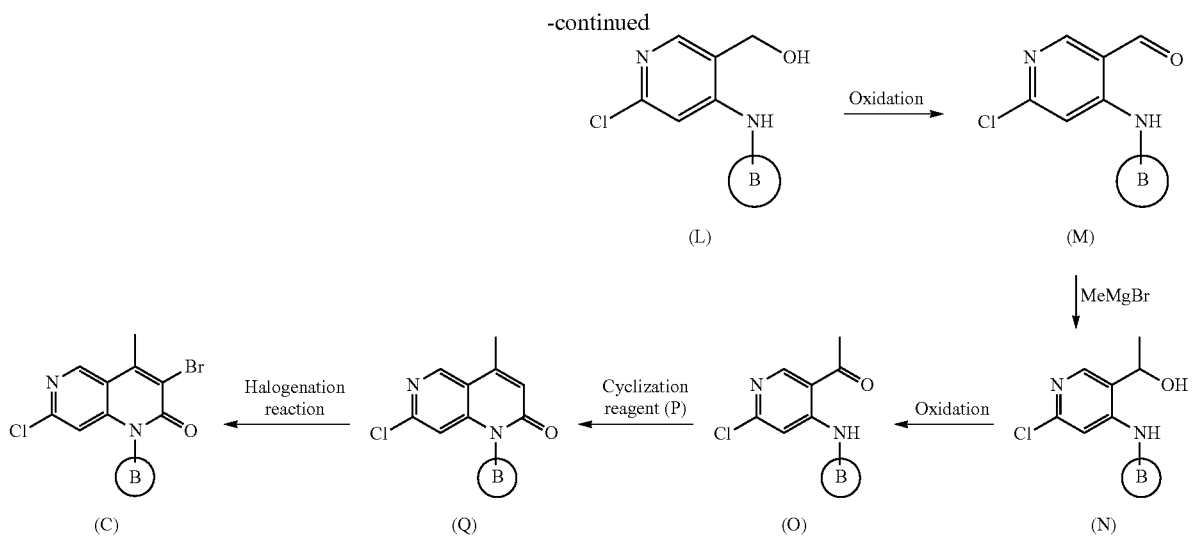

In terms of the reaction shown in Reaction Scheme 3, Compound (K) can be prepared by the reaction of 4,6-dichloronicotinate (J) with a primary amine, and the reaction requires a suitable base (such as triethylamine) and a suitable solvent (such as acetonitrile). Compound (K) is subjected to a reduction reaction to give Compound (L). The reaction requires a suitable reducing agent (such as DIBAL-H) and a suitable solvent (such as anhydrous tetrahydrofuran). Compound (M) can be prepared by oxidation reaction of Compound (L), and the reaction requires a suitable oxidizing agent (such as active manganese dioxide). Compound (M) and methylmagnesium bromide are subjected to the nucleophilic addition reaction to give Compound (N), and the reaction requires a suitable solvent (such as anhydrous tetrahydrofuran). According to the Reaction Scheme 3, the reaction is more suitably carried out at a low temperature. Compound (N) is subjected to an oxidation reaction to give Compound (O), and the reaction requires a suitable oxidizing agent (such as active manganese dioxide). The compound (Q) can be prepared by condensation and cyclization reaction of Compound (O) with a cyclization reagent (P), and the reaction requires a suitable cyclizing agent (such as triethylphosphorylacetate, ethyl acetate), a suitable base (such as sodium hydrogen, LiHMDS) and a suitable solvent (such as tetrahydrofuran). According to Reaction Scheme 3, the reaction is more suitably carried out at high temperature. Afterwards, Compound (Q) is subjected to halogenation reaction to give Compound (C), and the halogenating reagent can be $Br_2$, NBS or NIS, and the reaction requires a suitable solvent (such as N,N-dimethylformamide, acetonitrile).

Reaction Scheme 4: Preparation of heterocyclic aromatic amine (B)

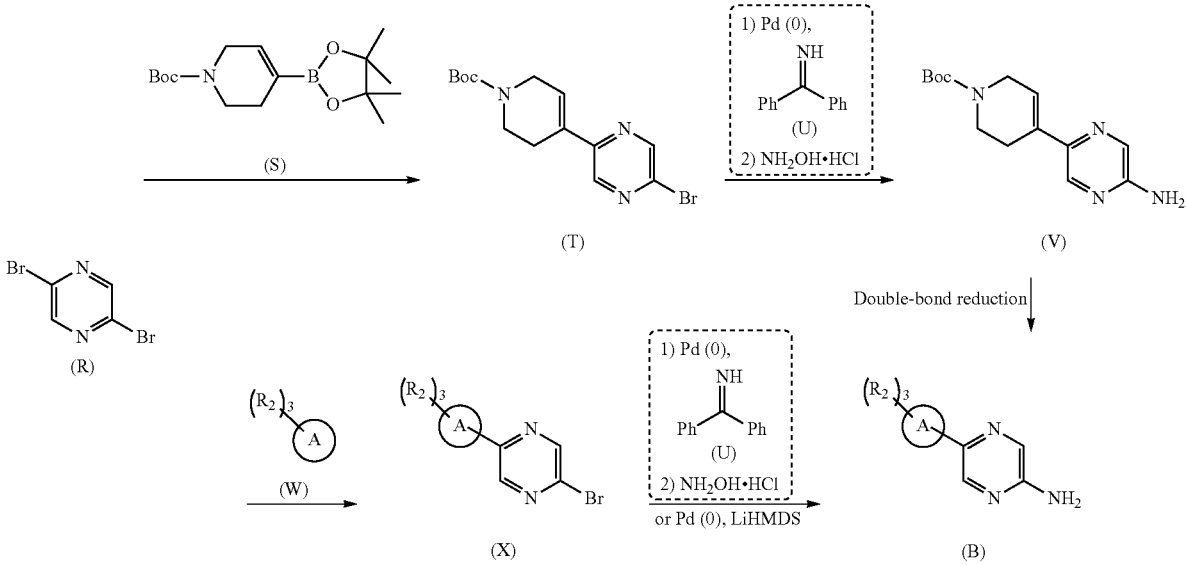

In terms of the reaction shown in Reaction Scheme 4, heterocyclic aromatic amine (B) can be prepared by the following two methods: 1) a bromine atom on 2,5-dibromopyrazine (R) and borate compound (S) are subjected to the palladium-catalyzed coupling reaction to give Compound (T). Compound (T) is reacted with diphenylmethylimine (U) under palladium catalysis, and then reacted with hydroxylamine hydrochloride under alkaline conditions to give Compound (V). Finally, Compound (V) is subjected to the reduction of double bond to give heterocyclic aromatic amine (B); 2) a bromine atom on the 2,5-dibromopyrazine (R) is substituted by a commercially available or synthetic amine (W) to give Compound (X). Heterocyclic aromatic amine (B) can be prepared by the following two methods via Compound (X): i) Compound (X) is reacted with dibenzylimine (U) under palladium catalysis, and then reacted with hydroxylamine hydrochloride under alkaline conditions to give heterocyclic aromatic amine (B); ii) Compound (X) is reacted with LiHMDS under palladium catalysis to prepare heterocyclic aromatic amine (B).

Schedule A

Synthesis of Intermediate A and Intermediate B

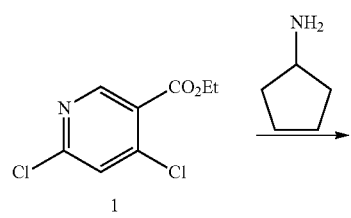

1

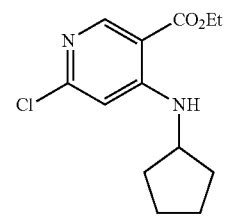 [SMILES: CCOC(=O)c1cnc(Cl)cc1NC1CCCC1]

2

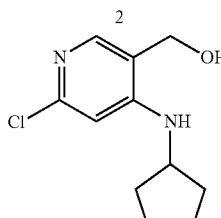

3

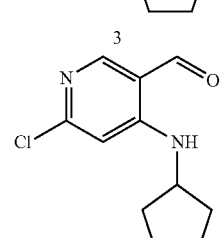

4

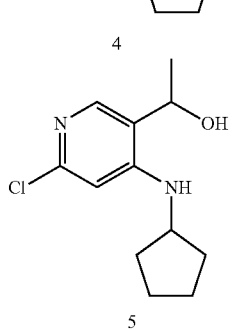

5

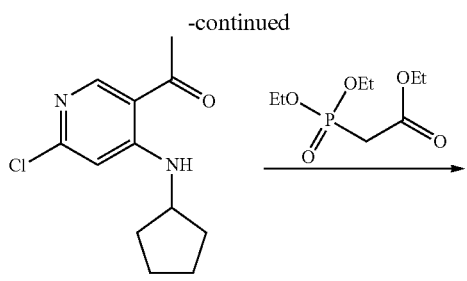

6

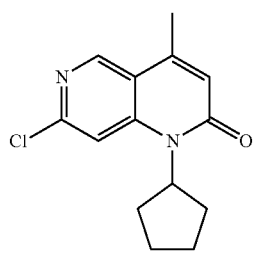

7

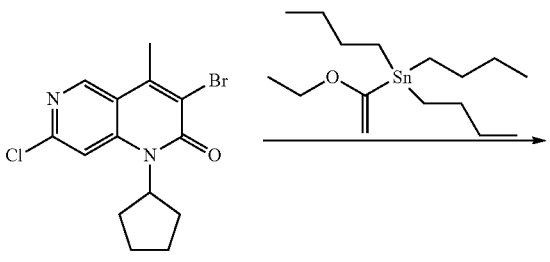

Intermediate A

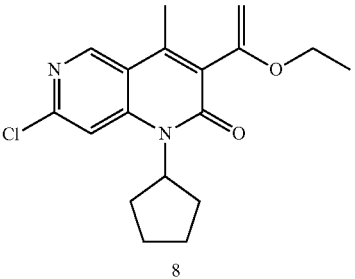

8

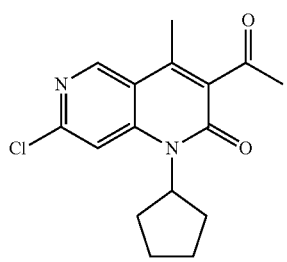

Intermediate B

Step 1:

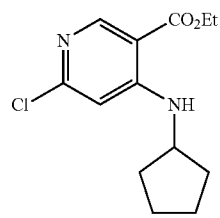

N,N-diisopropylethylamine (17.62 g, 136.32 mmol, 3.00 eq.) and cyclopentylamine (3.87 g, 45.44 mmol, 1.00 eq.) were added to a solution of ethyl 4,6-dichloronicotinate (Compound 1) (10.00 g, 45.44 mmol, 1.00 eq.) in acetonitrile (100.00 mL). The reaction mixture was stirred at 25° C. for 16 hours. The remaining starting material was confirmed by TLC, and then the reaction mixture was heated to 50° C. and stirred for 8 hours. The completion of the reaction was confirmed by TLC (petroleum ether:ethyl acetate=10:1). The mixture was concentrated, and the obtained crude product was dissolved in ethyl acetate (100 mL), wash with saturated brine (50 mL×2) and dried over anhydrous sodium sulfate, followed by filtration. The filtrate was concentrated and the obtained crude product was purified by silica gel column chromatography (petroleum ether:ethyl acetate=10:1) to give the title compound (Compound 2) (9.50 g, 35.35 mmol, yield: 77.80%). $^1$H NMR (400 MHz, CDCl$_3$) δ 8.67 (s, 1H), 8.20 (d, J=4.8 Hz, 1H), 6.58 (s, 1H), 4.35 (q, J=7.2 Hz, 2H), 3.88-3.80 (m, 1H), 2.12-2.04 (m, 2H), 1.82-1.75 (m, 2H), 1.74-1.67 (m, 2H), 1.63-1.57 (m, 2H), 1.40 (t, J=7.2 Hz, 3H); LCMS (ESI) m/z: 269.0 (M+1).

Step 2:

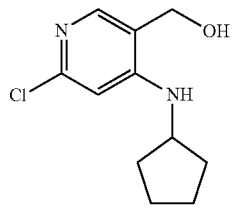 [SMILES: OCc1cnc(Cl)cc1NC1CCCC1]

DIBAL-H (1M, 70.70 mL, 2.00 eq.) was added dropwise to a solution of ethyl 6-chloro-4-(cyclopentylamino)nicotinate (Compound 2) (9.50 g, 35.35 mmol, 1.00 eq.) in tetrahydrofuran (100.00 mL) at −30° C. under nitrogen atmosphere. After the dropwise addition, the reaction mixture was warmed to 25° C. and stirred for 16 hours. The completion of the reaction was confirmed by TLC (petroleum ether:ethyl acetate=5:1). The mixture was cooled to 0° C., quenched with saturated aqueous sodium sulfate solution (50 mL) and extracted with ethyl acetate (30 mL×3). The combined organic layer was washed with saturated brine (50 mL×2) and dried over anhydrous sodium sulfate, followed by filtration. The filtrate was concentrated to give the title compound (Compound 3) (7.50 g, 33.08 mmol, yield: 93.59%). $^1$H NMR (400 MHz, CDCl$_3$) δ 7.71 (s, 1H), 6.51 (s, 1H), 5.57 (d, J=5.2 Hz, 1H), 4.60 (s, 2H), 3.86-3.77 (m, 1H), 2.12-2.03 (m, 2H), 1.82-1.62 (m, 4H), 1.60-1.50 (m, 2H).

Step 3:

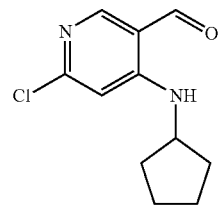 [SMILES: O=Cc1cnc(Cl)cc1NC1CCCC1]

Activated manganese dioxide (28.76 g, 330.80 mmol, 10.00 eq.) was added to a solution of (6-chloro-4-(cyclopentylamino)-pyridin-3-yl)methanol (Compound 3) (7.50 g, 33.08 mmol, 1.00 eq.) in dichloromethane (80.00 mL). The reaction mixture was stirred at 25° C. for 16 hours. The completion of the reaction was confirmed by TLC (petroleum ether:ethyl acetate=5:1). The reaction mixture was filtered, and the filtered cake was washed with dichloromethane (50 mL). The filtrate was concentrated to give the title compound (Compound 4) (7.00 g, 31.15 mmol, yield: 94.18%). $^1$H NMR (300 MHz, CDCl$_3$) δ 9.75 (s, 1H), 8.57 (d, J=6.8 Hz, 1H), 8.20 (s, 1H), 6.53 (s, 1H), 3.85-3.73 (m, 1H), 2.05-1.94 (m, 2H), 1.78-1.48 (m, 6H).

Step 4:

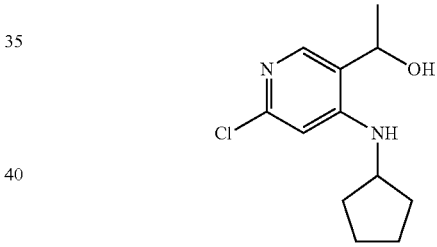

Methylmagnesium bromide (3M, 25.96 mL, 2.50 eq.) was added dropwise to a solution of 6-chloro-4-(cyclopentylamino)nicotinaldehyde (Compound 4) (7.0 g, 31.15 mmol, 1.00 eq.) in tetrahydrofuran (70.00 mL) at −10° C. under nitrogen atmosphere. After the dropwise addition, the mixture was stirred at this temperature for 1 hour. The completion of the reaction was confirmed by TLC (petroleum ether:ethyl acetate=5:1). The reaction mixture was quenched with saturated aqueous ammonium chloride solution (30 mL) and extracted with ethyl acetate (50 mL×3). The combined organic layer was washed with saturated brine (80 mL×2) and dried over anhydrous sodium sulfate, followed by filtration. The filtrate was concentrated to give the title compound (Compound 5) (6.70 g, 27.83 mmol, yield: 89.35%). $^1$H NMR (300 MHz, CDCl$_3$) δ 7.50 (s, 1H), 6.37 (s, 1H), 6.01 (d, J=6.4 Hz, 1H), 4.76 (q, J=6.4 Hz, 1H), 3.75-3.64 (m, 1H), 1.97-1.90 (m, 2H), 1.75-1.50 (m, 6H), 1.46 (d, J=6.6 Hz, 3H).

Step 5:

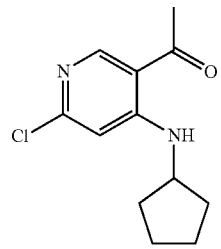 [SMILES: CC(=O)c1cnc(Cl)cc1NC1CCCC1]

Active manganese dioxide (24.20 g, 278.30 mmol, 10.00 eq.) was added to a solution of 1-(6-chloro-4-(cyclopentylamino)pyridin-3-yl)ethanol (Compound 5) (6.70 g, 27.83 mmol, 1.00 eq.) in dichloromethane (70.00 mL). The reaction mixture was stirred at 25° C. for 16 hours. The remaining starting material was confirmed by TLC, and then the reaction mixture was heated to 50° C. and stirred for 8 hours. The completion of the reaction was confirmed by TLC (petroleum ether:ethyl acetate=5:1). The reaction mixture was cooled to 20° C., followed by filtration. The filter cake was washed with dichloromethane (50 mL). The filtrate was concentrated to give the title compound (Compound 6) (6.00 g, 25.14 mmol, yield: 90.32%). $^1$H NMR (300 MHz, CDCl$_3$) δ 9.22 (s, 1H), 8.59 (s, 1H), 6.60 (s, 1H), 3.90-3.79 (m, 1H), 2.58 (s, 3H), 2.14-2.00 (m, 2H), 1.87-1.67 (m, 4H), 1.63-1.53 (m, 2H).

Step 6:

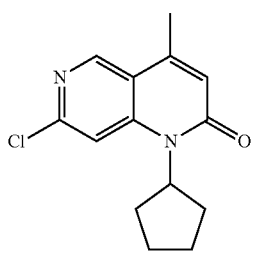

Sodium hydride (2.61 g, 65.36 mmol, 2.60 eq., 60% purity) was added to a solution of triethylphosphorylacetate (14.65 g, 65.36 mmol, 2.60 eq.) in tetrahydrofuran (60.00 mL) in batches at 0° C. under nitrogen atmosphere. The reaction mixture was stirred at this temperature for 20 minutes, and then 1-(6-chloro-4-(cyclopentylamino) pyridin-3-yl)ethanone (Compound 6) (6.00 g, 25.14 mmol, 1.00 eq.) was added to the reaction mixture. After the dropwise addition, the reaction mixture was heated to 70° C. and stirred for 16 hours. The completion of the reaction was confirmed by TLC (petroleum ether:ethyl acetate=5:1). The mixture was cooled to 25° C., quenched with saturated aqueous ammonium chloride solution (20 mL) and extracted with ethyl acetate (30 mL×3). The combined organic layer was washed with saturated brine (50 mL×2) and dried over anhydrous sodium sulfate, followed by filtration. The filtrate was concentrated and the obtained crude product was purified by silica gel column chromatography (petroleum ether:ethyl acetate=50:1 to 20:1) to give the title compound (Compound 7) (5.00 g, 3.19 mmol, yield: 75.70%). $^1$H NMR (400 MHz, CDCl$_3$) δ 8.68 (s, 1H), 7.35 (s, 1H), 6.54 (s, 1H), 5.49 (q, J=9.2 Hz, 1H), 2.50 (s, 3H), 2.24-2.00 (m, 6H), 1.84-1.76 (m, 2H); LCMS (ESI) m/z: 263.0 (M+1).

Step 7:

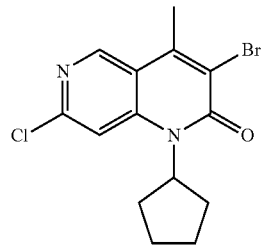 [SMILES: Cc1c(Br)c(=O)n(C2CCCC2)c2cc(Cl)ncc12]

Intermediate A

Sodium acetate (1.25 g, 15.22 mmol, 4.00 eq.) and liquid bromine (1.22 g, 7.61 mmol, 2.00 eq.) were sequentially added to a solution of 7-chloro-1-cyclopentyl-4-methyl-1,6-naphthyridin-2-one (Compound 7) (1.00 g, 3.81 mmol, 1.00 eq.) in acetic acid (20.00 mL). The reaction mixture was heated to 70° C. and stirred for 20 hours. The reaction mixture was concentrated and the obtained crude product was purified by silica gel column chromatography (petroleum ether:ethyl acetate=20:1) to give the title compound (Intermediate A) (1.10 g, 3.22 mmol, yield: 84.51%). $^1$H NMR (400 MHz, CDCl$_3$) δ 8.80 (s, 1H), 7.40 (s, 1H), 5.40-5.30 (m, 1H), 2.73 (s, 3H), 2.29-2.12 (m, 4H), 2.07-1.98 (m, 2H), 1.81-1.75 (m, 2H).

Step 8:

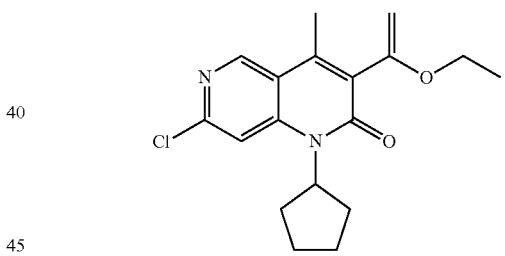

Tributyl(1-ethoxyvinyl)tin (580.01 mg, 1.61 mmol, 1.10 eq.) and Pd(PPh$_3$)$_4$ (168.71 mg 146.00 μmol, 0.10 eq.) were added to a solution of 3-bromo-7-chloro-1-cyclopentyl-4-methyl-1,6-naphthyridin-2-one (Compound 8) (500.00 mg, 1.46 mmol, 1.00 eq.) in toluene (5.00 mL) under nitrogen atmosphere. The reaction mixture was heated to 110° C. and stirred for 16 hours. The completion of the reaction was confirmed by LCMS. The reaction solution was concentrated and the obtained crude product was purified by silica gel column chromatography (petroleum ether:ethyl acetate=30:1) to give the title compound (Compound 9) (400.00 mg, 1.20 mmol, yield: 82.32%). $^1$H NMR (300 MHz, CD$_3$OD) δ 8.84 (s, 1H), 7.72 (s, 1H), 5.41-5.30 (m, 1H), 4.57 (d, J=2.4 Hz, 1H), 4.15 (d, J=2.4 Hz, 1H), 3.94 (q, J=7.2 Hz, 2H), 2.56 (s, 3H), 2.24-2.05 (m, 6H), 1.84-1.78 (m, 2H), 1.35 (t, J=6.8 Hz, 3H); LCMS (ESI) m/z: 333.1 (M+1).

Step 9:

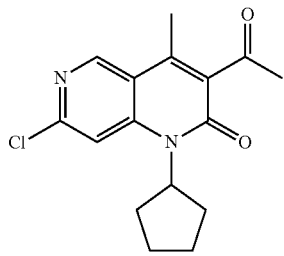 [SMILES: CC(=O)c1c(C)c2cnc(Cl)cc2n(C2CCCC2)c1=O]

Intermediate B

Trifluoroacetic acid (3.00 mL) was added to a solution of 7-chloro-1-cyclopentyl-3-(1-ethoxyvinyl)-4-methyl-1,6-naphthyridin-2-one (Compound 9) (400.00 mg, 1.20 mmol, 1.00 eq.) in dichloromethane (5.00 mL). The reaction mixture was stirred at 25° C. for 1 hour. The completion of the reaction was confirmed by TLC (petroleum ether:ethyl acetate=5:1) and LCMS. The reaction solution was concentrated, followed by addition of water (5 mL) and extraction with ethyl acetate (10 mL×3). The combined organic layer was washed with saturated brine (20 mL×2) and dried over anhydrous sodium sulfate, followed by filtration. The filtrate was concentrated and the obtained crude product was purified by silica gel column chromatography (petroleum ether:ethyl acetate=20:1 to 10:1) to give the title compound (Intermediate B) (300 mg, 984.35 µmol, yield: 81.90%). LCMS (ESI) m/z: 305.2 (M+1).

Example 1

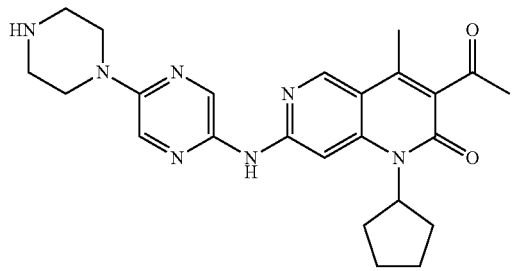 [SMILES: CC(=O)c1c(C)c2cnc(Nc3cnc(N4CCNCC4)cn3)cc2n(C2CCCC2)c1=O]

Step 1:

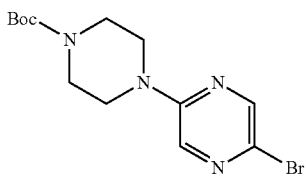 [SMILES: CC(C)(C)OC(=O)N1CCN(c2cnc(Br)cn2)CC1]

Tert-butyl piperazine-1-carboxylate (7.83 g, 42.04 mmol, 1.00 eq.) and potassium carbonate (8.72 g, 63.06 mmol, 1.50 eq.) were added to a solution of 2,5-dibromopyrazine (10.00 g, 42.04 mmol, 1.00 eq.) in 1-methylpyrrolidin-2-one (100.00 mL). The mixture was heated to 100° C. and stirred for 18 hours. The completion of the reaction was confirmed by TLC (petroleum ether:ethyl acetate=10:1). The reaction mixture was diluted with water (200 mL), and extracted with ethyl acetate (200 mL×2). The combined organic layer was dried over anhydrous sodium sulfate, followed by filtration. The filtrate was concentrated and the obtained crude product was purified by silica gel column chromatography (petroleum ether:ethyl acetate=20:1 to 5:1) to give the title compound (11.00 g, 32.05 mmol, yield: 76.24%). ¹H NMR (400 MHz, CDCl₃) δ 8.15 (d, J=1.38 Hz, 1H), 7.87 (d, J=1.38 Hz, 1H), 3.56 (m, 8H), 1.49 (s, 9H).

Step 2:

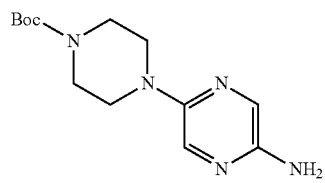

LiHMDS (1 M, 60.00 mL, 2.06 eq.) and Pd₂(dba)₃ (2.60 g, 2.84 mmol, 0.10 eq.) was added to a solution of tert-butyl 4-(5-bromopyrazin-2-yl)piperazine-1-carboxylate (10.00 g, 29.14 mmol, 1.00 eq.) and tri-tert-butylphosphonium tetrafluoroborate (2.54 g, 8.74 mmol, 0.30 eq.) in toluene (100.00 mL) under nitrogen atmosphere. The reaction mixture was heated to 65° C. and stirred for 16 hours. The completion of the reaction was confirmed by LCMS. The reaction mixture was quenched with water (50 mL) and extracted with ethyl acetate (100 mL×3). The combined organic layer was concentrated and the crude product was purified by preparative HPLC (alkaline) to give the title compound (5.00 g, 17.90 mmol, yield: 61.43%). LCMS (ESI) m/z: 280.1 (M+1).

Step 3:

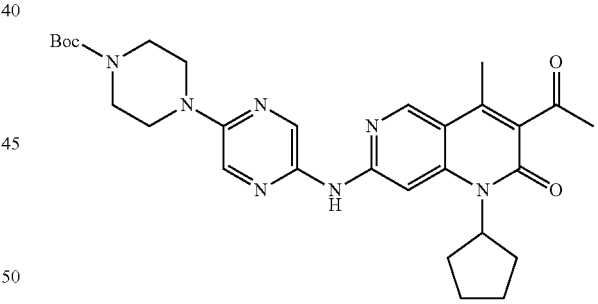

Xphos-Pd-G2 (25.82 mg, 32.81 µmol, 0.10 eq.) was added to a solution of 3-acetyl-7-chloro-1-cyclopentyl-4-methyl-1,6-naphthyridin-2-one (Intermediate B) (100.00 mg, 328.12 µmol, 1.00 eq.), 4-(5-aminopyrazin-2-yl)piperazine-1-carboxylic acid tert-butyl ester (137.48 mg, 492.17 µmol, 1.50 eq.) and potassium tert-butoxide (110.45 mg, 984.35 µmol, 3.00 eq.) in tetrahydrofuran (2.00 mL). The mixture was heated to 80° C. and stirred for 16 hours. The complete conversion of the starting materials was confirmed by TLC (petroleum ether:ethyl acetate=1:1). The reaction solution was cooled to room temperature and concentrated, and the crude product was purified by preparative TLC (petroleum ether:ethyl acetate=1:1) to give the title compound (40.00 mg, 73.04 µmol, yield: 22.26%).

Step 4:

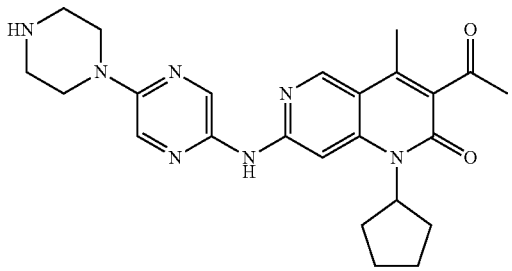 [SMILES: CC(=O)c1c(C)c2cnc(Nc3cnc(N4CCNCC4)cn3)cc2n(C2CCCC2)c1=O]

Trifluoroacetic acid (0.5 mL) was added to a solution of tert-butyl 4-(5-((3-acetyl-1-cyclopentyl-4-methyl-2-oxo-1,2-dihydro-1,6-naphthalen-7-yl)amino)pyrazine-2-yl)piperazine-1-carboxylate (60.00 mg, 109.56 μmol, 1.00 eq.) in dichloromethane (1.00 mL) at 25° C., and the mixture was stirred for 0.5 hour. The completion of the reaction was confirmed by LCMS. The reaction mixture was concentrated, and the obtained crude product was purified by preparative HPLC (hydrochloric acid) to give the hydrochloride salt of the title compound (22.78 mg, 50.90 μmol, yield: 46.46%). $^1$H NMR (400 MHz, CD$_3$OD) δ 8.78 (s, 1H), 8.27 (s, 1H), 8.19 (s, 1H), 7.30 (s, 1H), 5.44-5.32 (m, 1H), 3.93-3.88 (m, 4H), 3.44-3.38 (m, 4H), 2.51 (s, 3H), 2.40 (s, 3H), 2.31-2.16 (m, 4H), 2.08 (d, J=8.0 Hz, 2H), 1.82 (m, 2H); LCMS (ESI) m/z: 448.1 (M+1).

Example 2

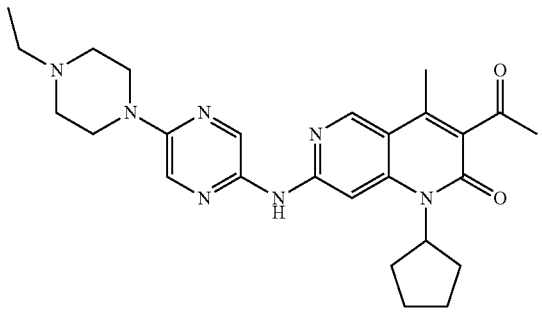 [SMILES: CCN1CCN(c2cnc(Nc3cc4c(cn3)c(C)c(C(C)=O)c(=O)n4C3CCCC3)cn2)CC1]

Acetaldehyde solution (553.66 mg, 5.03 mmol, 700.83 μL, 15.00 eq.) and sodium triacetoxyborohydride (213.11 mg, 1.01 mmol, 3.00 eq.) were added to a solution of 3-acetyl-1-cyclopentyl-4-methyl-7-[(5-piperazin-1-ylpyrazin-2-yl)amino]-1,6-naphthyridin-2-one (150.00 mg, 335.17 μmol, 1.00 eq.) in dichloroethane (2.00 mL) at 25° C. The mixture was stirred for 1 hour. About 26% of the title compound was detected by LCMS. The mixture was concentrated, and the obtained crude product was purified by preparative HPLC (alkaline) to give the title compound (14.35 mg, 27.71 μmol, yield: 8.27%, purity: 91.83%). $^1$H NMR (400 MHz, CDCl$_3$) δ 8.65 (s, 1H), 8.17 (d, J=1.3 Hz, 1H), 7.89-7.75 (m, 2H), 7.65 (s, 1H), 5.73 (quin, J=9.3 Hz, 1H), 3.60-3.48 (m, 4H), 2.65-2.58 (m, 4H), 2.55 (s, 3H), 2.49 (q, J=7.3 Hz, 2H), 2.40 (s, 3H), 2.29 (br dd, J=12.4, 7.3 Hz, 2H), 2.13 (br dd, J=7.9, 5.5 Hz, 2H), 2.02-1.95 (m, 2H), 1.82-1.73 (m, 2H), 1.15 (t, J=7.2 Hz, 3H); LCMS (ESI) m/z: 492.3 (M+1).

Example 3

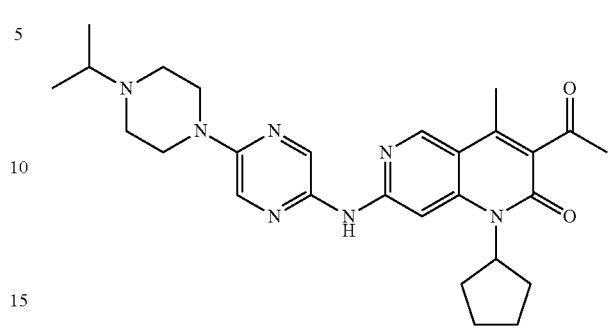

The synthesis of Example 3 is referred to as that of Example 2. $^1$H NMR (400 MHz, CDCl$_3$) δ 8.65 (s, 1H), 8.17 (d, J=1.3 Hz, 1H), 7.87-7.74 (m, 2H), 7.46 (s, 1H), 5.74 (quin, J=9.3 Hz, 1H), 3.63-3.43 (m, 4H), 2.77 (td, J=13.0, 6.5 Hz, 1H), 2.73-2.66 (m, 4H), 2.56 (s, 3H), 2.41 (s, 3H), 2.35-2.24 (m, 2H), 2.19-2.07 (m, 2H), 2.03-1.95 (m, 2H), 1.77 (br d, J=4.8 Hz, 2H), 1.11 (d, J=6.5 Hz, 6H); LCMS (ESI) m/z: 490.2 (M+1).

Example 4

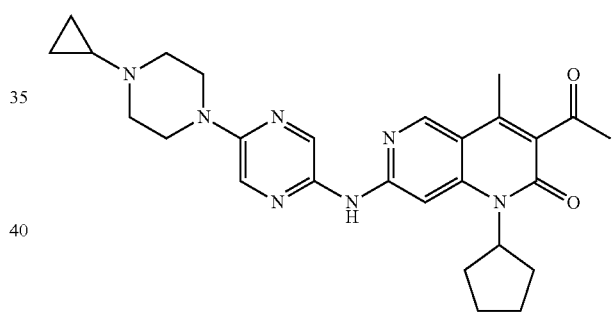

(1-ethoxycyclopropyloxy)trimethylsilane (292.12 mg, 1.68 mmol, 335.77 μL, 5.00 eq.) and sodium cyanoborohydride (63.19 mg, 1.01 mmol, 3.00 eq.) were added to a solution of 3-acetyl-1-cyclopentyl-4-methyl-7-[(5-piperazin-1-ylpyrazin-2-yl)amino]-1,6-naphthyridin-2-one (150.00 mg, 335.17 μmol, 1.00 eq.) in methanol (2.00 mL) at 25° C. The mixture was stirred at 25° C. for 1 hour. Incomplete conversion of the starting materials was confirmed by LCMS. The reaction mixture was heated to 60° C. and stirred for 18 hours. The title compound was detected by LCMS. The reaction mixture was concentrated, and the obtained crude product was purified by preparative HPLC (alkaline) to give the title compound (31.98 mg, 65.17 μmol, yield: 19.44%, purity: 99.37%). $^1$H NMR (400 MHz, CDCl$_3$) δ 8.66 (s, 1H), 8.17 (d, J=1.4 Hz, 1H), 7.84-7.77 (m, 2H), 7.44 (s, 1H), 5.74 (quin, J=9.3 Hz, 1H), 3.54-3.44 (m, 4H), 2.83-2.73 (m, 4H), 2.56 (s, 3H), 2.41 (s, 3H), 2.35-2.24 (m, 2H), 2.19-2.08 (m, 2H), 2.04-1.93 (m, 2H), 1.78 (br dd, J=10.3, 5.5 Hz, 2H), 0.56-0.45 (m, 4H); LCMS (ESI) m/z: 488.3 (M+1).

Example 5

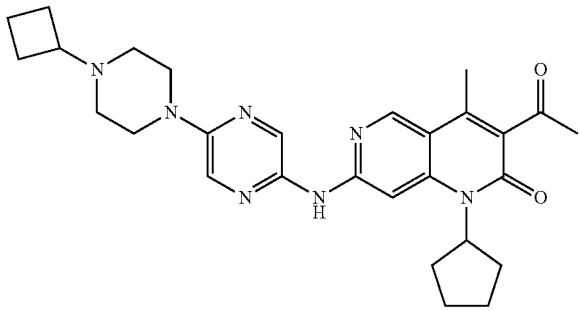 [SMILES: CC(=O)c1c(C)c2cnc(Nc3cnc(N4CCN(C5CCC5)CC4)cn3)cc2n(C2CCCC2)c1=O]

The synthesis of Example 5 is referred to as that of Example 2. ¹H NMR (400 MHz, CDCl₃) δ 8.65 (s, 1H), 8.17 (d, J=1.1 Hz, 1H), 7.88-7.73 (m, 2H), 7.65 (s, 1H), 5.73 (quin, J=9.3 Hz, 1H), 3.57-3.48 (m, 4H), 2.79 (quin, J=7.8 Hz, 1H), 2.55 (s, 3H), 2.51-2.44 (m, 4H), 2.40 (s, 3H), 2.35-2.23 (m, 2H), 2.18-2.04 (m, 4H), 2.02-1.86 (m, 6H), 1.83-1.70 (m, 2H); LCMS (ESI) m/z: 502.3 (M+1).

Example 6

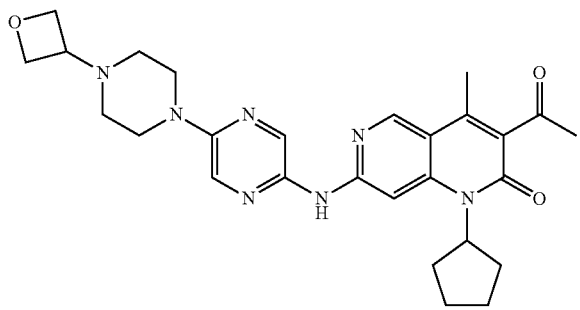 [SMILES: CC(=O)c1c(C)c2cnc(Nc3cnc(N4CCN(C5COC5)CC4)cn3)cc2n(C2CCCC2)c1=O]

The synthesis of Example 6 is referred to as that of Example 2. ¹H NMR (400 MHz, CDCl₃) δ 8.66 (s, 1H), 8.19 (d, J=1.1 Hz, 1H), 7.82 (s, 2H), 7.55 (s, 1H), 5.74 (quin, J=9.3 Hz, 1H), 4.70 (td, J=19.4, 6.4 Hz, 4H), 3.68-3.47 (m, 5H), 2.56 (s, 3H), 2.53-2.45 (m, 4H), 2.41 (s, 3H), 2.36-2.23 (m, 2H), 2.19-2.08 (m, 2H), 2.02-1.94 (m, 2H), 1.81-1.75 (m, 2H); LCMS (ESI) m/z: 504.2 (M+1)

Example 7

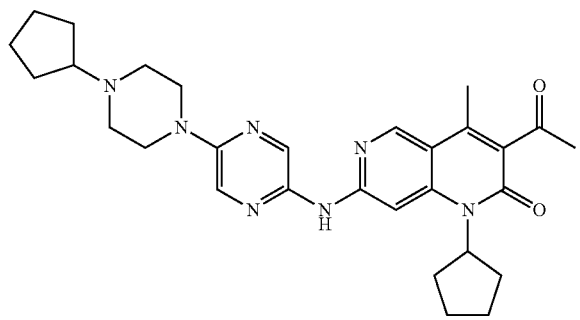 [SMILES: CC(=O)c1c(C)c2cnc(Nc3cnc(N4CCN(C5CCCC5)CC4)cn3)cc2n(C2CCCC2)c1=O]

The synthesis of Example 7 is referred to as that of Example 2. ¹H NMR (400 MHz, CDCl₃) δ 8.65 (s, 1H), 8.17 (d, J=1.4 Hz, 1H), 7.85-7.75 (m, 2H), 7.70-7.58 (m, 1H), 5.73 (t, J=9.3 Hz, 1H), 3.61-3.45 (m, 4H), 2.70-2.62 (m, 4H), 2.61-2.48 (m, 4H), 2.40 (s, 3H), 2.34-2.22 (m, 2H), 2.17-2.06 (m, 2H), 1.98-1.87 (m, 4H), 1.81-1.68 (m, 4H), 1.64-1.53 (m, 2H), 1.51-1.41 (m, 2H); LCMS (ESI) m/z: 516.3 (M+1)

Example 8

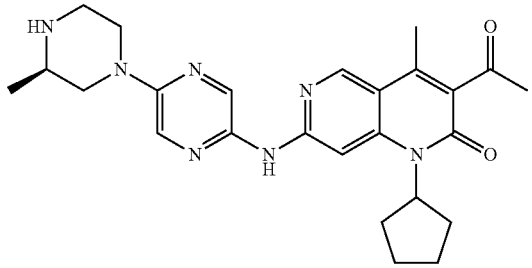 [SMILES: CC(=O)c1c(C)c2cnc(Nc3cnc(N4CCN[C@H](C)C4)cn3)cc2n(C2CCCC2)c1=O]

Step 1:

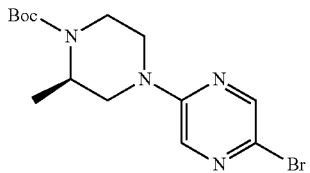 [SMILES: C[C@@H]1CN(c2cnc(Br)cn2)CCN1C(=O)OC(C)(C)C]

5-Dibromopyrazine (1.00 g, 4.20 mmol, 1.00 eq.) and potassium carbonate (871.51 mg, 6.30 mmol, 1.50 eq.) were added to a solution of (2R)-tert-butyl 2-methylpiperazine-1-carboxylate (841.94 mg, 4.20 mmol, 1.00 eq.) in 1-methylpyrrolidin-2-one (10.00 mL). The mixture was heated to 100° C. and stirred for 18 hours. The completion of the reaction was confirmed by LCMS. The reaction mixture was cooled to room temperature, diluted with water (100 mL) and extracted with ethyl acetate (50 mL×3). The combined organic phase was washed with water (50 mL×3) and brine (50 mL) and concentrated. The obtained crude product was purified by silica gel column chromatography (petroleum ether:ethyl acetate=20:1) to give the title compound (900.00 mg, 2.52 mmol, yield: 59.98%). ¹H NMR (400 MHz, CDCl₃) δ 8.12 (d, J=1.4 Hz, 1H), 7.84 (d, J=1.5 Hz, 1H), 4.35 (br s, 1H), 4.09-4.02 (m, 1H), 3.96 (td, J=13.2, 2.0 Hz, 2H), 3.32-3.21 (m, 2H), 3.05 (dt, J=11.9, 3.8 Hz, 1H), 1.49 (s, 9H), 1.19 (d, J=6.7 Hz, 3H).

Step 2:

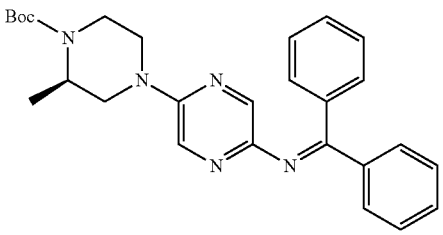 [SMILES: C[C@@H]1CN(c2cnc(N=C(c3ccccc3)c3ccccc3)cn2)CCN1C(=O)OC(C)(C)C]

Diphenylmethylimine (502.37 mg, 2.77 mmol, 465.16 µL, 1.00 eq.), cesium carbonate (1.64 g, 5.04 mmol, 2.00 eq.), Pd(OAc)$_2$ (56.56 mg, 252.00 µmol, 0.10 eq.) and BINAP (313.73 mg, 504.00 µmol, 0.20 eq.) were added to a solution of (2R)-tert-butyl 4-(5-bromopyrazin-2-yl)-2-methyl-piperazine-1-carboxylate (900.00 mg, 2.52 mmol, 1.00 eq.) in 1,4-dioxane (10.00 mL) under nitrogen atmosphere. The mixture was heated to 100° C. and stirred for 18 hours. The completion of the reaction was confirmed by LCMS. The reaction mixture was cooled to room temperature and then diluted with dichloromethane (10 mL), followed by filtration. The filtrate was concentrated and the obtained crude product was purified by silica gel column chromatography (petroleum ether:ethyl acetate=40:1 to 10:1) to give the title compound (850.00 mg, 1.86 mmol, yield: 73.72%). $^1$H NMR (400 MHz, CDCl$_3$) δ 7.82-7.77 (m, 3H), 7.55 (d, J=1.4 Hz, 1H), 7.51-7.47 (m, 1H), 7.44-7.38 (m, 2H), 7.36-7.30 (m, 3H), 7.21-7.15 (m, 2H), 4.32 (br s, 1H), 4.01-3.83 (m, 3H), 3.26-3.13 (m, 2H), 2.93 (dt, J=12.0, 3.7 Hz, 1H), 1.49 (s, 9H), 1.18 (d, J=6.8 Hz, 3H).

Step 3:

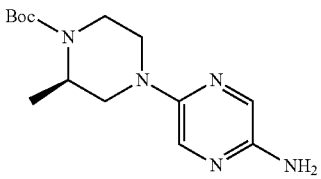 [SMILES: C[C@@H]1CN(c2cnc(N)cn2)CCN1C(=O)OC(C)(C)C]

Sodium acetate (183.09 mg, 2.23 mmol) and hydroxylamine hydrochloride (232.65 mg, 3.35 mmol, 1.80 eq.) were added to a solution of (2R)-tert-butyl 4-(5-(diphenylmethyleneamino)pyrazin-2-yl)-2-methyl-piperazine-1-carboxylate (850.00 mg, 1.86 mmol, 1.00 eq.) in methanol (10.00 mL). The mixture was stirred at 20° C. for 30 minutes. The completion of the reaction was confirmed by LCMS. The reaction mixture was concentrated and the obtained crude material was purified by silica gel column chromatography (petroleum ether:ethyl acetate=10:1 to 3:1) to give the title compound (160.00 mg, 545.40 µmol, yield: 29.32%). $^1$H NMR (400 MHz, CDCl$_3$) δ 7.69 (d, J=1.3 Hz, 1H), 7.64 (d, J=1.3 Hz, 1H), 4.36 (br s, 1H), 4.14-4.05 (m, 2H), 3.96 (br d, J=13.4 Hz, 1H), 3.86 (br d, J=12.2 Hz, 1H), 3.73 (br d, J=12.3 Hz, 1H), 3.24 (dt, J=12.7, 3.5 Hz, 1H), 3.00 (dd, J=12.4, 4.0 Hz, 1H), 2.79 (dt, J=12.0, 3.6 Hz, 1H), 1.49 (s, 9H), 1.25 (d, J=7.0 Hz, 3H).

Step 4:

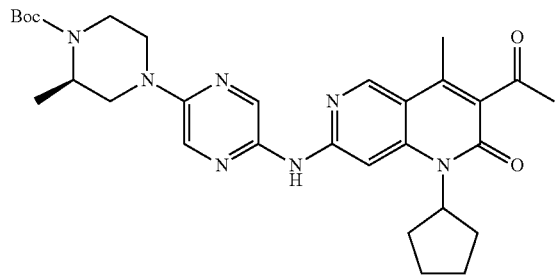 [SMILES: CC(=O)c1c(C)c2cnc(Nc3cnc(N4CCN(C(=O)OC(C)(C)C)[C@H](C)C4)cn3)cc2n(C2CCCC2)c1=O]

Xphos-Pd-G3 (46.17 mg, 54.54 µmol, 0.10 eq.) and potassium t-butoxide (122.40 mg, 1.09 mmol, 2.00 eq.) were added to a solution of (2R)-tert-butyl 4-(5-aminopyrazin-2-yl)-2-methyl-piperazine-1-carboxylate (160.00 mg, 545.40 µmol, 1.00 eq.) and 3-acetyl-7-chloro-1-cyclopentyl-4-methyl-1,6-naphthyridin-2-one (Intermediate B) (166.22 mg, 545.40 µmol, 1.00 eq.) in tetrahydrofuran (2.00 mL). The mixture was heated to 70° C. and stirred for 18 hours. The completion of the reaction was confirmed by LCMS. The reaction mixture was cooled to room temperature and diluted with dichloromethane (5 mL), filtered and the filtrate was concentrated. The obtained crude product was purified by preparative TLC (petroleum ether:ethyl acetate=1:1) to give the title compound (200.00 mg, 313.35 µmol, yield: 57.45%, purity: 88%). LCMS (ESI) m/z: 562.2 (M+1).

Step 5:

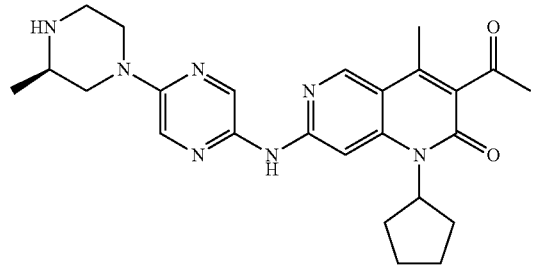 [SMILES: CC(=O)c1c(C)c2cnc(Nc3cnc(N4CCN[C@H](C)C4)cn3)cc2n(C2CCCC2)c1=O]

Trifluoroacetic acid (1.00 mL) was added to a solution of (2R)-tert-butyl 4-(5-((3-acetyl-1-cyclopentyl-4-methyl-2-oxo-1,6-naphthyridin-7-yl)amino)pyrazine-2-yl-2-methyl-piperazine-1-carboxylate (200.00 mg, 313.35 µmol, 1.00 eq.) in dichloromethane (2.00 mL) at 20° C. and stirred for 15 minutes. The completion of the reaction was confirmed by LCMS. The reaction mixture was concentrated to dryness, and the obtained crude product was purified by preparative HPLC (hydrochloric acid) to give the hydrochloride salt of the title compound (66.91 mg, 123.94 µmol, yield: 39.55%, purity: 99%). $^1$H NMR (400 MHz, CD$_3$OD) δ 8.76 (s, 1H), 8.24 (d, J=1.1 Hz, 1H), 8.20 (s, 1H), 7.27 (s, 1H), 5.36 (quin, J=8.7 Hz, 1H), 4.50-4.39 (m, 2H), 3.56-3.45 (m, 2H), 3.31-3.21 (m, 2H), 3.10 (dd, J=14.1, 10.8 Hz, 1H), 2.49 (s, 3H), 2.38 (s, 3H), 2.29-2.12 (m, 4H), 2.10-1.99 (m, 2H), 1.87-1.72 (m, 2H), 1.45 (d, J=6.6 Hz, 3H); LCMS (ESI) m/z: 462.1 (M+1); SFC (AD-3S_4_40_3ML column: Chiralpak AD-3 100×4.6 mm ID, 3 µm; mobile phase A: 40% isopropanol (containing 0.05% diethylamine); mobile phase B: CO$_2$; flow rate: 3 mL/min; wavelength: 280 nm): RT=2.834 min.

Example 9

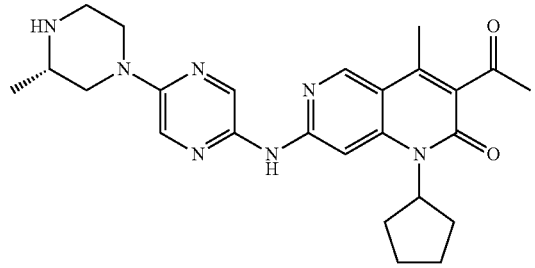 [SMILES: CC(=O)c1c(C)c2cnc(Nc3cnc(N4CCN[C@@H](C)C4)cn3)cc2n(C2CCCC2)c1=O]

The starting material of Example 9 is (2S)-tert-butyl 2-methylpiperazine-1-carboxylate, the synthesis method of which is referred to as that of Example 8. $^1$H NMR (400 MHz, CD$_3$OD) δ 8.76 (s, 1H), 8.24 (d, J=1.3 Hz, 1H), 8.20

(d, J=1.3 Hz, 1H), 7.26 (s, 1H), 5.37 (quin, J=8.7 Hz, 1H), 4.52-4.38 (m, 2H), 3.58-3.44 (m, 2H), 3.36-3.31 (m, 2H), 3.09 (dd, J=14.1, 10.7 Hz, 1H), 2.49 (s, 3H), 2.38 (s, 3H), 2.30-2.12 (m, 4H), 2.10-1.99 (m, 2H), 1.86-1.74 (m, 2H), 1.45 (d, J=6.5 Hz, 3H); LCMS (ESI) m/z: 462.1 (M+1); SFC (AD-3S_4_40_3ML column: Chiralpak AD-3 100×4.6 mm ID, 3 μm; mobile phase A: 40% isopropanol (containing 0.05% diethylamine); mobile phase B: $CO_2$; flow rate: 3 mL/min; wavelength: 280 nm): RT=3.284 min.

Example 10

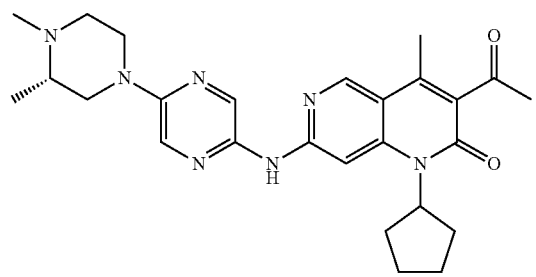 [SMILES: CC(=O)c1c(C)c2cnc(Nc3cnc(N4CCN(C)[C@@H](C)C4)cn3)cc2n(C2CCCC2)c1=O]

Formaldehyde solution (351.68 mg, 4.33 mmol, 322.64 μL, 10.00 eq.), acetic acid (500.00 μL) and palladium on carbon (wetted with water) (100.00 mg) were added to a solution of 3-acetyl-1-cyclopentyl-4-methyl-7-[[5-[(3S)-3-methylpiperazin-1-yl]pyrazin-2-yl]amino]-1,6-naphthyridin-2-one (200.00 mg, 433.31 μmol, 1.00 eq.) in methanol (20.00 mL). The reaction flask was purged three times with nitrogen and hydrogen sequentially. The hydrogen pressure was maintained at 50 Psi, and the reaction solution was heated to 50° C. with stirring for 3 hours. The completion of reaction was confirmed by LCMS. The reaction solution was filtered and the filtrate was concentrated. The obtained crude product was purified by preparative HPLC (alkaline) to give the title compound (42.66 mg, 88.31 μmole, yield: 20.38%, purity: 98.45%). $^1$H NMR (400 MHz, CDCl$_3$) δ 8.65 (s, 1H), 8.16 (s, 1H), 7.81-7.79 (m, 3H), 5.71 (quin, J=9.3 Hz, 1H), 3.98-3.93 (m, 2H), 3.07 (dt, J=11.4, 3.0 Hz, 1H), 2.92 (td, J=11.4, 3.2 Hz, 1H), 2.70-2.6 (m, 1H), 2.56 (s, 3H), 2.39 (s, 3H), 2.38-2.37 (m, 1H), 2.35 (s, 3H), 2.31-2.20 (m, 3H), 2.17-2.04 (m, 3H), 2.01-1.93 (m, 2H), 1.84-1.71 (m, 2H), 1.17 (d, J=5.6 Hz, 3H); LCMS (ESI) m/z: 476.3 (M+1).

Example 11

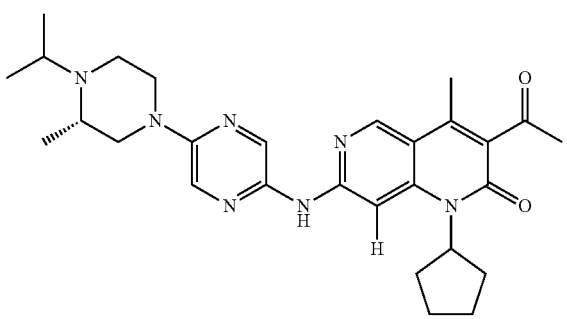 [SMILES: CC(=O)c1c(C)c2cnc(Nc3cnc(N4CCN(C(C)C)[C@@H](C)C4)cn3)cc2n(C2CCCC2)c1=O]

Potassium carbonate (149.72 mg, 1.08 mmol, 5.00 eq.) and 2-iodopropane (736.60 mg, 4.33 mmol, 433.29 μL, 20.00 eq.) were added to a solution of 3-acetyl-1-cyclopentyl-4-methyl-7-[[5-[(3S)-3-methylpiperazin-1-yl]pyrazin-2-yl]amino]-1,6-naphthyridin-2-one (100.00 mg, 216.66 μmol, 1.00 eq.) in acetonitrile (10.00 mL). The reaction mixture was heated to 80° C. and stirred for 18 hours. About 13.5% of the starting materials remained and about 75.5% of the title compound formed was detected by LCMS. The reaction mixture was cooled to 20° C., followed by filtration. The filtrate was concentrated and the obtained crude product was purified by preparative HPLC (alkaline) to give the title compound (9.00 mg, 17.87 μmol, yield: 8.25%). $^1$H NMR (400 MHz, CDCl$_3$) δ 8.65 (s, 1H), 8.16 (d, J=1.4 Hz, 1H), 7.81 (d, J=1.3 Hz, 1H), 7.77 (s, 1H), 7.40 (s, 1H), 5.74 (quin, J=9.3 Hz, 1H), 3.96-3.89 (m, 2H), 3.33 (spt, J=6.5 Hz, 1H), 3.06 (dt, J=11.4, 3.0 Hz, 1H), 2.92 (td, J=11.4, 3.2 Hz, 1H), 2.85-2.70 (m, 2H), 2.56 (s, 3H), 2.49-2.47 (m, 1H), 2.41 (s, 3H), 2.35-2.24 (m, 2H), 2.19-2.07 (m, 2H), 2.03-1.93 (m, 2H), 1.84-1.75 (m, 2H), 1.17 (dd, J=6.2, 4.2 Hz, 6H), 0.93 (d, J=6.4 Hz, 3H); LCMS (ESI) m/z: 504.3 (M+1).

Example 12

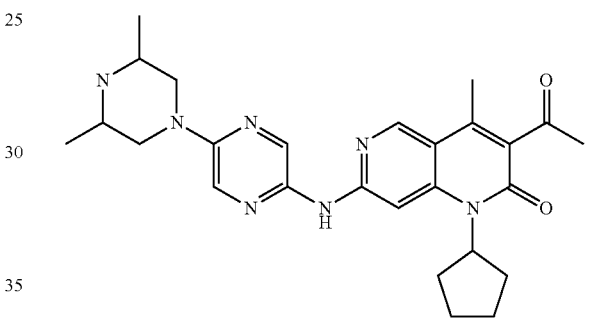

The synthesis of Example 12 is referred to as that of Example 1 to give the hydrochloride salt of the title compound. $^1$HNMR (400 MHz, CD$_3$OD) δ 8.77 (s, 1H), 8.26 (d, J=1.2 Hz, 1H), 8.24 (d, J=1.2 Hz, 1H), 7.27 (s, 1H), 5.44-5.35 (m, 1H), 4.58-4.54 (m, 2H), 3.55-5.45 (m, 2H), 3.00-2.93 (m, 2H), 2.51 (s, 3H), 2.40 (s, 3H), 2.30-2.15 (m, 4H), 2.10-2.05 (m, 2H), 1.84-1.78 (m, 2H), 1.46 (d, J=7.2 Hz, 6H); LCMS (ESI) m/z: 476.3 (M+1).

Example 13

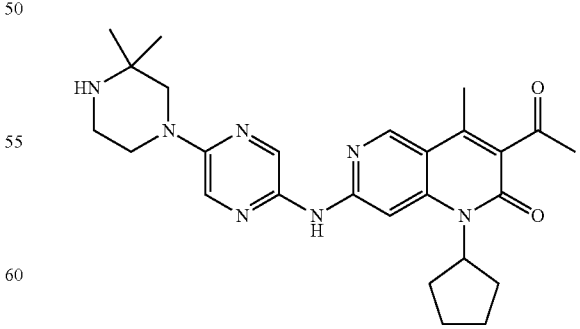

The synthesis of Example 13 is referred to as that of Example 1 to give the hydrochloride salt of the title compound. $^1$H NMR (400 MHz, CD$_3$OD) δ 8.76 (s, 1H), 8.23 (d, J=8.9 Hz, 2H), 7.26 (s, 1H), 5.43-5.29 (m, 1H), 3.99-3.83

(m, 2H), 3.76 (s, 2H), 3.50-3.39 (m, 2H), 2.53-2.46 (m, 3H), 2.39 (s, 3H), 2.29-2.13 (m, 4H), 2.11-2.01 (m, 2H), 1.82 (br d, J=5.9 Hz, 2H), 1.51 (s, 6H); LCMS (ESI) m/z: 476.2 (M+1).

Example 14

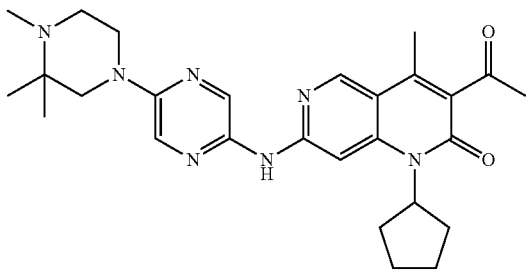 [SMILES: CC(=O)c1c(C)c2cnc(Nc3cnc(N4CCN(C)C(C)(C)C4)cn3)cc2n(C2CCCC2)c1=O]

Sodium triacetoxyborohydride (98.72 mg, 465.77 μmol, 2.50 eq.) was added to a solution of 3-acetyl-1-cyclopentyl-7-[[5-(3,3-dimethylpiperazin-1-yl)pyrazin-2-yl]amino]-4-methyl-1,6-naphthyridin-2-one (100.00 mg, 186.31 μmol, 1.00 eq.), formaldehyde solution (27.97 mg, 931.55 μmol, 25.66 μL, 5.00 eq.) and acetic acid (44.75 mg, 745.24 μmol, 42.62 μL, 4.00 eq.) in dichloroethane (1.00 mL). The reaction solution was heated to 60° C. and stirred for 16 hours. The completion of the reaction was confirmed by LCMS. The reaction solution was concentrated, and a saturated aqueous solution of sodium bicarbonate was added dropwise to the obtained residue to adjust pH to 9. The obtained aqueous phase was extracted with dichloromethane (5 mL×2). The combined organic phase was dried over anhydrous sodium sulfate and filtered, the filtrate was concentrated and the obtained crude product was purified by preparative HPLC (alkaline) to give the title compound (31.00 mg, 61.56 μmol, yield: 33.04%, purity: 97.229%). $^1$H NMR (400 MHz, CDCl$_3$) δ 8.64 (s, 1H), 8.14 (s, 1H), 7.80 (s, 1H), 7.73 (s, 1H), 7.53 (s, 1H), 5.84-5.59 (m, 1H), 3.62-3.44 (m, 2H), 3.27 (s, 2H), 2.68 (br t, J=5.0 Hz, 2H), 2.55 (s, 3H), 2.39 (s, 3H), 2.29 (s, 3H), 2.11 (br s, 2H), 1.97 (br d, J=5.4 Hz, 2H), 1.78 (br d, J=5.8 Hz, 4H), 1.10 (s, 6H); LCMS (ESI) m/z: 490.2 (M+1).

Example 15

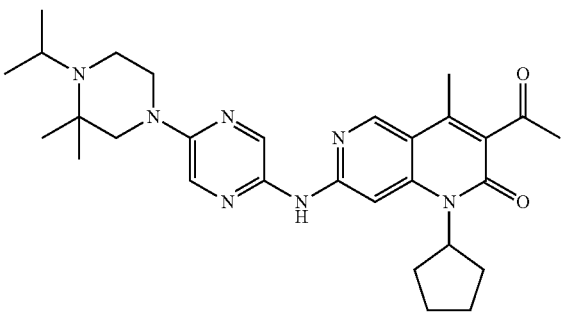 [SMILES: CC(=O)c1c(C)c2cnc(Nc3cnc(N4CCN(C(C)C)C(C)(C)C4)cn3)cc2n(C2CCCC2)c1=O]

The synthesis of Example 15 is referred to as that of Example 11. $^1$H NMR (400 MHz, CDCl$_3$) δ 8.64 (s, 1H), 8.12 (d, J=1.3 Hz, 1H), 7.79 (d, J=1.3 Hz, 1H), 7.70 (s, 1H), 7.44 (s, 1H), 5.86-5.63 (m, 1H), 3.49 (br s, 2H), 3.39-3.28 (m, 1H), 3.23 (br s, 2H), 2.82-2.69 (m, 2H), 2.55 (s, 3H), 2.39 (s, 3H), 2.34-2.20 (m, 2H), 2.17-2.05 (m, 2H), 2.03-1.91 (m, 2H), 1.76 (br dd, J=10.4, 5.6 Hz, 2H), 1.17 (s, 6H), 1.03 (br d, J=6.4 Hz, 6H); LCMS (ESI) m/z: 518.3 (M+1).

Example 16

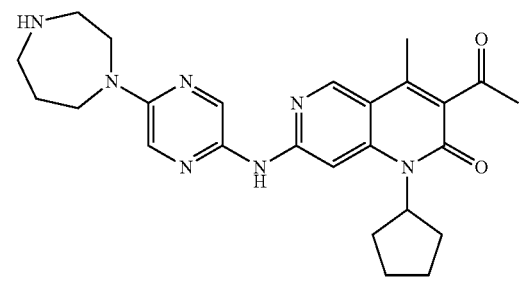 [SMILES: CC(=O)c1c(C)c2cnc(Nc3cnc(N4CCCNCC4)cn3)cc2n(C2CCCC2)c1=O]

The synthesis of Example 16 is referred to as that of Example 1 to give the hydrochloride salt of the title compound. $^1$H NMR (400 MHz, CD$_3$OD) δ 8.75 (s, 1H), 8.20 (s, 1H), 8.02 (s, 1H), 7.27 (s, 1H), 5.45-5.20 (m, 1H), 4.15-3.97 (m, 2H), 3.81 (br t, J=5.8 Hz, 2H), 3.44 (br d, J=4.4 Hz, 2H), 3.39-3.33 (m, 2H), 2.48 (s, 3H), 2.37 (s, 3H), 2.31-2.13 (m, 6H), 2.05 (br d, J=8.8 Hz, 2H), 1.79 (br s, 2H); LCMS (ESI) m/z: 462.2 (M+1).

Example 17

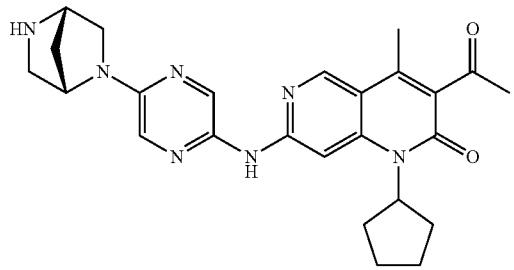 [SMILES: CC(=O)c1c(C)c2cnc(Nc3cnc(N4C[C@@H]5C[C@H]4CN5)cn3)cc2n(C2CCCC2)c1=O]

The synthesis of Example 17 is referred to as that of Example 1 to give the hydrochloride salt of the title compound. $^1$H NMR (400 MHz, CD$_3$OD) δ 8.74 (s, 1H), 8.21 (s, 1H), 7.90 (s, 1H), 7.26 (s, 1H), 5.35 (t, J=8.3 Hz, 1H), 5.04 (br. s., 1H), 4.61 (s, 1H), 3.86-3.77 (m, 1H), 3.77-3.69 (m, 1H), 3.49-3.39 (m, 2H), 2.49 (s, 3H), 2.38 (s, 3H), 2.32 (d, J=11.2 Hz, 2H), 2.25-2.10 (m, 5H), 2.05 (d, J=9.3 Hz, 2H), 1.80 (br. s., 2H); LCMS (ESI) m/z: 460.3 (M+1).

Example 18

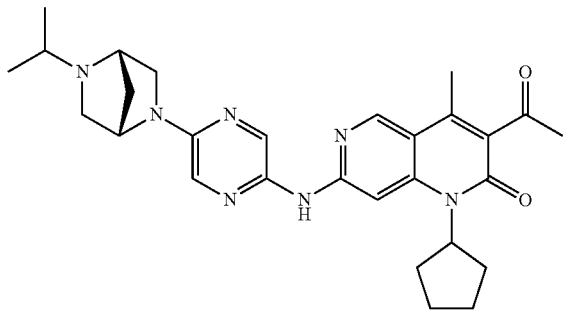 [SMILES: CC(=O)c1c(C)c2cnc(Nc3cnc(N4C[C@@H]5C[C@H]4CN5C(C)C)cn3)cc2n(C2CCCC2)c1=O]

The synthesis of Example 18 is referred to as that of Example 11 to give the hydrochloride salt of the title compound. $^1$H NMR (400 MHz, CD$_3$OD) δ 8.74 (d, J=7.9 Hz, 1H), 8.20 (d, J=4.1 Hz, 1H), 7.94-7.87 (m, 1H), 7.26 (d, J=4.6 Hz, 1H), 5.44-5.27 (m, 1H), 5.03 (br s, 1H), 4.82-4.72 (m, 1H), 4.00-3.88 (m, 1H), 3.85-3.67 (m, 2H), 3.65-3.38 (m, 2H), 2.49 (s, 3H), 2.38 (s, 3H), 2.36-2.25 (m, 2H), 2.25-2.11 (m, 4H), 2.05 (br d, J=8.9 Hz, 2H), 1.80 (br s, 2H), 1.51 (d, J=6.3 Hz, 2H), 1.46 (br d, J=5.8 Hz, 1H), 1.43-1.35 (m, 1H), 1.39 (br d, J=6.3 Hz, 2H); LCMS (ESI) m/z: 502.2 (M+1).

Example 19

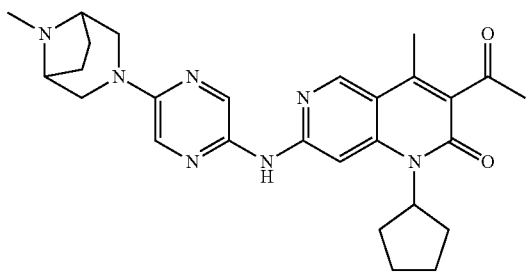 [SMILES: CC(=O)c1c(C)c2cnc(Nc3cnc(N4CC5CCC(C4)N5C)cn3)cc2n(C2CCCC2)c1=O]

The synthesis of Example 19 is referred to as that of Example 1 and Example 2 to give the hydrochloride salt of the title compound. $^1$H NMR (400 MHz, CD$_3$OD) δ 8.77 (s, 1H), 8.25 (s, 1H), 8.16-8.03 (m, 1H), 7.30 (s, 1H), 5.44-5.26 (m, 1H), 4.31 (br d, J=13.2 Hz, 2H), 4.21-4.06 (m, 2H), 3.70-3.35 (m, 2H), 2.93 (s, 3H), 2.55-2.45 (m, 3H), 2.38 (s, 3H), 2.37-1.92 (m, 10H), 1.80 (br s, 2H); LCMS (ESI) m/z: 488.1 (M+1).

Example 20

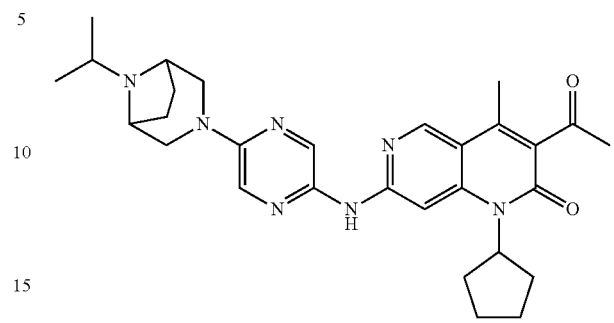

The synthesis of Example 20 is referred to as that of Example 11 to give the hydrochloride salt of the title compound. $^1$H NMR (400 MHz, CD$_3$OD) δ 8.76 (s, 1H), 8.31-8.20 (m, 1H), 8.14-8.05 (m, 1H), 7.27 (s, 1H), 5.37 (br t, J=8.5 Hz, 1H), 4.54-4.35 (m, 2H), 4.34-4.04 (m, 2H), 3.67-3.45 (m, 2H), 3.37 (td, J=12.6, 6.4 Hz, 1H), 2.54-2.45 (m, 3H), 2.38 (s, 3H), 2.34-2.26 (m, 2H), 2.23 (br d, J=10.8 Hz, 2H), 2.18 (br d, J=7.5 Hz, 2H), 2.14-2.08 (m, 2H), 2.07-1.98 (m, 2H), 1.86-1.73 (m, 1H), 1.80 (br s, 1H), 1.51 (d, J=6.4 Hz, 6H); LCMS (ESI) m/z: 516.2 (M+1).

Example 21

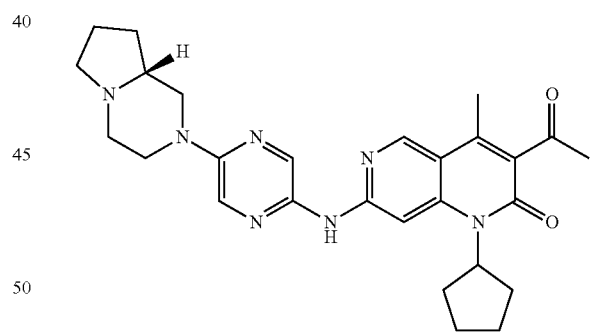

The synthesis of Example 21 is referred to as that of Example 1 to give the trifluoroacetate of the title compound. $^1$HNMR (400 MHz, CD$_3$OD) δ 8.71 (s, 1H), 8.24 (s, 1H), 8.07 (br s, 1H), 7.36 (s, 1H), 5.38 (quin, J=8.7 Hz, 1H), 4.92-4.47 (m, 2H), 4.20-3.58 (m, 5H), 3.31-3.01 (m, 2H), 2.50 (s, 3H), 2.37 (s, 3H), 2.32-2.13 (m, 6H), 2.09-2.01 (m, 2H), 1.81 (br d, J=5.9 Hz, 2H); LCMS (ESI) m/z: 488.2 (M+1).

Example 22

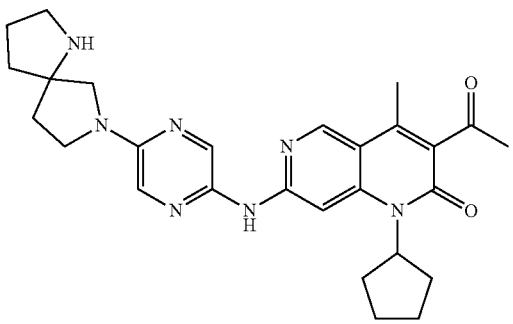 [SMILES: CC(=O)c1c(C)c2cnc(Nc3cnc(N4CCC5(CCCN5)C4)cn3)cc2n(C2CCCC2)c1=O]

Step 1:

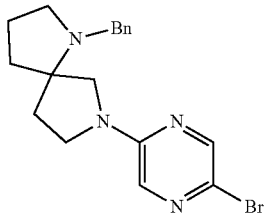 [SMILES: Brc1cnc(N2CCC3(CCCN3Cc3ccccc3)C2)cn1]

1-Benzyl-1,7-diazaspiro[4,4]decane (908.55 mg, 4.20 mmol, 1.00 eq.) and potassium carbonate (870.72 mg, 6.30 mmol, 1.50 eq.) were added to a solution of 2,5-dibromopyrazine (1.00 g, 4.20 mmol, 1.00 eq.) in 1-methylpyrrolidone (10.00 mL). The reaction mixture was heated to 100° C. and stirred for 16 hours. The completion of the reaction was confirmed by LCMS. Water (15 mL) was added to the reaction mixture, followed by extraction with ethyl acetate (30 mL×3). The combined organic phase was washed with water (20 mL×4) and dried over anhydrous sodium sulfate, followed by filtration. The filtrate was concentrated and the obtained crude product was purified by silica gel column chromatography (petroleum ether:ethyl acetate=20:1 to 10:1) to give the title compound (952.00 mg, 2.37 mmol, yield: 56.47%, purity: 93%). $^1$H NMR (400 MHz, CDCl$_3$) δ 8.04 (d, J=1.2 Hz, 1H), 7.63-7.51 (m, 1H), 7.29-7.20 (m, 4H), 7.18-7.13 (m, 1H), 3.68-3.53 (m, 3H), 3.52-3.32 (m, 2H), 3.29-3.18 (m, 1H), 2.72-2.55 (m, 2H), 2.28-2.14 (m, 1H), 1.94-1.68 (m, 5H); LCMS (ESI) m/z: 375.0 (M+1).

Step 2:

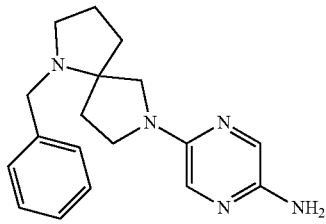 [SMILES: Nc1cnc(N2CCC3(CCCN3Cc3ccccc3)C2)cn1]

LiHMDS (1 M, 5.36 mL, 2.50 eq.), Pd$_2$(dba)$_3$ (196.25 mg, 214.31 μmol, 0.10 eq.) and tri-tert-butylphosphine tetrafluoroborate (186.53 mg, 642.93 μmol, 0.30 eq.) were added to a solution of 1-benzyl-7-(5-bromopyrazin-2-yl)-diazaspiro[4,4]decane (800.00 mg, 2.14 mmol, 1.00 eq.) in toluene (10.00 mL) under nitrogen atmosphere. The reaction mixture was heated to 65° C. and stirred for 16 hours. The completion of the reaction was confirmed by TLC (petroleum ether:ethyl acetate=10:1). The reaction mixture was concentrated, and the obtained residue was diluted with ethyl acetate (10 mL). The organic phase was added to a saturated aqueous solution of potassium fluoride (10 mL), and the obtained mixture was stirred at 30° C. for 16 hours. The above mixture was extracted with ethyl acetate (10 mL×3). The organic phase was concentrated, and the obtained crude product was purified by silica gel column chromatography (petroleum ether:ethyl acetate=10:1 to dichloromethane:methanol=20:1) to give the title compound (700.00 mg, crude product). LCMS (ESI) m/z: 310.3 (M+1).

Step 3:

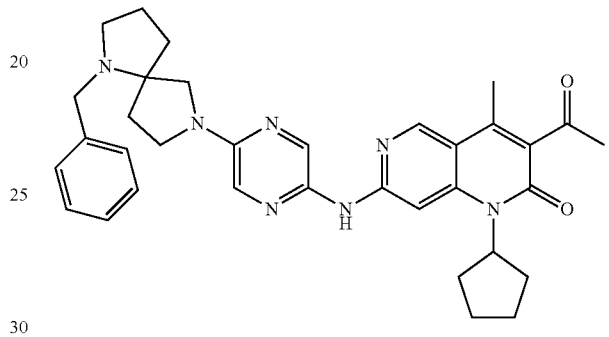

3-Acetyl-7-chloro-1-cyclopentyl-4-methyl-1,6-naphthyridin-2-one (Intermediate B) (472.80 mg, 1.55 mmol, 1.20 eq.), potassium tert-butoxide (435.19 mg, 3.88 mmol, 3.00 eq.) and Xphos-Pd-G3 (191.01 mg, 258.56 μmol, 0.20 eq.) were added to a solution of 5-(1-benzyl-1,7-diazaspiro[4,4]decane-7-yl)pyrazin-2-amine (400.00 mg, 1.29 mmol, 1.00 eq.) in THF (5.00 mL). The reaction mixture was heated to 70° C. and stirred for 16 hours. The completion of the reaction was confirmed by LCMS. The reaction mixture was concentrated and the obtained crude product was purified by preparative TLC (petroleum ether:ethyl acetate=3:1) to give the title compound (110.00 mg, crude product). LCMS (ESI) m/z: 578.2 (M+1).

Step 4:

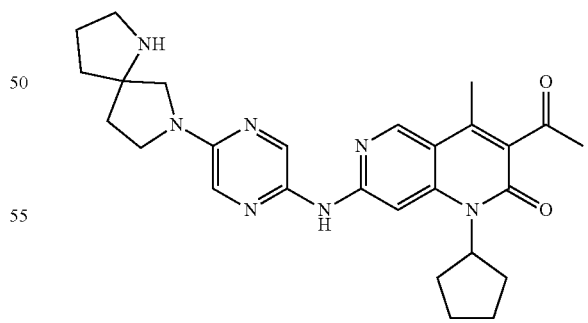

Palladium on carbon (5.00 mg) was added to a mixture of 3-acetyl-7-[[5-(1-benzyl-1,7-diazaspiro[4,4]decane-7-yl)pyrazin-2-yl]amino]-1-cyclopentyl-4-methyl-1,6-naphthyridin-2-one (5.00 mg, 8.65 μmol, 1.00 eq.) in tetrahydrofuran (2.00 mL) and methanol (2.00 mL). Hydrogen pressure was maintained at 15 Psi and the reaction mixture was stirred at 30° C. for 32 hours. The completion of the reaction was confirmed by LCMS. The reaction solution was filtered and the filtrate was concentrated. The obtained crude product was purified by preparative HPLC (hydrochloric acid) to give the hydrochloride salt of the title compound (550.00 µg, 1.05 µmol, yield: 12.13%, purity: 93%). $^1$H NMR (400 MHz, CD$_3$OD) δ 8.74 (s, 1H), 8.28-8.14 (m, 1H), 7.93-7.84 (m, 1H), 7.31-7.14 (m, 1H), 5.48-5.37 (m, 1H), 4.08-4.06 (m, 1H), 4.17-4.01 (m, 1H), 3.93-3.77 (m, 2H), 3.73-3.63 (m, 1H), 3.55-3.50 (m, 1H), 2.96-2.88 (m, 1H), 2.51 (s, 5H), 2.43-2.36 (m, 3H), 2.31-2.13 (m, 8H), 2.11-2.01 (m, 2H), 1.89-1.78 (m, 2H); LCMS (ESI) m/z: 488.2 (M+1).

Example 23

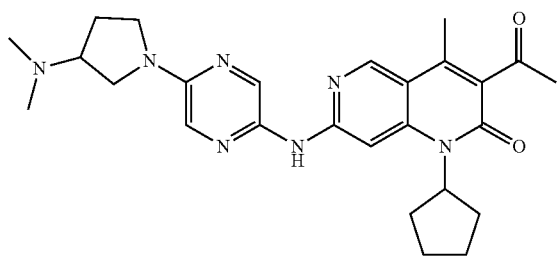 [SMILES: CC(=O)c1c(C)c2cnc(Nc3cnc(N4CCC(N(C)C)C4)cn3)cc2n(C2CCCC2)c1=O]

The synthesis of Example 23 is referred to as that of Example 1. $^1$H NMR (400 MHz, CDCl$_3$) δ 8.63 (s, 1H), 8.14 (d, J=1.1 Hz, 1H), 7.63 (s, 1H), 7.58 (d, J=1.1 Hz, 1H), 7.46 (s, 1H), 5.84-5.59 (m, 1H), 3.77 (dd, J=9.8, 7.2 Hz, 1H), 3.72-3.63 (m, 1H), 3.46 (dt, J=9.9, 6.9 Hz, 1H), 3.37-3.25 (m, 1H), 2.92-2.79 (m, 1H), 2.59-2.51 (m, 3H), 2.39 (s, 3H), 2.34 (s, 6H), 2.30-2.25 (m, 2H), 2.08 (br d, J=4.9 Hz, 2H), 2.00-1.95 (m, 4H), 1.77-1.74 (m, 2H); LCMS (ESI) m/z: 476.2 (M+1).

Example 24

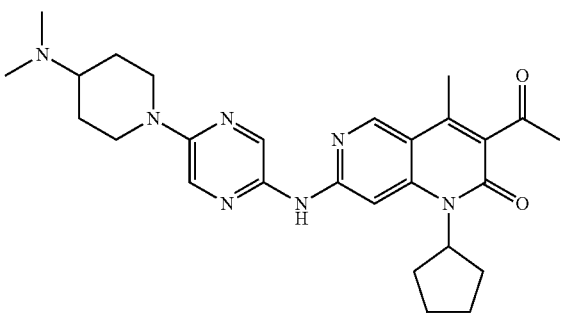 [SMILES: CC(=O)c1c(C)c2cnc(Nc3cnc(N4CCC(N(C)C)CC4)cn3)cc2n(C2CCCC2)c1=O]

The synthesis of Example 24 is referred to as that of Example 8 to give the hydrochloride salt of the title compound. $^1$H NMR (400 MHz, CD$_3$OD) δ 8.75 (s, 1H), 8.20 (s, 1H), 8.10 (br s, 1H), 7.27 (s, 1H), 5.40-5.25 (m, 1H), 4.52 (br d, J=12.3 Hz, 2H), 3.56 (br t, J=11.7 Hz, 1H), 3.01 (br t, J=12.5 Hz, 2H), 2.92 (s, 6H), 2.50 (s, 3H), 2.38 (s, 3H), 2.29-2.13 (m, 6H), 2.07 (br d, J=8.8 Hz, 2H), 1.80 (br d, J=7.8 Hz, 4H); LCMS (ESI) m/z: 490.2 (M+1).

Example 25

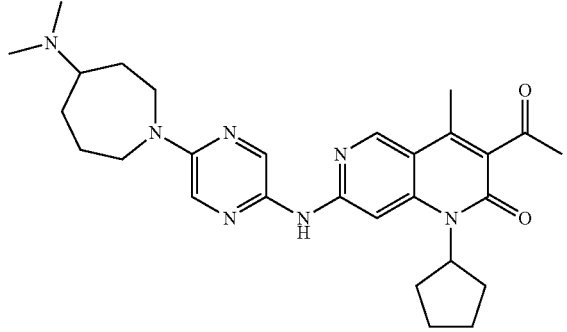 [SMILES: CC(=O)c1c(C)c2cnc(Nc3cnc(N4CCCC(N(C)C)CC4)cn3)cc2n(C2CCCC2)c1=O]

The synthesis of Example 25 is referred to as that of Example 1 to give the hydrochloride salt of the title compound. $^1$H NMR (400 MHz, CD$_3$OD) δ 8.75 (s, 1H), 8.19 (d, J=1.0 Hz, 1H), 8.01 (s, 1H), 7.24 (s, 1H), 5.37 (quin, J=8.7 Hz, 1H), 4.06 (td, J=14.7, 4.8 Hz, 1H), 3.93-3.84 (m, 1H), 3.75-3.59 (m, 2H), 3.51-3.40 (m, 1H), 2.85 (d, J=1.9 Hz, 6H), 2.51 (s, 3H), 2.39 (s, 4H), 2.31-2.13 (m, 6H), 2.12-1.97 (m, 3H), 1.91-1.71 (m, 4H); LCMS (ESI) m/z: 504.3 (M+1).

Example 26

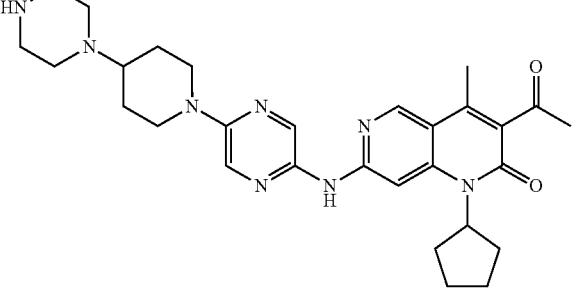

Step 1:

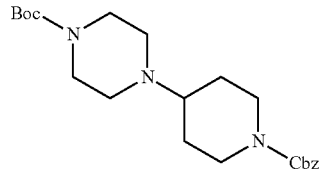 [SMILES: CC(C)(C)OC(=O)N1CCN(C2CCN(C(=O)OCc3ccccc3)CC2)CC1]

Sodium triacetoxyborohydride (22.71 g, 107.18 mmol, 2.50 eq.) was added to a solution of benzyl 4-piperidone-1-carboxylate (10.00 g, 42.87 mmol, 8.55 mL, 1.00 eq.), tert-butyl piperazine-1-carboxylate (9.58 g, 51.44 mmol, 1.20 eq.) and acetic acid (2.57 g, 42.87 mmol, 2.45 mL, 1.00 eq.) in methanol (100.00 mL) at 25° C. The reaction mixture was stirred for 20 hours. The formation of the title compound was confirmed by LCMS. The reaction mixture was concentrated and the obtained residue was diluted with ethyl acetate. The obtained organic phase was washed with water (100 mL) and saturated brine (50 mL) sequentially, and dried over anhydrous sodium sulfate, followed by filtration.

The filtrate was concentrated and the obtained crude product was purified by silica gel column chromatography (petroleum ether:ethyl acetate=10:1 to 1:1) to give the title compound (14.00 g, 27.65 mmol, yield: 64.50%, purity: 79.7%). ¹H NMR (400 MHz, CDCl₃) δ 7.43-7.31 (m, 5H), 5.16-5.12 (m, 2H), 4.36-4.16 (m, 2H), 4.02-3.81 (m, 1H), 3.49-3.40 (m, 4H), 3.23-3.09 (m, 1H), 2.81 (br s, 2H), 2.59-2.45 (m, 4H), 1.81 (br d, J=10.5 Hz, 2H), 1.58-1.39 (m, 11H).

Step 2:

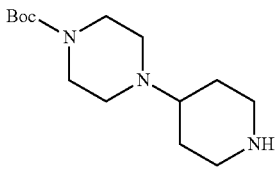 [SMILES: CC(C)(C)OC(=O)N1CCN(C2CCNCC2)CC1]

Palladium on carbon (1.00 g) was added to a solution of tert-butyl 4-(1-benzyloxycarbonyl-4-piperidine)piperazine-1-carboxylate (9.00 g, 22.30 mmol, 1.00 eq.) in tetrahydrofuran (90.00 mL) at 25° C. The suspension was degassed in vacuum and purged several times with hydrogen. Hydrogen pressure was maintained at 15 Psi and the mixture was stirred at 25° C. for 16 hours. The complete conversion of the starting materials was confirmed by LCMS and the MS of the title compound was detected. The reaction mixture was filtered, and the filtrate was concentrated to give the title compound (5.25 g, 19.49 mmol, yield: 87.40%). LCMS (ESI) m/z: 270.1 (M+1).

Step 3:

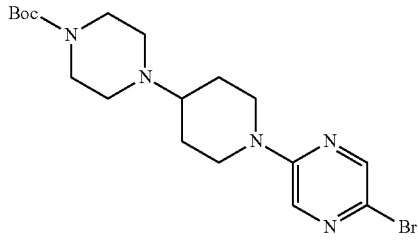 [SMILES: CC(C)(C)OC(=O)N1CCN(C2CCN(c3cnc(Br)cn3)CC2)CC1]

Potassium carbonate (1.28 g, 9.25 mmol, 1.10 eq.) was added to a mixture of tert-butyl 4-(4-piperidinyl)piperazine-1-carboxylate (2.27 g, 8.41 mmol, 1.00 eq.) and 2,5-dibromopyrazine (2.00 g, 8.41 mmol, 1.00 eq.) in dimethyl sulfoxide (30.00 mL) and water (6.00 mL). The reaction mixture was heated to 90° C. and stirred for 16 hours. The complete conversion of the starting materials was confirmed by LCMS and the MS of the title compound was detected. The reaction mixture was cooled to 25° C., followed by addition of water (30 mL). The obtained mixture was stirred for 30 minutes, followed by filtration. The filter cake was dissolved in dichloromethane (30 mL) and washed with water (20 mL×2) and saturated brine (20 mL×2) sequentially. The organic phase was dried over anhydrous sodium sulfate, followed by filtration. The filtrate was concentrated to give the title compound (1.92 g, 4.41 mmol, yield: 52.41%, purity: 97.88%). The product was used in the next step without purification. ¹H NMR (400 MHz, CDCl₃) δ 8.10 (d, J=1.4 Hz, 1H), 7.87 (d, J=1.4 Hz, 1H), 4.28 (br d, J=13.3 Hz, 2H), 3.52-3.33 (m, 4H), 2.98-2.80 (m, 2H), 2.60-2.42 (m, 4H), 1.92 (br d, J=12.3 Hz, 2H), 1.78 (br s, 1H), 1.59-1.50 (m, 2H), 1.46 (s, 9H); LCMS (ESI) m/z: 426.0 (M+1).

Step 4:

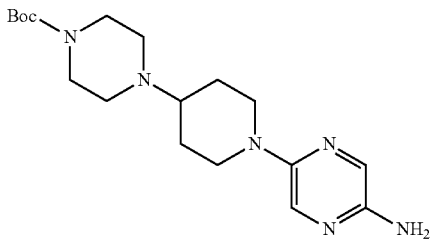 [SMILES: CC(C)(C)OC(=O)N1CCN(C2CCN(c3cnc(N)cn3)CC2)CC1]

LiHMDS (1 M, 7.09 mL, 2.06 eq.) and Pd₂(dba)₃ (315.34 mg, 344.36 μmol, 0.10 eq.) were added to a solution of tert-butyl 4-(1-(5-bromopyrazin-2-yl)-4-piperidinyl]piperazine-1-carboxylate (1.50 g, 3.44 mmol, 1.00 eq.) and tri-tert-butylphosphine tetrafluoroborate (299.73 mg, 1.03 mmol, 0.30 eq.) in toluene (15.00 mL) under nitrogen atmosphere. The reaction mixture was heated to 65° C. and stirred for 16 hours. The complete conversion of most of the starting materials was confirmed by LCMS and the MS of the target compound was detected. The reaction mixture was quenched with saturated aqueous ammonium chloride solution (10 mL), and extracted with ethyl acetate (20 mL). The organic phase was adjusted to pH 2 with a 10% aqueous citric acid solution, followed by partition. The aqueous phase was adjusted to pH 9 with 10% sodium hydroxide solution, followed by filtration. The obtained filter cake was dried in vacuum to give the title compound (672.00 mg, 1.85 mmol, yield: 53.72%, purity: 100%). The product was used in the next step without purification. LCMS (ESI) m/z: 363.1 (M+1).

Step 5:

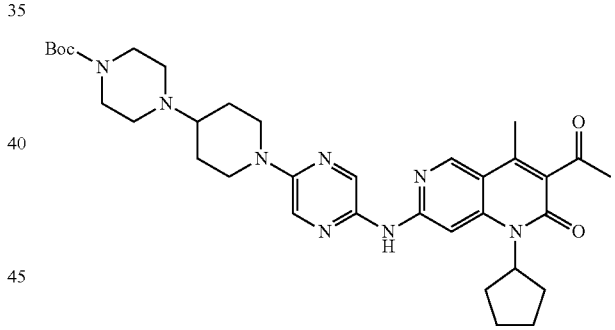

Xphos-Pd-G3 (35.03 mg, 41.38 μmol, 0.05 eq.) was added to a solution of tert-butyl 4-(1-(5-aminopyrazin-2-yl)-4-piperidinyl]piperazine-1-carboxylate (300.00 mg, 827.65 μmol, 1.00 eq.), 3-acetyl-7-chloro-1-cyclopentyl-4-methyl-1,6-naphthyridin-2-one (Intermediate B) (252.24 mg, 827.65 μmol, 1.00 eq.) and potassium tert-butoxide (278.61 mg, 2.48 mmol, 3.00 eq.) in tetrahydrofuran (20.00 mL) under nitrogen atmosphere. The reaction mixture was heated to 80° C. and stirred for 16 hours. The complete conversion of most of the starting materials was confirmed by LCMS and the MS of the title compound was detected. The reaction mixture was concentrated. The obtained residue was dissolved in ethyl acetate (15 mL), and then washed with water (10 mL×2). The organic phase was dried over anhydrous sodium sulfate, followed by filtration. The crude product was purified by preparative TLC (dichloromethane:methanol=10:1) to give the title compound (63.00 mg, 82.87 μmol, yield: 10.01%, purity: 82.976%). LCMS (ESI) m/z: 631.3 (M+1).

Step 6:

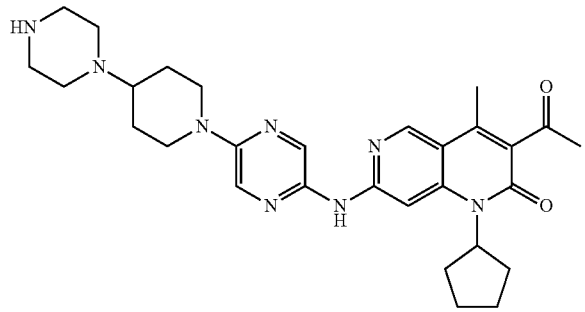 [SMILES: CC(=O)c1c(C)c2cnc(Nc3cnc(N4CCC(N5CCNCC5)CC4)cn3)cc2n(C2CCCC2)c1=O]

Trifluoroacetic acid (1.54 g, 13.51 mmol, 1.00 mL, 162.08 eq.) was added to a solution of tert-butyl 4-[1-[5-[(3-acetyl-1-cyclohexyl-4-methyl-2-oxo-1,6-naphthyridin-7-yl)amino]pyrazin-2-yl]4-piperidinyl]piperazine-1-carboxylate (63.00 mg, 82.87 μmol, 1.00 eq.) in dichloromethane (3.00 mL) at 25° C. The reaction mixture was stirred for 30 minutes. The complete conversion of the starting materials was confirmed by LCMS and the MS of the title compound was detected. The reaction mixture was concentrated, and the obtained crude product was purified by preparative HPLC (hydrochloride acid) to give the hydrochloride salt of the title compound (13.00 mg, 19.34 μmol, yield: 23.34%, purity: 95.231%). $^1$HNMR (400 MHz, CD$_3$OD) δ 8.73 (s, 1H), 8.20 (s, 1H), 8.13 (s, 1H), 7.24 (s, 1H), 5.35 (quin, J=8.5 Hz, 1H), 4.56 (br d, J=13.1 Hz, 2H), 4.05-3.43 (m, 9H), 3.03 (br t, J=12.3 Hz, 2H), 2.49 (s, 3H), 2.38 (s, 3H), 2.34 (br s, 2H), 2.29-2.12 (m, 4H), 2.11-1.99 (m, 2H), 1.96-1.84 (m, 2H), 1.80 (br d, J=5.6 Hz, 2H); LCMS (ESI) m/z: 531.3 (M+1).

Example 27

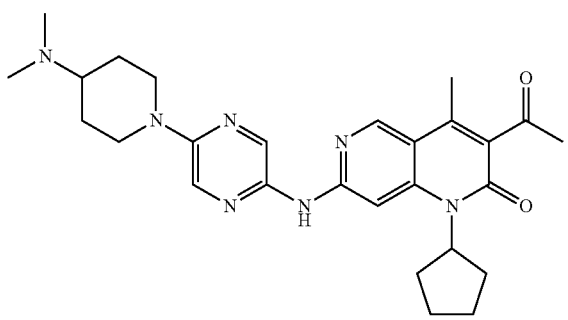 [SMILES: CC(=O)c1c(C)c2cnc(Nc3cnc(N4CCC(N(C)C)CC4)cn3)cc2n(C2CCCC2)c1=O]

The synthesis of Example 27 is referred to as that of Example 26 to give the hydrochloride salt of the title compound. $^1$H NMR (400 MHz, CD$_3$OD) δ 8.75 (s, 1H), 8.22 (s,1H), 8.13 (s, 1H), 7.26 (s, 1H), 5.45-5.31 (m, 1H), 4.56 (br d, J=13.4 Hz, 2H), 4.12 (br d, J=10.1 Hz, 2H), 3.89 (br t, J=12.0 Hz, 2H), 3.58 (br d, J=12.2 Hz, 3H), 3.30-3.20 (m, 2H), 3.02 (br t, J=12.6 Hz, 2H), 2.51 (s, 3H), 2.39 (s, 3H), 2.33 (br d, J=10.1 Hz, 2H), 2.15-2.03 (m, 3H), 2.26-2.00 (m, 3H), 1.90-1.74 (m, 4H); LCMS (ESI) m/z: 532.3 (M+1).

Example 28

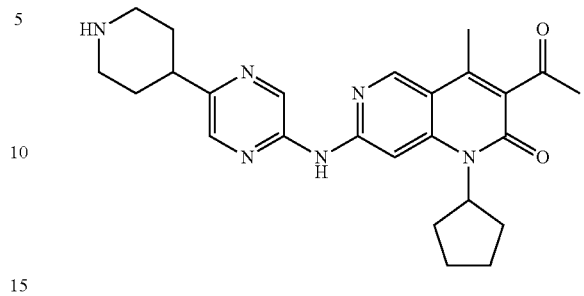

Step 1:

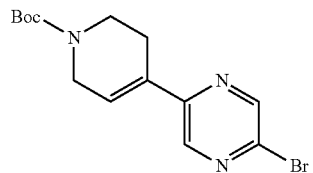 [SMILES: CC(C)(C)OC(=O)N1CC=C(c2cnc(Br)cn2)CC1]

Tert-butyl 4-(4,4,5,5-tetramethyl-1,3,2-dioxoboran-2-yl)-3,6-dihydro-2H-piperidine-1-carboxylate (2.60 g, 8.41 mmol, 1.00 eq.), potassium phosphate (3.57 g, 16.82 mmol, 2.00 eq.) and Pd(dppf)Cl$_2$ (307.60 mg, 420.50 μmol, 0.05 eq.) were added to a mixture of 2,5-dibromopyrazine (2.00 g, 8.41 mmol, 1.00 eq.) in 1,4-dioxane (20.00 mL) and water (2.00 mL) under nitrogen atmosphere. The reaction mixture was heated to 100° C. and stirred for 16 hours. The completion of the reaction was confirmed by TLC (petroleum ether:ethyl acetate=20:1). The reaction solution was concentrated, and the obtained crude product was purified by silica gel column chromatography (petroleum ether:ethyl acetate=20:1 to 10:1) to give the title compound (1.60 g, crude product).

Step 2:

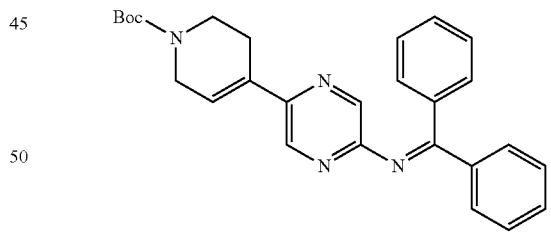

Diphenylmethylimine (879.15 mg, 4.85 mmol, 814.03 μL, 1.10 eq.), cesium carbonate (2.87 g, 8.82 mmol, 2.00 eq.), Pd(OAc)$_2$ (99.01 mg, 441.00 μmol, 0.10 eq.) and BINAP (274.60 mg, 441.00 μmol, 0.10 eq.) were added to a solution of tert-butyl 4-(5-bromopyrazin-2-yl)-3,6-dihydro-2H-pyridine-1-carboxylate (1.50 g, 4.41 mmol, 1.00 eq.) in dioxane (20.00 mL) under nitrogen atmosphere. The reaction solution was heated to 100° C. and stirred for 18 hours. The completion of the reaction was confirmed by LCMS. The reaction mixture was cooled to 20° C. and diluted with dichloromethane (20 mL), followed by filtration. The filtrate was concentrated and the obtained crude product was purified by preparative HPLC (alkaline) to give the title compound (1.40 g, 3.14 mmol, yield: 71.12%, purity: 98.7%). $^1$H NMR (400 MHz, CDCl$_3$) δ 8.36 (d, J=1.1 Hz, 1H), 7.88 (d, J=1.1 Hz, 1H), 7.82 (br d, J=6.7 Hz, 2H), 7.58-7.39 (m, 4H), 7.30 (br d, J=7.1 Hz, 2H), 7.17 (br d, J=6.2 Hz, 2H), 6.55 (br s, 1H), 4.11 (br d, J=2.4 Hz, 2H), 3.62 (br t, J=5.5 Hz, 2H), 2.57 (br s, 2H), 1.48 (s, 9H).

Step 3:

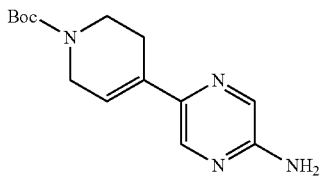 [SMILES: CC(C)(C)OC(=O)N1CC=C(c2cnc(N)cn2)CC1]

Sodium acetate (110.27 mg, 1.34 mmol, 1.20 eq.) and hydroxylamine hydrochloride (140.12 mg, 2.02 mmol, 1.80 eq.) were added to a solution of tert-butyl 4-(5-(diphenyl-methyleneamino)pyrazin-2-yl]-3,6-dihydro-2H-pyridine-1-carboxylate (500.00 mg, 1.12 mmol, 1.00 eq.) in methanol (10.00 mL) at 25° C., and stirred for 30 minutes. The completion of the reaction was confirmed by LCMS. The reaction solution was concentrated, and the obtained crude product was purified by preparative TLC (petroleum ether: ethyl acetate=1:1) to give the title compound (190.00 mg, 687.58 μmol, yield: 61.38%). $^1$H NMR (400 MHz, CDCl$_3$) δ 8.10 (d, J=1.2 Hz, 1H), 7.95 (d, J=1.3 Hz, 1H), 6.42 (br s, 1H), 4.59 (br s, 2H), 4.11 (br d, J=2.7 Hz, 2H), 3.64 (br t, J=5.6 Hz, 2H), 2.58 (br s, 2H), 1.49 (s, 9H).

Step 4:

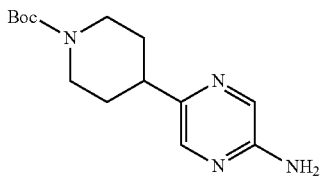 [SMILES: CC(C)(C)OC(=O)N1CCC(c2cnc(N)cn2)CC1]

Palladium on carbon (100.00 mg, wetted with water) was added to a solution of tert-butyl 4-(5-aminopyrazin-2-yl)-3,6-dihydro-2H-pyridine-1-carboxylate (180.00 mg, 651.40 μmol, 1.00 eq.) in methanol (3.00 mL). Hydrogen pressure was maintained at 15 Psi and the reaction mixture was stirred at 25° C. for 1 hour. About 60% of the starting materials remained was confirmed by LCMS, and the reaction mixture was stirred under this condition for 18 hours. The completion of the reaction was confirmed by LCMS. The reaction solution was filtered, and the filtrate was concentrated to give the title compound (160.00 mg, 574.82 μmol, yield: 88.24%). $^1$H NMR (400 MHz, CDCl$_3$) δ 7.94 (d, J=1.4 Hz, 1H), 7.87 (d, J=1.4 Hz, 1H), 4.46 (br s, 2H), 4.25 (br s, 2H), 2.82 (br t, J=10.5 Hz, 2H), 2.78-2.69 (m, 1H), 1.85 (br d, J=13.2 Hz, 2H), 1.69 (dd, J=12.7, 4.1 Hz, 2H), 1.48 (s, 9H).

Step 5:

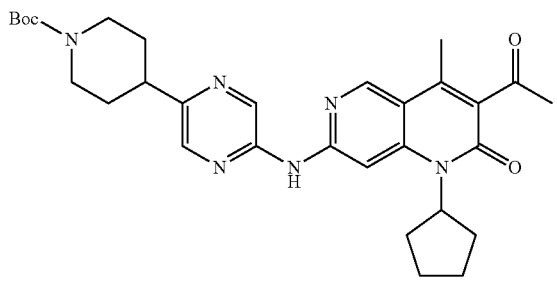 [SMILES: CC(=O)c1c(C)c2cnc(Nc3cnc(C4CCN(C(=O)OC(C)(C)C)CC4)cn3)cc2n(C2CCCC2)c1=O]

3-Acetyl-7-chloro-1-cyclopentyl-4-methyl-1,6-naphthy-ridin-2-one (Intermediate B) (164.24 mg, 538.89 μmol, 1.00 eq.), potassium tert-butoxide (120.94 mg, 1.08 mmol, 2.00 eq.) and Xphos-Pd-G3 (45.61 mg, 53.89 μmol, 0.10 eq.) were added to a solution of tert-butyl 4-(5-aminopyrazin-2-yl)piperidine-1-carboxylate (150.00 mg, 538.89 μmol, 1.00 eq.) in tetrahydrofuran (3.00 mL) under nitrogen atmosphere. The reaction mixture was heated to 70° C. and stirred for 18 hours. The completion of the reaction was confirmed by LCMS. The reaction mixture was cooled to 25° C. and diluted with dichloromethane (10 mL), followed by filtration. The filtrate was concentrated and the obtained crude product was purified by preparative TLC (petroleum ether: ethyl acetate=1:2) to give the title compound (92.00 mg, 168.29 μmol, yield: 31.23%). $^1$H NMR (400 MHz, CDCl$_3$) δ 8.70 (s, 1H), 8.40 (d, J=1.4 Hz, 1H), 8.27 (s, 1H), 8.29-8.23 (m, 1H), 8.09 (d, J=1.3 Hz, 1H), 7.65 (s, 1H), 5.82 (quin, J=9.4 Hz, 1H), 4.29 (br s, 2H), 2.87 (ddd, J=11.8, 8.4, 3.8 Hz, 3H), 2.57 (s, 3H), 2.43 (s, 3H), 2.39-2.28 (m, 2H), 2.28-2.16 (m, 2H), 2.08-1.99 (m, 2H), 1.95-1.88 (m, 2H), 1.87-1.71 (m, 4H), 1.49 (s, 8H), 1.51-1.47 (m, 1H).

Step 6:

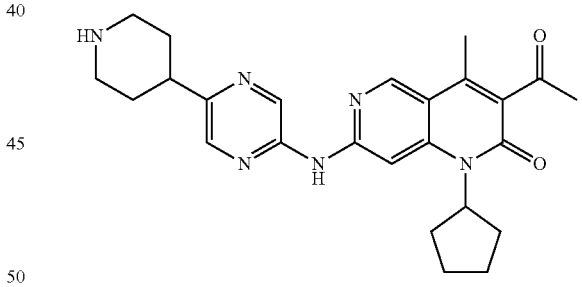

Trifluoroacetic acid (500.00 μL) was added to a solution of tert-butyl 4-[5-[(3-acetyl-1-cyclopentyl-4-methyl-2-oxo-1,6-naphthyridin-7-yl)amino]piperazin-2-yl]piperidine-1-carboxylate (87.00 mg, 159.15 μmol, 1.00 eq.) in dichloromethane (1.00 mL). The reaction solution was stirred at 30° C. for 0.5 hour. The completion of the reaction was confirmed by LCMS. The reaction solution was concentrated, and the obtained crude product was purified by preparative HPLC (hydrochloride acid) to give the hydrochloride salt of the title compound (37.58 mg, 70.61 μmol, yield: 44.36%, purity: 97.599%). $^1$H NMR (400 MHz, CD$_3$OD) δ 8.86 (s, 1H), 8.62 (d, J=0.8 Hz, 1H), 8.43 (s, 1H), 7.47 (s, 1H), 5.40 (quin, J=8.6 Hz, 1H), 3.55 (br d, J=12.8 Hz, 2H), 3.29-3.17 (m, 3H), 2.50 (s, 3H), 2.41 (s, 3H), 2.30-2.01 (m, 10H), 1.86-1.74 (m, 2H); LCMS (ESI) m/z: 447.2 (M+1).

Example 29

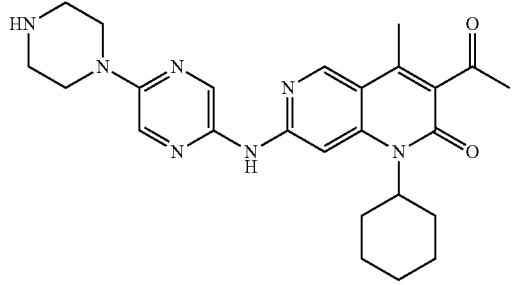 [SMILES: CC(=O)c1c(C)c2cnc(Nc3cnc(N4CCNCC4)cn3)cc2n(C2CCCCC2)c1=O]

The synthesis of Example 29 is referred to as that of Example 1 to give the trifluoroacetate of the title compound. ¹HNMR (400 MHz, CD₃OD) δ 8.69 (s, 1H), 8.32 (d, J=1.1 Hz, 1H), 8.08 (d, J=1.5 Hz, 1H), 7.70 (br s, 1H), 3.91-3.71 (m, 4H), 4.88-4.87 (m, 1H), 3.42-3.35 (m, 4H), 2.67-2.51 (m, 2H), 2.48 (s, 3H), 2.37 (s, 3H), 2.04-1.93 (m, 2H), 1.80 (br d, J=11.8 Hz, 3H), 1.54 (q, J=13.0 Hz, 2H), 1.40 (br t, J=12.7 Hz, 1H); LCMS (ESI) m/z: 462.3 (M+1).

Example 30

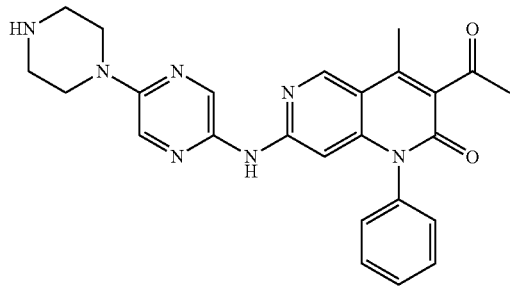 [SMILES: CC(=O)c1c(C)c2cnc(Nc3cnc(N4CCNCC4)cn3)cc2n(-c2ccccc2)c1=O]

The synthesis of Example 30 is referred to as that of Example 1 to give the hydrochloride salt of the title compound. ¹H NMR (400 MHz, CD₃OD) δ 8.84 (s, 1H), 8.17 (d, J=1.5 Hz, 1H), 8.05 (d, J=1.5 Hz, 1H), 7.75-7.60 (m, 3H), 7.47-7.36 (m, 2H), 6.30 (s, 1H), 3.94-3.78 (m, 4H), 3.41-3.34 (m, 4H), 2.52 (s, 3H), 2.49 (s, 3H); LCMS (ESI) m/z: 456.1 (M+1).

Schedule B

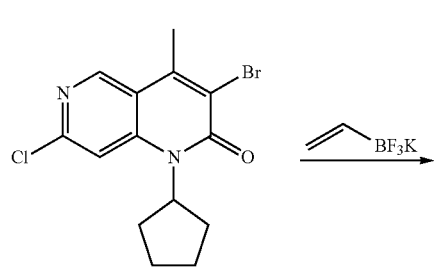

Intermediate A

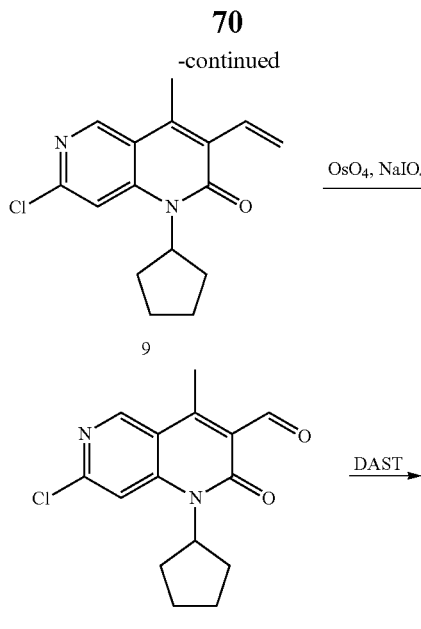

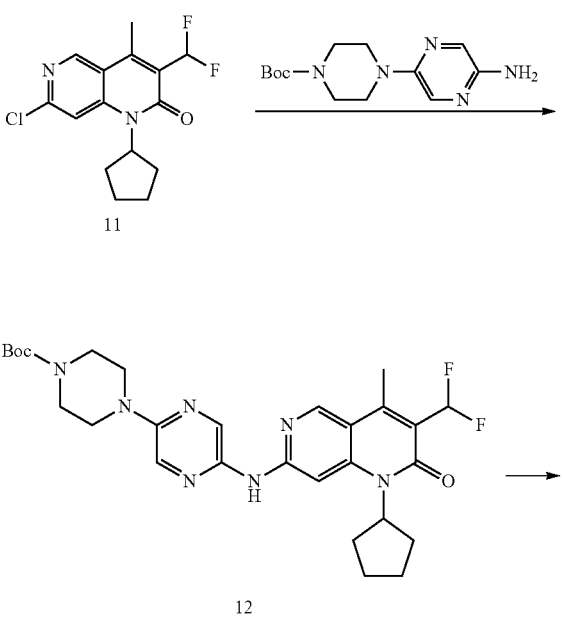

Example 31

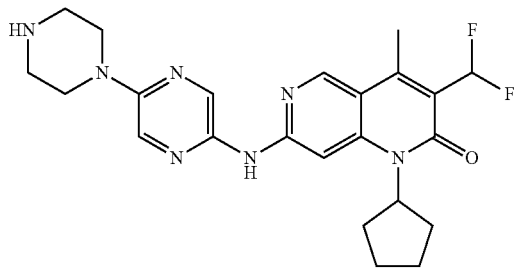 [SMILES: Cc1c(C(F)F)c(=O)n(C2CCCC2)c2cc(Nc3cnc(N4CCNCC4)cn3)ncc12]

Step 1:

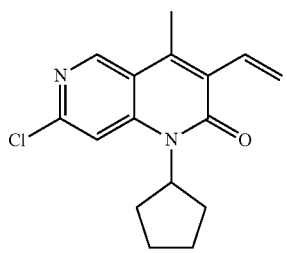 [SMILES: C=Cc1c(C)c2cnc(Cl)cc2n(C2CCCC2)c1=O]

Pd(PPh₃)₂Cl₂ (275.76 mg, 392.88 μmol, 0.05 eq.) was added to a mixture of 3-bromo-7-chloro-1-cyclopentyl-4-methyl-1,6-naphthyridin-2-one (Intermediate A) (3.00 g, 7.86 mmol, 1.00 eq.), potassium vinyltrifluoroborate (1.26 g, 9.43 mmol, 1.20 eq.) and cesium carbonate (5.12 g, 15.72 mmol, 2.00 eq.) in dioxane (30.00 mL) and water (6.00 mL) under nitrogen atmosphere. The reaction mixture was heated to 110° C. and stirred for 2 hours. The completion of the reaction was confirmed by LCMS. The reaction mixture was cooled to 25° C., followed by addition of water (20 mL), and concentrated to remove dioxane. The aqueous phase was extracted with ethyl acetate (30 mL×3). The combined organic phase was wash with saturated brine (30 mL×2), and dried over anhydrous sodium sulfate, followed by filtration. The filtrate was concentrated and the obtained crude product was purified by silica gel column chromatography (petroleum ether:ethyl acetate=30:1) to give the title compound (Compound 9) (1.00 g, 3.46 mmol, yield: 44.03%). ¹H NMR (400 MHz, CDCl₃) δ 8.77 (s, 1H), 7.34 (s, 1H), 6.82-6.72 (m, 1H), 5.75 (s, 1H), 5.71 (dd, J=7.4, 1.9 Hz, 1H), 5.41 (quin, J=8.9 Hz, 1H), 2.60 (s, 3H), 2.28-2.18 (m, 2H), 2.17-2.08 (m, 2H), 2.05-1.97 (m, 2H), 1.82-1.74 (m, 2H); LCMS (ESI) m/z: 251.1 (M+1).

Step 2:

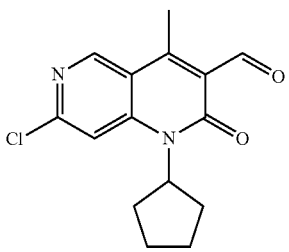 [SMILES: Cc1c(C=O)c(=O)n(C2CCCC2)c2cc(Cl)ncc12]

Sodium periodate (1.56 g, 7.27 mmol, 402.97 μL, 3.00 eq.) and osmium tetroxide (24.65 mg, 96.96 μmol, 5.03 μL, 0.04 eq.) were added to a mixture of 7-chloro-1-cyclopentyl-4-methyl-3-vinyl-1,6-naphthyridin-2-one (Compound 9) (700.00 mg, 2.42 mmol, 1.00 eq.) in dioxane (8.00 mL) and water (2.00 mL). The mixture was stirred at 30° C. for 2 hours. The completion of the reaction was confirmed by TLC. The reaction mixture was diluted with water (10 mL), followed by filtration. The filtrate was extracted with ethyl acetate (20 mL×2). The combined organic phase was wash with saturated brine (20 mL×2), and dried over anhydrous sodium sulfate, followed by filtration. The filtrate was concentrated and the obtained crude product was purified by silica gel column chromatography (petroleum ether:ethyl acetate=20:1) to give the title compound (Compound 10) (560.00 mg, 1.93 mmol, yield: 79.62%). ¹H NMR (400 MHz, CDCl₃) δ 10.46 (s, 1H), 8.87 (s, 1H), 7.28 (s, 1H), 5.33 (quin, J=8.9 Hz, 1H), 2.77 (s, 3H), 2.15 (br dd, J=12.1, 7.6 Hz, 2H), 2.05 (br dd, J=8.4, 5.4 Hz, 2H), 1.99-1.93 (m, 2H), 1.76-1.69 (m, 2H).

Step 3:

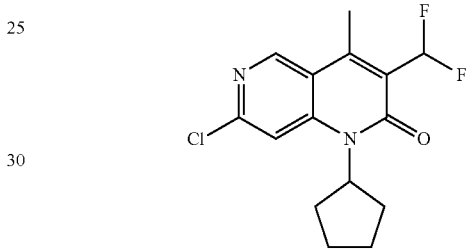

DAST (1.56 g, 9.65 mmol, 1.27 mL, 5.00 eq.) was added to a solution of dichloro-7-chloro-1-cyclopentyl-4-methyl-2-oxo-1,6-naphthyridin-3-carbaldehyde (Compound 10) (560.00 mg, 1.93 mmol, 1.00 eq.) in dichloromethane (6.00 mL) at 25° C. The mixture was stirred for 16 hours. The completion of the reaction was confirmed by LCMS. The reaction solution was concentrated, and the obtained crude product was purified by silica gel column chromatography (petroleum ether:ethyl acetate=20:1) to give the title compound (Compound 11) (500.00 mg, 1.60 mmol, yield: 82.84%). ¹H NMR (400 MHz, CDCl₃) δ 10.46 (s, 1H), 8.87 (s, 1H), 7.28 (s, 1H), 5.33 (quin, J=8.9 Hz, 1H), 2.77 (s, 3H), 2.20-2.11 (m, 2H), 2.08-2.01 (m, 2H), 1.99-1.92 (m, 2H), 1.78-1.70 (m, 2H).

Step 4:

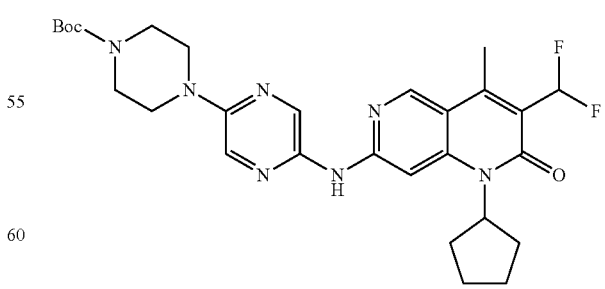

Cesium carbonate (208.36 mg, 639.51 μmol, 2.00 eq.), Xphos (15.24 mg, 31.98 μmol, 0.10 eq.) and Pd(OAc)₂ (3.59 mg, 15.99 μmol, 0.05 eq.) were added to a solution of 7-chloro-1-cyclopentyl-3-(difluoromethyl)-4-methyl-1,6- naphthyridin-2-one (Compound 11) (100.00 mg, 319.75 µmol, 1.00 eq.), tert-butyl 4-(5-aminopyrazin-2-yl)piperazine-1-carboxylate (107.18 mg, 383.71 µmol, 1.20 eq.) in dioxane (2.00 mL) under nitrogen atmosphere. The reaction mixture was heated to 100° C. and stirred for 16 hours. The completion of the reaction was confirmed by LCMS. The reaction mixture was cooled to 30° C., followed by filtration. The filtrate was concentrated and the obtained crude product was purified by preparative TLC (petroleum ether:ethyl acetate=2:1) to give the title compound (Compound 12) (16.70 mg, 30.06 µmol, yield: 9.40%). LCMS (ESI) m/z: 251.1 (M+1).

Step 5:

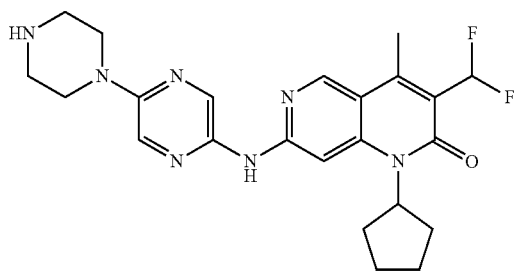 [SMILES: Cc1c(C(F)F)c(=O)n(C2CCCC2)c2cc(Nc3cnc(N4CCNCC4)cn3)ncc12]

Trifluoroacetic acid (1.00 mL) was added to a solution of tert-butyl 4-[5-[[1-cyclopentyl-3-(difluoromethyl)-4-methyl-2-oxo-1,6-naphthyridin-7-yl]amino]pyrazine-2-piperazine-1-carboxylate (Compound 12) (20.00 mg, 36.00 µmol, 1.00 eq.) in dichloromethane (2.00 mL) at 30° C. The reaction solution was stirred for 0.5 hours. The completion of the reaction was confirmed by LCMS. The reaction solution was concentrated under reduced pressure to remove dichloromethane and trifluoroacetic acid. The obtained crude product was purified by preparative HPLC (hydrochloric acid) to give the hydrochloride salt of the title compound (15.00 mg, 28.03 µmol, yield: 77.86%, purity: 98.74%). $^1$H NMR (400 MHz, CD$_3$OD) δ 8.86 (s, 1H), 8.28 (d, J=0.9 Hz, 1H), 8.22 (s, 1H), 7.33-7.06 (m, 2H), 5.45-5.34 (m, 1H), 3.96-3.88 (m, 4H), 3.45-3.39 (m, 4H), 2.70 (s, 3H), 2.30-2.16 (m, 4H), 2.12-2.02 (m, 2H), 1.83 (br d, J=5.5 Hz, 2H); LCMS (ESI) m/z: 251.1 (M+1).

Example 32

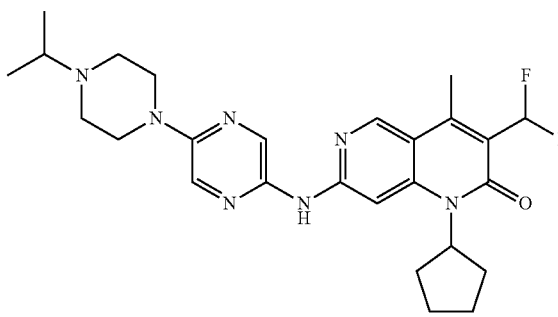

Acetone (112.84 mg, 1.94 mmol, 142.84 µL, 5.00 eq.), sodium triacetoxyborohydride (205.89 mg, 971.45 µmol, 2.50 eq.) and acetic acid (46.67 mg, 777.16 µmol, 44.45 µL, 2.00 eq.) were added to a solution of 1-cyclopentyl-3-(difluoromethyl)-4-methyl-7-[(5-piperazin-1-ylpyrazin-2-yl)amino]-1,6-naphthyridine-2-one (177.00 mg, 388.58 µmol, 1.00 eq.) in dichloroethane (5.00 mL). The reaction mixture was stirred at 30° C. for 2 hours. The complete conversion of the starting materials was confirmed by LCMS and the MS of the title compound was detected. The reaction solution was concentrated under reduced pressure, and the obtained crude product was purified by preparative HPLC (hydrochloride) to give the hydrochloride salt of the title compound (49.67 mg, 85.49 µmol, yield: 22.00%, purity: 98.19%). $^1$H NMR (400 MHz, CD$_3$OD) δ 8.86 (s, 1H), 8.27 (d, J=1.1 Hz, 1H), 8.23 (d, J=1.2 Hz, 1H), 7.34-7.07 (m, 1H), 7.24 (s, 1H), 5.45-5.33 (m, 1H), 4.58 (br d, J=13.6 Hz, 2H), 3.68 (br d, J=13.1 Hz, 2H), 3.72-3.66 (m, 1H), 3.43-3.35 (m, 2H), 3.32-3.22 (m, 2H), 2.70 (s, 3H), 2.32-2.13 (m, 4H), 2.12-2.00 (m, 2H), 1.88-1.75 (m, 2H), 1.46 (d, J=6.6 Hz, 6H); LCMS (ESI) m/z: 498.0 (M+1).

Example 33

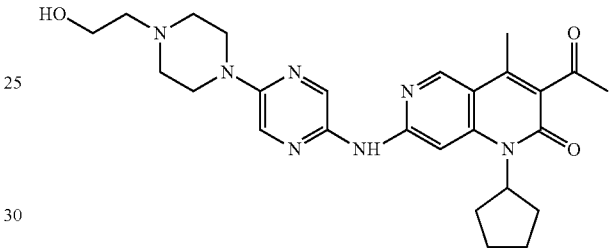

2-Bromoethanol (72.60 mg, 580.96 µmol, 41.25 µL, 1.3 eq.) and sodium carbonate (142.10 mg, 1.34 mmol, 3.0 eq.) were added to a solution of 3-acetyl-1-cyclopentyl-4-methyl-7-[(5-piperazin-1-ylpyrazin-2-yl)amino]-1,6-naphthyridin-2-one (0.2 g, 446.89 µmol, 1 eq.) in DMF (4 mL). The reaction mixture was heated to 80° C. and stirred for 16 hours. The completion of the reaction was confirmed by LCMS. The reaction mixture was filtered and purified by preparative HPLC (alkaline) to give the title compound. $^1$H NMR (400 MHz, DMSO-d$_6$) δ 9.95 (br s, 1H), 8.75 (s, 1H), 8.54 (s, 1H), 7.97 (s, 1H), 7.63 (s, 1H), 5.57 (quin, J=9.1 Hz, 1H), 3.55 (t, J=6.2 Hz, 2H), 3.48-3.41 (m, 4H), 2.57-2.53 (m, 4H), 2.47-2.39 (m, 5H), 2.34 (s, 3H), 2.25-2.06 (m, 4H), 1.94-1.82 (m, 2H), 1.77-1.65 (m, 2H); LCMS (ESI) m/z: 492.4 (M+1)

Example 34

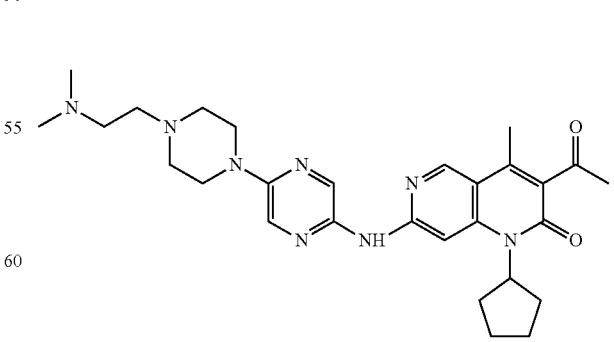

Sodium iodide (13.40 mg, 89.38 µmol, 0.2 eq.) was added to a solution of 3-acetyl-1-cyclopentyl-4-methyl-7-[(5-piperazin-1-ylpyrazin-2-yl)amino]-1,6-naphthyridin-2-one (200 mg, 446.89 µmol, 1 eq.), 2-chloro-N,N-dimethylethylamine (64.37 mg, 446.89 µmol, 1 eq., hydrochloride) and sodium carbonate (142.10 mg, 1.34 mmol, 3 eq.) in DMF (5 mL). The reaction mixture was heated to 80° C. and stirred for 16 hours. The completion of the reaction was confirmed by LCMS. The reaction mixture was filtered and the filtrate was purified by preparative HPLC (hydrochloric acid) to give the hydrochloride salt of the title compound. $^1$H NMR (400 MHz, CD$_3$OD) δ 8.75 (s, 1H), 8.27 (d, J=0.9 Hz, 1H), 8.22 (s, 1H), 7.25 (s, 1H), 5.41 (quin, J=8.8 Hz, 1H), 3.82-3.70 (m, 4H), 3.69-3.35 (m, 4H), 3.33-3.31 (m, 4H), 3.06 (s, 6H), 2.51 (s, 3H), 2.40 (s, 3H), 2.32-2.16 (m, 4H), 2.13-2.03 (m, 2H), 1.83 (br d, J=5.9 Hz, 2H); LCMS (ESI) m/z: 519.5 (M+1).

Example 35

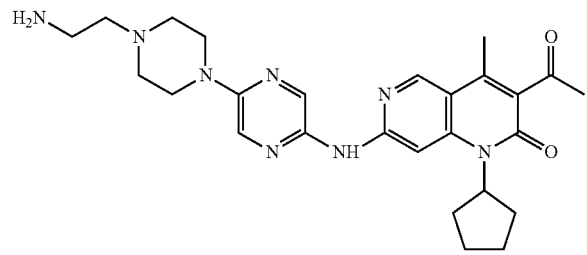 [SMILES: CC(=O)c1c(C)c2cnc(Nc3cnc(N4CCN(CCN)CC4)cn3)cc2n(C2CCCC2)c1=O]

Step 1:

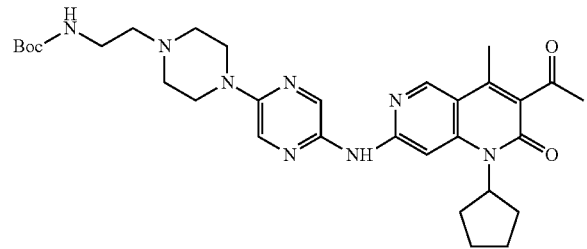 [SMILES: CC(=O)c1c(C)c2cnc(Nc3cnc(N4CCN(CCNC(=O)OC(C)(C)C)CC4)cn3)cc2n(C2CCCC2)c1=O]

Tert-butyl N-(2-bromoethyl)carbamate (90.13 mg, 402.21 µmol, 1.2 eq.) and sodium carbonate (106.57 mg, 1.01 µmol, 3 eq.) were added to a solution of 3-acetyl-1-cyclopentyl-4-methyl-7-[(5-piperazin-1-ylpyrazin-2-yl)amino]-1,6-naphthyridin-2-one (0.15 g, 335.17 µmol, 1 eq.) in DMF (3 mL). The reaction mixture was heated to 80° C. and stirred for 16 hours. The complete conversion of the starting materials and the formation of the title product was confirmed by LCMS. The reaction mixture is filtered to give a solution of the title compound in DMF, which was used directly in the next step without further purification. LCMS (ESI) m/z: 591.5 (M+1).

Step 2:

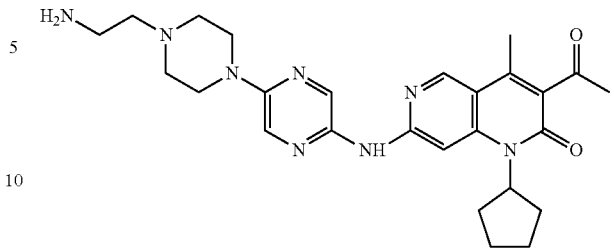

Trifluoroacetic acid (1 mL) was added to a solution of tert-butyl N-[2-[4-[5-[(3-acetyl-1-cyclopentyl-4-methyl-2-oxo-1,6-naphthyridin-7-yl)amino]pyrazine-2-piperazin-1-yl]ethyl]carboxylate (197.99 mg, 335.17 mmol, 1 eq) in DMF (3 mL). The reaction mixture was stirred at 20° C. for 15 hours. The incomplete conversion of the starting material was confirmed by LCMS, but a large amount of the title product was formed. The reaction mixture was filtered, and the filtrate was purified by preparative HPLC (hydrochloric acid) to give the hydrochloride salt of title compound. $^1$H NMR (400 MHz, DMSO-d$_6$) δ 11.52 (br s, 1H), 10.72 (br s, 1H), 8.78 (s, 1H), 8.57 (s, 1H), 8.46 (br s, 3H), 8.14 (d, J=1.0 Hz, 1H), 7.67 (s, 1H), 5.53 (br t, J=8.9 Hz, 1H), 4.34 (br s, 2H), 3.49-3.30 (m, 6H), 2.44 (s, 3H), 2.33 (s, 3H), 2.26-2.04 (m, 4H), 1.90 (br d, J=8.6 Hz, 2H), 1.77-1.65 (m, 2H); LCMS (ESI) m/z: 491.4 (M+1).

Example 36

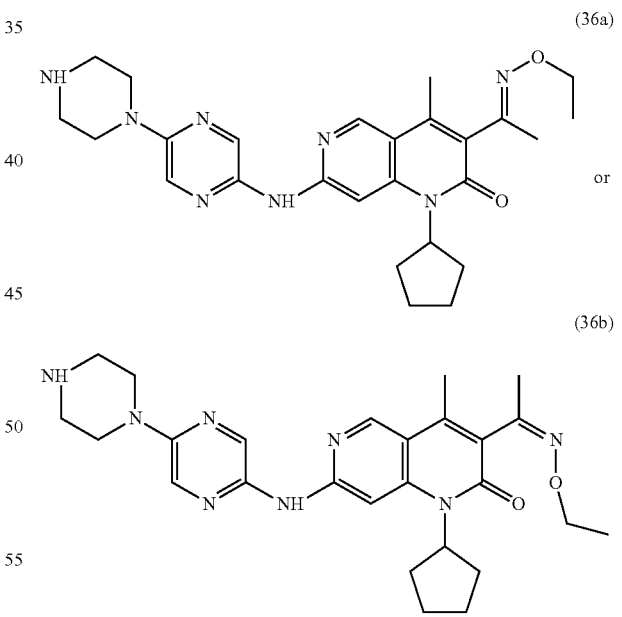

3-Acetyl-1-cyclopentyl-4-methyl-7-[(5-piperazin-1-ylpyrazin-2-yl)amino]-1,6-naphthyridin-2-one (0.1 g, 223.45 µmol, 1 eq.) was added to a solution of O-ethylhydroxylamine hydrochloride (130.78 mg, 1.34 mmol, 6 eq.) in pyridine (2 mL). The reaction mixture was heated to 70° C. and stirred for 16 hours. The completion of the reaction was confirmed by LCMS. The reaction mixture was cooled to 20° C. and concentrated to dryness. The obtained residue is purified by preparative HPLC (hydrochloric acid) to give the hydrochloride salt of the title compound 36a or 36b. $^1$H NMR (400 MHz, CD$_3$OD) δ 9.45 (br s, 2H), 8.74 (s, 1H), 8.53 (s, 1H), 8.09 (d, J=1.1 Hz, 1H), 7.64 (s, 1H), 5.57-5.46 (m, 1H), 4.11 (br d, J=7.0 Hz, 4H), 3.76-3.71 (m, 4H), 3.21 (br s, 4H), 2.37 (s, 3H), 2.23-2.09 (m, 4H), 2.00 (s, 3H), 1.89 (br d, J=9.0 Hz, 2H), 1.70 (br s, 2H), 1.24 (t, J=7.0 Hz, 3H); LCMS (ESI) m/z: 491.3 (M+1); HPLC of the title compound: RT=2.088 min.

PHARMACOLOGICAL SECTION

The compounds of the present invention are CDK4/6 inhibitors. The following experimental results verify that the compounds listed in the present application are indeed CDK4/6 inhibitors and can be used as potential anti-cancer drugs. The IC$_{50}$ as used herein refers to the concentration of the corresponding reagent that is required for producing 50% maximal inhibition.

Experimental Example 1: Enzyme Activity Assay

Experimental Materials:
CDK4/cyclin D1, CDK6/cyclin D1 (Life technology). ULight labeled polypeptide substrates ULight-4E-BP1 and ULight-MBP (PerkinElmer). Europium labeled anti-myelin basic protein antibody and europium labeled rabbit-derived antibody (PerkinElmer). Envision Multi-label Analyzer (PerkinElmer) for signal detection.

Experimental Methods:
The tested compounds were diluted three-fold, including 10 concentration gradients, and range of the final concentration was 5 μM to 0.25 nM.

Enzymatic Reaction System of CDK4/cyclin D1
The standard Lance Ultra method was performed by a 10 μIL enzymatic reaction system containing 0.3 nM CDK4/cyclin D1 protein, 50 nM ULight-4E-BP1 polypeptide, and 350 μM ATP. They were respectively dissolved in an enzyme buffer solution comprising: 50 mM hydroxyethylpiperazine ethanesulfuric acid solution at pH 7.5, 1 mM ethylenediaminetetraacetic acid, 10 mM magnesium chloride, 0.01% Brij-35, 2 mM dithiothreitol. After the reaction was begun, the OptiPlate 384-well plate was sealed with a top heat seal film TopSeal-A, and incubated at room temperature for 180 minutes.

Enzymatic Reaction System of CDK6/cyclin D1
The standard Lance Ultra method was performed by a 10 μL enzymatic reaction system containing 0.8 nM CDK6/cyclin D1 protein, 50 nM ULight-4E-BP1 polypeptide, and 250 μM ATP. They were respectively dissolved in an enzyme buffer solution comprising: 50 mM hydroxyethylpiperazine ethanesulfuric acid solution at pH 7.5, 1 mM ethylenediaminetetraacetic acid, 10 mM magnesium chloride, 0.01% Brij-35, 2 mM dithiothreitol. After the reaction was started, the OptiPlate 384-well plate was sealed with a top heat seal film TopSeal-A and incubated at room temperature for 180 minutes.

The termination buffer solution of the enzymatic reaction was prepared, and EDTA was dissolved in a 1-fold diluted assay buffer solution. The reaction was terminated and incubated at room temperature for 5 minutes. 5 μL of the assay mixed solution (prepared with europium labeled anti-myelin basic protein antibody and europium labeled rabbit-derived antibody, respectively) was added to the reactions of CDK4/cyclin D1 and CDK6/cyclin D1, respectively, and incubated at room temperature for 60 minutes. The reaction signal was detected by Envision according to the time-resolved fluorescence resonance energy transfer theory.

Data Analysis:
The raw data is converted to the inhibition rate using the equation (Max-Ratio)/(Max-Min)*100%, and the value of IC$_{50}$ can be obtained by curve-fitting with four parameters (Model 205 in XLFIT5, iDBS). Table 1 provides the inhibitory activity of the compounds of the present invention against CDK4/CDK6 kinase.

Experimental Results: See Table 1.
Experimental Conclusion:
The compounds of the present invention have significant inhibitory activity against CDK4 and CDK6 kinase.

Experimental Example 2: Cell Viability Assay

Experimental Materials:
RPMI 1640 medium (Invitrogen-22400089), fetal calf serum (Gibco-10099141), penicillin/streptomycin antibiotic (Hyclone-SV30010), L-glutamine (Invitrogen-35050079). The NCI-H358 cell line is from the cell bank of the Department of Biology of WuXi Apptec Co. Ltd. Envision Multi-Label Analyzer (PerkinElmer).

Experimental Methods:
1) 100 μL of phosphate buffer solution was added to the peripheral wells of the 384-well plate and 40 μL of NCI-H358 cell suspension was added to the other wells containing 250 NCI-H358 cells. The cell plate was then placed in a carbon dioxide incubator and incubated overnight.

2) A 3-fold gradient dilution was subjected to the tested compounds using Echo. Each compound was diluted by 10 concentration gradients (diluted from 25 μM to 1.27 nM), 100 nL of which was added to the corresponding wells of the cell plate. The cell plate was then placed in a carbon dioxide incubator and incubated for 7 days.

3) 20 μL of Promega CellTiter-Glo reagent was added to each well of the cell plate, and shaken for 10 minutes away from light at room temperature to stabilize the luminescence signal. Readings were performed using a PerkinElmer Envision Multi-label Analyzer.

Data Analysis:
The raw data is converted to the inhibition rate using the equation (Max-Sample)/(Max-Min)*100%, and the IC50 value can be obtained by curve-fitting with four parameters (calculated by the formula of log(inhibitor) vs. response–Variable slope in GraphPad Prism). Table 1 provides the inhibitory activity of the compounds of the present invention against the proliferation of H358 cells.

Experimental Results: See Table 1.
Experimental Conclusion:
The compounds of the present invention have better proliferation inhibitory activity against NCI-H358 lung cancer cells than that of the reference compound Palbociclib.

TABLE 1

| Tested compound | CDK4 IC$_{50}$ (nM) | CDK6 IC$_{50}$ (nM) | H358 Cell IC$_{50}$ (nM) |
| --- | --- | --- | --- |
| Palbociclib | 5.5 | 1.3 | 314 |
| Example 3 | 6.1 | 2.9 | 176 |
| Example 9 | 9.1 | 3.4 | 195.6 |
| Example 11 | 5.6 | 3.1 | 278 |
| Example 14 | 7.1 | 2.4 | 197 |
| Example 15 | 5.7 | 3.1 | 262 |
| Example 19 | 7.0 | 3.7 | 214 |
| Example 28 | 8.3 | 3.5 | 295 |
| Example 33 | 8.62 | 4.66 | 153 |
| Example 34 | 7.45 | 3.65 | 179 |
| Example 35 | 5.06 | 2.97 | 189 |

Experimental Example 3: Two-Way Permeability Evaluation Assay of Caco-2 Cells

Experimental Objective:

Caco-2 cell is a human colon cancer cell, acting as an in vitro model widely used in studying intestinal absorption. The monolayer Caco-2 cell model has been widely used in assessing the passive and active transport processes during intestinal absorption. This assay was used to determine the bidirectional permeability through the Caco-2 cell model of the compounds of the present invention and the reference compounds Palbociclib and LY2835219.

Experimental Procedures:

The standard experimental conditions are as follows:

Assay concentration: 2 µM (DMSO≤1%);

Repeat: n=2;

Direction: two-way transport, including two directions: A→B (intracellular→extracellular) and B→A (extracellular→intracellular);

Incubation time: single time point, 2 hours;

transport buffer solution: HBSS, pH 7.4;

Incubation conditions: 37° C., 5% $CO_2$.

After the incubation, the sample solutions in the dosing wells and the receiving wells were immediately mixed with the cold acetonitrile solution containing the internal standard. The concentration of the tested compounds in all samples (including the initial dosing solution, the supernatant of the dosing wells, and the receiving solution) was analyzed by the LC/MS/MS method. The apparent permeability coefficient, the efflux ratio of and other parameters were calculated.

Experimental Results:

See Table 2. The permeability coefficients through the Caco-2 monolayer cells for the compounds of the present invention, and the reference compounds Palbociclib and LY2835219 were listed in Table 2.

Experimental Conclusion:

Compared to the reference compounds Palbociclib and LY2835219, the compounds of the present invention have high permeability and are less likely to be affected by efflux transporters in vivo. The better permeability allows the compounds of the present invention to be more wildly distributed in the tissues in vivo, such as the lung, resulting in improved anti-tumor efficacy in vivo. Meanwhile, the better permeability makes it possible for the compounds of the present invention to penetrate the blood-brain barrier and achieve the purpose of treating brain metastasis in lung cancer.

TABLE 2

| Test compound | Average permeability coefficient ($10^{-6}$ cm/s) | | Efflux ratio | Category | |
|---|---|---|---|---|---|
| | A→B | B→A | | Permeability | Efflux transporter substrate |
| Palbociclib | 0.85 | 16.46 | 19.39 | Low | Highly possible |
| LY2835219 | 2.69 | 6.34 | 2.36 | Medium | Possible |
| Example 3 | 10.91 | 12.44 | 1.14 | High | Less possible |
| Example 34 | 1.15 | 16.0 | 14.0 | Low | Highly possible |

Experimental Example 4: Solubility Test (1) Kinetic Solubility Test

Experimental Objective:

The kinetic solubility of the compounds was determined under the analytical conditions for routine biological screening.

Testing Principle:

The kinetic solubility is related to the pH, and the pH of the test solution is usually set at 7.4. This test was carried out by shake-flask method and detected by HPLC. Each compound was formulated into a 10 mM stock solution in DMSO and diluted to a theoretical concentration of 200 µM (containing 2% DMSO) in phosphate buffer solution. The mixture was shaken at room temperature for 24 hours, followed by suction-filtration. The supernatant was collected and analyzed by HPLC-UV.

Experimental Procedures:

The Kinetic Solubility Test Solution

Buffer solution (pH 7.4)

50 mM phosphate buffer solution, pH 7.4.

Preparation of Standard Solutions:

50% acetonitrile solution and 50% buffer solution were mixed to give a diluent.

10 mM (10 µL/compound) stock solution was added to 490 µL of the diluent and mixed into a 200 µM standard test solution.

200 µM standard UV test solution was diluted 10 or 200 folds to give a 20 µM or 1 µM standard UV solution.

The standard UV solutions of 1, 20 and 200 µM were used as standard solutions for the kinetic solubility test.

Method:

Sample Preparation, Shaking and Filtration

The compound was dissolved in DMSO and formulated into a 10 mM stock solution. The amount of stock solution is at least 100 µL. Amiodarone hydrochloride, carbamazepine and chloramphenicol were used as the QC for the solubility test.

490 µL of the dissolution medium (buffer solution) was accurately weighed into a 2 mL 96-well plate.

10 µL of the tested compound and the QC stock solution were added to the dissolution medium (buffer solution). Corresponding to the kinetic solubility solution at pH 7.4, the theoretical maximum concentration of the assay compound was 200 µM, containing 2% DMSO. The cap was covered. The theoretical maximum concentration of the tested compound is 200 µM. If a higher theoretical maximum concentration is required, the concentration of the stock solution could be increased.

It was shaken on a shaker at 600 RPM for 24 hours at room temperature.

The samples were transferred to a 96-well filter plate, followed by suction-filtration.

The concentration of the filtrate of the compound was determined by HPLC-UV.

QC Samples:

| Compound | Molecular formula | Kinetic solubility pH 7.4 (µM) |
|---|---|---|
| Amiodarone hydrochloride | $C_{25}H_{29}I_2NO_3$ HCl | <2.00 |
| Carbamazepine | $C_{15}H_{12}N_2O$ | 180 ± 15 |
| Chloramphenicol | $C_{11}H_{12}Cl_2N_2O_5$ | 190 ± 10 |

Data Analysis:

Three standard UV solution from a low concentration to a high concentration were injected to HPLC, followed by the injection of the filtrate of the tested compound as the tested sample. Two needles of the tested sample were inserted in parallel. The UV peaks were integrated. The standard curve was simulated and the kinetic solubility of the sample was calculated.

Experimental Results:

See Table 3-1. The kinetic solubility data for the compounds of the present invention and the reference compound Palbociclib was listed in Table 3-1.

Experimental Conclusion:

The compounds of the present invention have a higher kinetic solubility than the reference compound Palbociclib.

TABLE 3-1

| Tested compound | Kinetic solubility (pH = 7.4, μM) |
|---|---|
| Palbociclib | 103 |
| Example 3 | 171 |
| Example 34 | 194 |

(2) Thermodynamic Solubility Test

Experimental Objective:

The thermodynamic solubility of the compound can be accurately and reliably determined by filtration and HPLC methods.

Testing Principle:

The thermodynamic solubility of the compounds was determined by the shake-flask method and HPLC. The solubility of the compounds is an important property that affects drug screening of compounds and the absorption of compounds in animals and humans. A saturated solution of the compound was first given and quantitatively tested by HPLC to obtain the solubility of the compound.

Experimental Procedures:

The Thermodynamic Solubility Solution

Buffer solution (pH 7.4)

50 mM phosphate buffer solution, pH 7.4.

Preparation of Standard Solutions:

50% acetonitrile solution and 50% buffer solution were mixed to give a diluent.

10 mM (10 μL/compound) stock solution was added to the diluent (490 μL/compound) and mixed into a 200 μM standard UV test solution.

200 μM standard UV test solution was diluted 10 or 200 folds to give a 20 μM or 2 μM standard UV solution.

The standard UV solutions of 2, 20 and 200 μM were used as standard solutions for the kinetic solubility test.

Method:

Sample Preparation, Shaking and Filtration

Not less than 2 mg of the sample powder was weighed into a vial of Whatman miniuniprep. If test of the thermodynamic solubility of a sample in multiple buffer solutions is required, an individual vial is required for each test.

450 μL of the buffer solution (pH 7.4) was added to each Whatman miniuniprep vial.

After the addition of the buffer solution, the Whatman miniuniprep cap with a filter was mounted and pressed above the liquid level so that the filter could contact with the buffer solution during shaking.

The solubility sample was vortexed for 2 minutes. And the observation of the solution was recorded.

It was shaken at 550 RPM for 24 hours at room temperature (about 22 to 25° C.).

The Whatman Miniunipreps filter cap was pressed to the bottom to give the filtrate of the sample solubility solution. All sample vials should be filtered before and after insoluble substances and their leakage.

The buffer was diluted 50 folds to give a sample diluent.

Three UV standards from low to high concentration were injected into HPLC, followed by the injection of the dilutions and supernatants of the tested compounds. The tested sample was injected twice.

The UV peaks were integrated. The standard curve was simulated and the thermodynamic solubility of the sample was calculated.

QC Samples:

| Compound | Molecular formula | Thermodynamic solubility pH 7.4 (μM) |
|---|---|---|
| Amiodarone hydrochloride | $C_{25}H_{29}I_2NO_3$ HCl | <2.00 |
| Carbamazepine | $C_{15}H_{12}N_2O$ | 450 ± 60 |
| Chloramphenicol | $C_{11}H_{12}Cl_2N_2O_5$ | 11000 ± 1000 |

Experimental Results:

See Table 3-2. The thermodynamic solubility data for the compound of the present invention and the reference compound Palbociclib was listed in Table 3-2.

Experimental Conclusion:

The compounds of the present invention have a higher thermodynamic solubility than the reference compound Palbociclib.

TABLE 3-2

| Tested compound | Thermodynamic solubility (pH = 7.4, μM) |
|---|---|
| Palbociclib | 65.3 |
| Example 34 | 6420 |

Experimental Example 5: Metabolic Stability Assay of Rats, Mice and Human Liver Microsomes Experimental Objective:

This assay is used to test the metabolic stability of tested substances in rats, mice and human liver microsomes.

Experimental Procedures:

1) The tested compound with concentration of 1 μM was co-incubated with liver microsomes with a protein concentration of 0.5 mg/mL under a reducing coenzyme II regeneration system in a 37° C. water bath.

2) The positive controls include: testosterone (3A4 substrate), propafenene (2D6 substrate) and diclofenac (2C9 substrate). The incubation condition of the positive controls was consistent with that of the compound.

3) The reaction time points were: 0, 5, 10, 20, 30 and 60 minutes, and the reaction is terminated at the corresponding time point using a termination solution containing an internal standard. The compounds were also incubated with microsomes for 60 minutes without a reducing coenzyme II regeneration system and served as a negative control.

4) Each time point was a single point (n=1).

5) The sample was determined by LC/MS/MS, and the compound concentration was shown as the ratio of the peak area of the compound to the peak area of the internal standard (non-standard).

6) In the project report summary, the half-life and the clearance rate would be calculated.

7) The following formulas were used to calculate the clearance rate:

$$C_t = \frac{1}{2}C_0, t_{1/2} = \frac{\ln 2}{k} = \frac{0.693}{k}.$$

-continued $$CL_{int}^{mic} = \frac{0.693}{\text{In vitro } T_{1/2}} \cdot \frac{1}{\text{mg/ml microsomal protein in incubation}}$$

Note:

a) microsomal protein in incubation:

Weight ratio of the liver to the body: the parameters of rats, mice and human were 40 g/kg, 88 g/kg and 20 g/kg, respectively.

The clearance rate throughout the liver was calculated by $CL_{int}^{mic}$:

$$CL_{int(liver)} = CL \cdot \frac{45 \text{ mg} \cdot \text{microsomes}}{\text{g} \cdot \text{liver}} \cdot \frac{\text{g} \cdot \text{liver}}{\text{kg} \cdot \text{body} \cdot \text{weight}}$$

Note:

a) microsomes: the microsomes;
b) liver: the liver;
c) body weight: the body weight;

Experimental Results:

The experimental results were shown in Table 4.

Experimental Conclusion:

The compounds of the present invention have a significantly improved stability of liver microsomes in human, rats and mice than that of the reference compounds LY2835219 and Palbociclib.

TABLE 4

| Tested compound | Human/Rats/Mice $T_{1/2}$ (min) |
| --- | --- |
| Palbociclib | 44.7/47.8/53.3 |
| LY2835219 | 2.69/6.34/2.36 |
| Example 34 | 43.1/>145/40.2 |

Experimental Example 6: In Vivo Pharmacodynamic Study (1)

The in vivo pharmacodynamic experiments were performed on the BALB/c nude mice implanted subcutaneously with the LU-01-0393 lung cancer patient-derived tumor tissue xenograft (PDX).

Experimental Procedures:

BALB/c nude mice, female, 6-8 weeks, weighing approximately 17-21 g, were placed in a single ventilated cage (5 mice per cage) under a special pathogen free environment. All of the cages, beddings and water were disinfected before use. All of the animals were permitted free access to a standard certified commercial laboratory diet. A total of 36 mice purchased from Vital River Laboratory Animal Co., LTD, Beijing were used for the study. Each mouse was implanted subcutaneously with a tumor LU-01-0393 FP4 section (20-30 mm³) in the right back for tumor growth. The dosing initiated when the average tumor volume reached about 150-200 mm³. The tested compound was orally administered daily, and the dosage was as shown in Table 2. The tumor volume was measured twice a week using a two-dimensional caliper, and the volume was measured in mm³, calculated by the following the formula: V=0.5 a×b², wherein, a and b were the long and short diameters of the tumor, respectively. The antitumor efficacy was determined by dividing the average increase in the tumor volume of the animals treated with the compound by the average increase in the tumor volume of the untreated animals.

Experimental Results: See Table 5.

Experimental Conclusion:

The compounds of the present invention exhibit significant antitumor activity on the LU-01-0393 lung cancer patient-derived tumor tissue xenograft (PDX) model. As shown in Table 5, after 20 days from the beginning of the experiment, the tumor volume of the untreated animal group rapidly increased from the initial 144 mm³ to 437 mm³, while the tumor volume of the animal group of Example 1 was slowly increased from 144 mm³ to 212 mm³, and the increase rate is similar to that of the reference compound Palbociclib. However, the dosage of Example 1 (60 mg/kg) was only half of the reference compound Palbociclib (120 mg/kg). It was indicated that the antitumor activity of the compounds of the present invention is superior to that of the reference compounds.

TABLE 5

| Tested compound | Dosage (mg/kg) | Gross tumor volume (mm³) | | | |
| --- | --- | --- | --- | --- | --- |
| | | Day 0 | Day 7 | Day 14 | Day 20 |
| Blank control | 0 | 144 | 214 | 325 | 437 |
| Palbociclib | 120 | 145 | 173 | 179 | 188 |
| Example 1 | 60 | 144 | 132 | 182 | 212 |

Experimental Example 7: In Vivo Pharmacodynamic Study (2)

The in vivo pharmacodynamic experiments were performed on the BALB/c nude mice implanted subcutaneously with the non-small cell lung cancer NCI-H358 model.

Experimental Procedures:

The animal information of the experiments in Example 3 was as follows: BALB/c nude mice, female, 6-8 weeks, weighing approximately 17-20 g, were placed in a single ventilated cage (3-5 mice per cage) under a special pathogen free environment. All of the cages, beddings and water were disinfected before use. All of the animals were permitted free access to a standard certified commercial laboratory diet. A total of 86 mice purchased from Vital River Laboratory Animal Co., LTD, Beijing were used for the study. The animal information of the experiments in Example 34 was as follows: BALB/c nude mice, female, 6-8 weeks, weighing approximately 16-18 g, were placed in a single ventilated cage (4 mice per cage) under a special pathogen free environment. All of the cages, beddings and water were disinfected before use. All of the animals were permitted free access to a standard certified commercial laboratory diet. A total of 56 mice purchased from Shanghai Lingchang Biotechnology Co., Ltd. were used for the study.

Each mouse was implanted subcutaneously with NCI-H358 tumor cells in the right back for tumor growth. The dosing initiated when the average tumor volume reached about 100-200 mm³. The tested compound was orally administered daily, and the dosages of Example 3 and Example 34 were as shown in Table 6-1 and Table 6-2, respectively. The tumor volume was measured twice a week using a two-dimensional caliper, and the volume was measured in mm³, calculated by the following formula: V=0.5 a×b², wherein, a and b were the long and short diameters of the tumor, respectively. The antitumor efficacy was determined by dividing the average increase in the tumor volume of the animals treated with the compound by the average increase in the tumor volume of the untreated animals, and the safety of the compound was determined by the change in the body weight of the animal treated with the compound.

Experimental Results: See Table 6-1 and Table 6-2.

Experimental Conclusion:

The compounds of the present invention exhibit significant antitumor activity on the non-small cell lung cancer NCI-H358 model and better safety. Furthermore, in this model, the antitumor effect of the compounds of the invention has a dose-dependent tendency.

TABLE 6-1

| Indicating factors | Day of administration | Blank control (0 mg/kg) | Palbociclib (60 mg/kg) | LY2835219 (60 mg/kg) | Example 3 (60 mg/kg) |
|---|---|---|---|---|---|
| Gross tumor volume ($mm^3$) | 0 day | 152 | 152 | 152 | 152 |
| | 7 days | 265 | 137 | 97 | 141 |
| | 14 days | 315 | 107 | 73 | 159 |
| | 17 days | 335 | 104 | 60 | 136 |
| Changes in animal weight (%) | 0 days | 0.0 | 0.0 | 0.0 | 0.0 |
| | 7 days | 2.1 | 1.0 | −2.9 | −1.0 |
| | 14 days | 2.6 | 0.9 | −3.5 | 0.5 |
| | 17 days | 2.6 | 0.7 | −3.5 | 0.8 |

TABLE 6-2

| Group | Dosage | Gross tumor volume ($mm^3$) (Day 1) | Gross tumor volume ($mm^3$) (Day 28) | TGI (%) (Day 28) |
|---|---|---|---|---|
| Blank control | — | 135 ± 14 | 1,070 ± 101 | — |
| Example 34 | 20 mg/kg | 149 ± 18 | 940 ± 70 | 15.3 |
| | 60 mg/kg | 169 ± 27 | 804 ± 103 | 32.1 |
| | 150 mg/kg | 149 ± 18 | 215 ± 34 | 92.9 |

TGI: Tumor Growth Inhibition. TGI (%)=[(1-(mean tumor volume at the end of administration of a treatment group−mean tumor volume at the beginning of administration of the treatment group))/(mean tumor volume at the end of treatment of the solvent control group−mean tumor volume at the beginning of treatment of the solvent control group started)]×100%

Experimental Example 8: In Vivo Pharmacodynamic Study (3)

The in vivo pharmacodynamic experiments were performed on the BALB/c nude mice implanted subcutaneously with the colorectal cancer HCT-116 model.

Experimental Procedures:

BALB/c nude mice, female, 6-8 weeks, weighing approximately 18-22 g, were placed in a single ventilated cage (3-5 mice per cage) under a special pathogen free environment. All of the cages, beddings and water were disinfected before use. All of the animals were permitted free access to a standard certified commercial laboratory diet. A total of 48 mice purchased from Shanghai Lingchang Biotechnology Co., Ltd. were used for the study. Each mouse was implanted subcutaneously with 0.2 mL of 5×106 HCT-116 cells in the right back for tumor growth. The dosing in groups initiated when the average tumor volume reached about 132 $mm^3$. The tested compound was orally administered daily, and the dosage was as shown in Table 5. The tumor volume was measured twice a week using a two-dimensional caliper, and the volume was measured in $mm^3$, calculated by the following the formula: V=0.5 a×$b^2$, wherein, a and b were the long and short diameters of the tumor, respectively. The antitumor efficacy was determined by dividing the average increase in the tumor volume of the animals treated with the compound by the average increase in the tumor volume of the untreated animals.

Experimental Results: See Table 7.

Experimental Conclusion:

The compounds of the present invention exhibit better antitumor activity and higher safety on the colorectal cancer HCT-116 model.

TABLE 7

| Indicating factors | Day of administration | Blank control (0 mg/kg) | Example 34 (60 mg/kg(D0-D11), 120 mg/kg (D12-D20), PO, QD × 21) |
|---|---|---|---|
| Gross tumor volume ($mm^3$) | 0 day | 132 | 132 |
| | 7 days | 548 | 416 |
| | 14 days | 1208 | 695 |
| | 21 days | 2077 | 963 |
| Changes in animal weight (%) | 0 day | 0 | 0 |
| | 7 days | 4.1 | 2.5 |
| | 14 days | 3.2 | −2.3 |
| | 21 days | 2.0 | −5.9 |

What is claimed is:

1. A compound of formula (I):

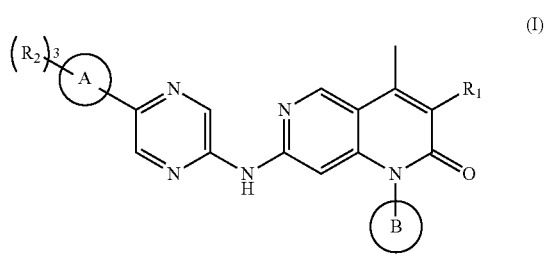

or a pharmaceutically acceptable salt, stereoisomer or tautomer thereof, wherein:

ring A is a 4-11 membered heterocycloalkyl;

ring B is $C_{3-6}$ cycloalkyl, 3-6 membered heterocycloalkyl, phenyl or 5-6 membered heteroaryl, each optionally substituted by 1, 2 or 3 R;

$R_1$ is H, $C_{1-3}$ alkyl, $C_{1-3}$ heteroalkyl or C(=NOH)H, wherein the $C_{1-3}$ alkyl, $C_{1-3}$ heteroalkyl and —C(=NOH)H are each optionally substituted by 1, 2 or 3 R;

each $R_2$ is independently H, halogen, CN, $C_{1-5}$ alkyl, $C_{1-5}$ heteroalkyl, OH, $C_{3-6}$ cycloalkyl or 3-6 membered heterocycloalkyl, wherein the $C_{1-5}$ alkyl, $C_{1-5}$ heteroalkyl, $C_{3-6}$ cycloalkyl and 3-6 membered heterocycloalkyl are each optionally substituted by 1, 2 or 3 R;

each R is independently halogen, CN, $C_{1-3}$ alkyl, $C_{1-3}$ heteroalkyl, $NH_2$, $NO_2$ or OH, wherein the $C_{1-3}$ alkyl and $C_{1-3}$ heteroalkyl are each optionally substituted by 1, 2 or 3 R'; and each R' is independently F, Cl, Br, I, CN, $NH_2$ or OH;

wherein each hetero in the $C_{1-3}$ heteroalkyl, $C_{1-5}$ heteroalkyl, 3-6 membered heterocycloalkyl, 4-11 membered heterocycloalkyl and 5-6 membered heteroaryl is 1, 2 or 3 heteroatom(s) or heteroatomic group(s) independently selected from the group consisting of —C(=O)—, N, —NH—, O—, —S—, —S(=O)— and —S(=O)$_2$.

2. The compound according to claim 1, or a pharmaceutically acceptable salt, stereoisomer or tautomer thereof, wherein ring A is 5-9 membered heterocycloalkyl.

3. The compound according to claim 2, or a pharmaceutically acceptable salt, stereoisomer or tautomer thereof, wherein

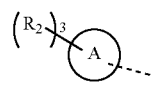

is:

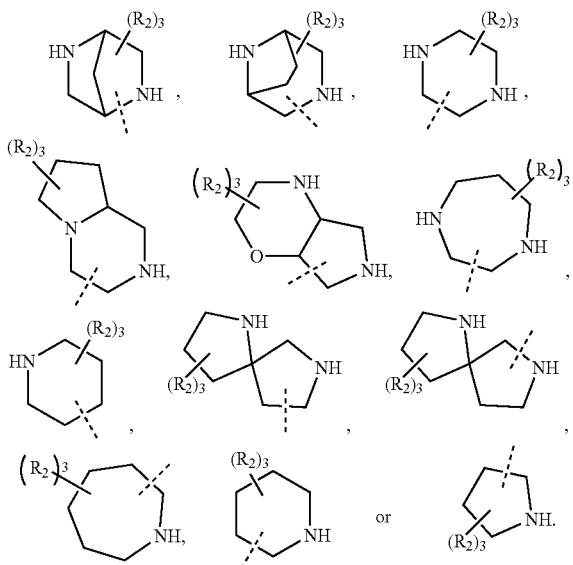

4. The compound according to claim 3, or a pharmaceutically acceptable salt, stereoisomer or tautomer thereof, wherein

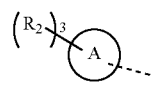

is

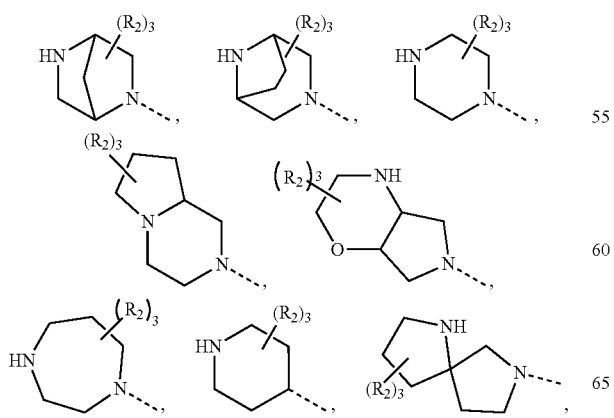

-continued

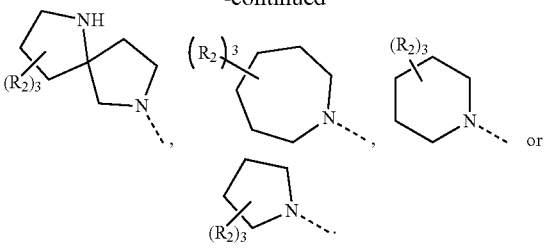

5. The compound according to claim 3, or a pharmaceutically acceptable salt, stereoisomer or tautomer thereof, wherein

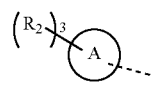

is

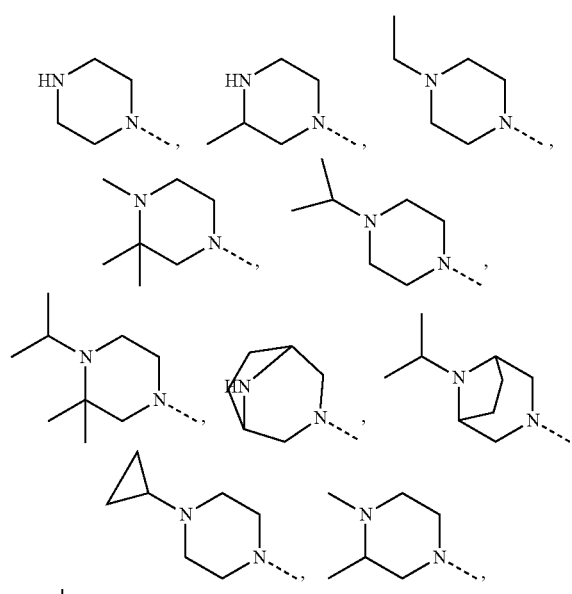

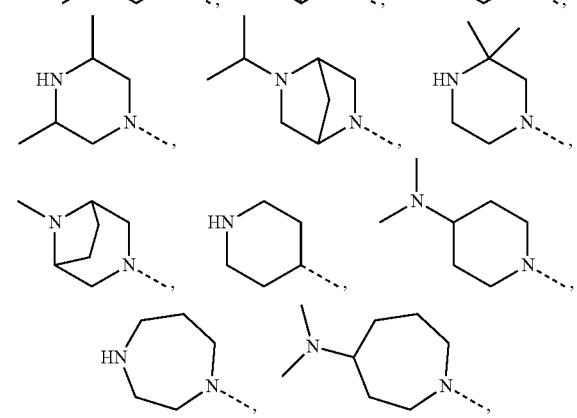

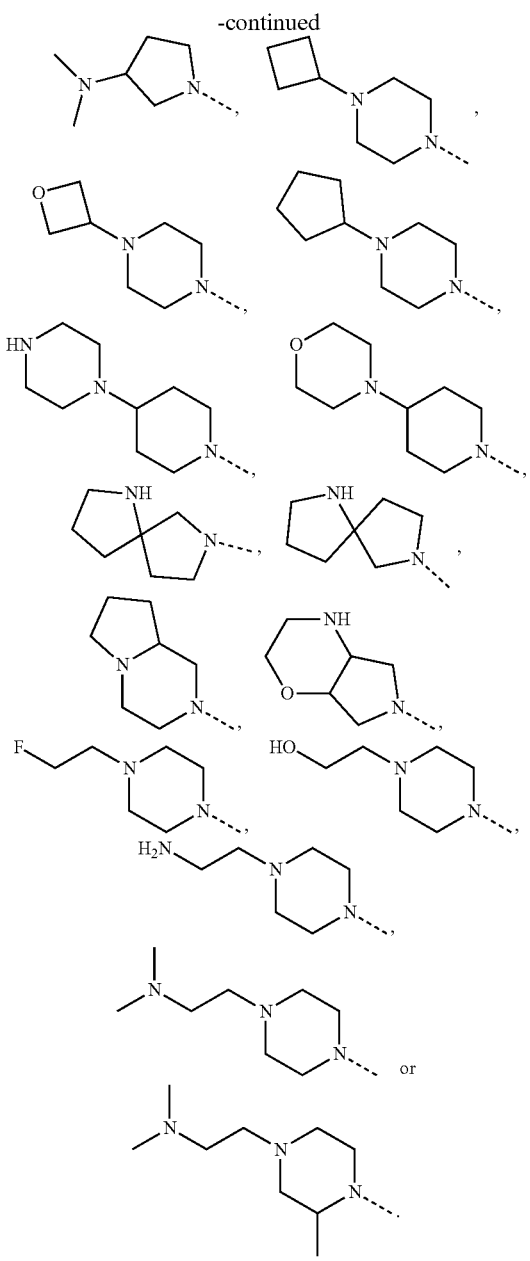

6. The compound according to claim 1, or a pharmaceutically acceptable salt, stereoisomer or tautomer thereof, wherein ring B is cyclobutyl, cyclopentyl, cyclohexyl or phenyl, each optionally substituted by 1, 2 or 3 R.

7. The compound according to claim 6, or a pharmaceutically acceptable salt, stereoisomer or tautomer thereof, wherein ring B is cyclopentyl, cyclohexyl or phenyl.

8. The compound according to claim 1, or a pharmaceutically acceptable salt, stereoisomer or tautomer thereof, wherein each R is independently F, Cl, Br, CN, $CH_3$, $CH_2CH_3$, $CH_2F$, $CHF_2$, $CF_3$, $NH_2$, OH or $OCH_3$.

9. The compound according to claim 1, or a pharmaceutically acceptable salt, stereoisomer or tautomer thereof, wherein $R_1$ is H, $CH_3$, $CH_2CH_3$, —C(=O)$CH_3$ or —C(=NOH)H, wherein the $CH_3$, $CH_2CH_3$, —C(=O)$CH_3$ and —C(=NOH)H are each optionally substituted by 1, 2 or 3 R.

10. The compound according to claim 9, or a pharmaceutically acceptable salt, stereoisomer or tautomer thereof, wherein $R_1$ is $CH_3$, $CHF_2$, —C(=O)$CH_3$, —C(=NOCH$_2$CH$_3$)CH$_3$ or —C(=NOCH(CH$_3$))CH$_3$.

11. The compound according to claim 1, or a pharmaceutically acceptable salt, stereoisomer or tautomer thereof, wherein each $R_2$ is independently H, F, Cl, CN, $CH_3$, $CH_2CH_3$, $(CH_2)_2CH_3$, $CH(CH_3)_2$, $(CH_2)_2N(CH_3)_2$, $N(CH_3)_2$, OH, cyclopropyl, cyclobutyl, cyclopentyl, oxetanyl, piperazinyl or morpholinyl, wherein the $CH_3$, $CH_2CH_3$, $(CH_2)_2CH_3$, $CH(CH_3)_2$, $(CH_2)_2N(CH_3)_2$, $N(CH_3)_2$, cyclopropyl, cyclobutyl, cyclopentyl, oxetanyl, piperazinyl or morpholinyl are each optionally substituted by 1, 2 or 3 R.

12. The compound according to claim 11, or a pharmaceutically acceptable salt, stereoisomer or tautomer thereof, wherein each $R_2$ is independently H, $CH_3$, $CH_2CH_3$, $(CH_2)_2CH_3$, $CH(CH_3)_2$, $(CH_2)_2N(CH_3)_2$, $N(CH_3)_2$, cyclopropyl, cyclobutyl, cyclopentyl, oxetan-3-yl, piperazin-1-yl or morpholin-4-yl, wherein the $CH_3$, $CH_2CH_3$, $(CH_2)_2CH_3$, $CH(CH_3)_2$, $(CH_2)_2N(CH_3)_2$, $N(CH_3)_2$, cyclopropyl, cyclobutyl, cyclopentyl, oxetan-3-yl, piperazin-1-yl and morpholin-4-yl are each optionally substituted by 1, 2 or 3 R.

13. The compound according to claim 12, or a pharmaceutically acceptable salt, stereoisomer or tautomer thereof, wherein each $R_2$ is independently H, $CH_3$, $CH_2CH_3$, $(CH_2)_2CH_3$, $CH(CH_3)_2$, $(CH_2)_2F$, $(CH_2)_2NH_2$, $(CH_2)_2N(CH_3)_2$, $(CH_2)_{20}H$, $N(CH_3)_2$, cyclopropyl, cyclobutyl, cyclopentyl, oxetan-3-yl, piperazin-1-yl or morpholin-4-yl.

14. The compound according to claim 1, wherein the compound is formula (II), formula (III), formula (IV), formula (V), formula (VI) or formula (VI'):

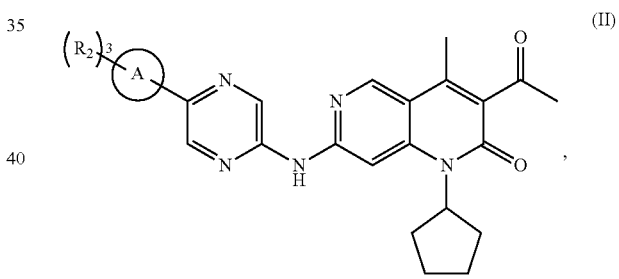

(II)

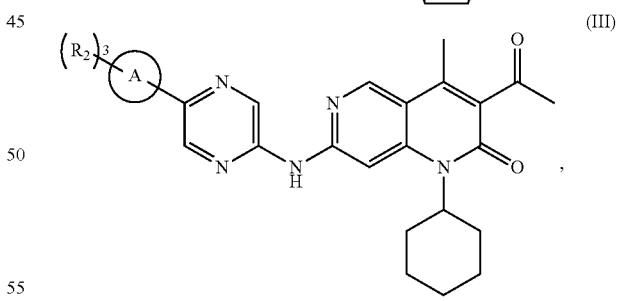

(III)

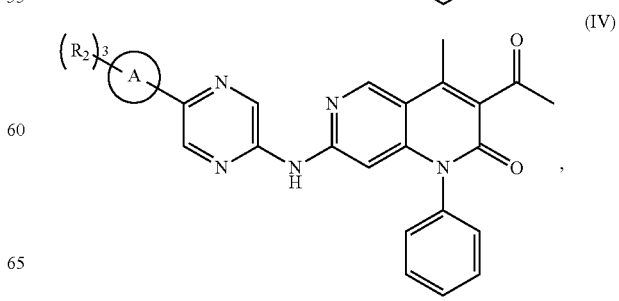

(IV)

-continued

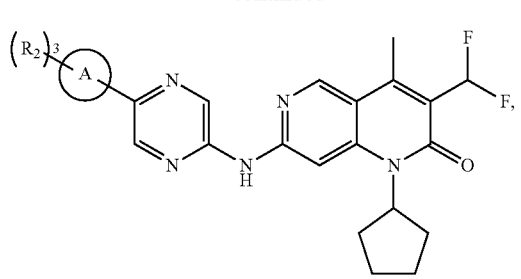 (V)

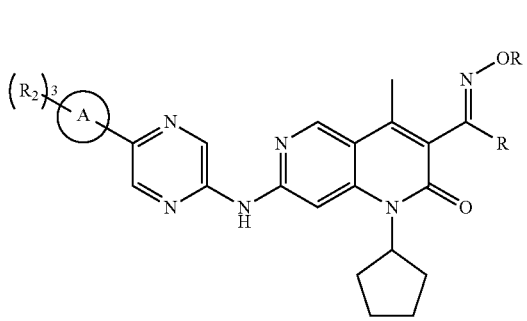 (VI)

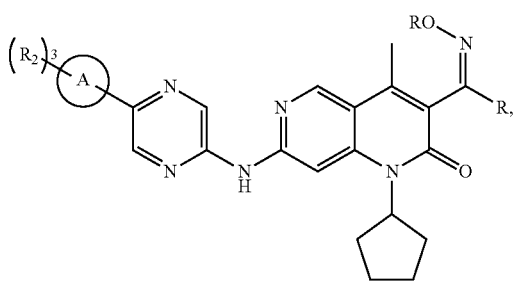 (VI')

or a pharmaceutically acceptable salt, stereoisomer or tautomer thereof.

15. The compound of according to claim 1, wherein the compound is formula (VII):

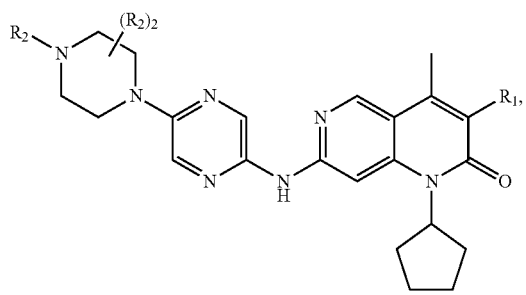 (VII)

or a pharmaceutically acceptable salt, stereoisomer or tautomer thereof.

16. The compound according to claim 1, wherein the compound is formula (VIII):

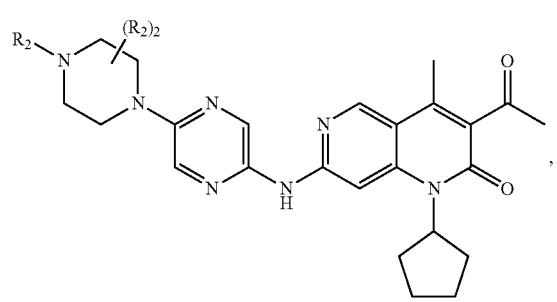 (VIII)

or a pharmaceutically acceptable salt, stereoisomer or tautomer thereof.

17. A pharmaceutical composition comprising a therapeutically effective amount of the compound according to claim 1, or a pharmaceutically acceptable salt, stereoisomer or tautomer thereof, and a pharmaceutically acceptable carrier.

18. A method for inhibiting cyclin-dependent kinase 4 activity and/or cyclin-dependent kinase 6 activity in a subject having cancer, comprising:

administering to the subject in need thereof a therapeutically effective amount of the compound according to claim 1, or a pharmaceutically acceptable salt, stereoisomer or tautomer thereof.

19. A compound selected from the group consisting of:

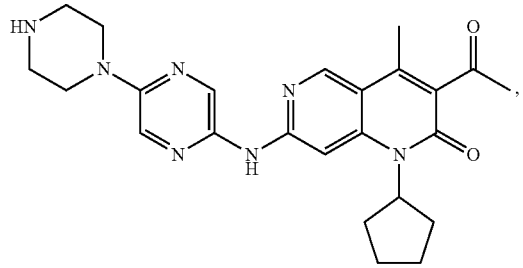

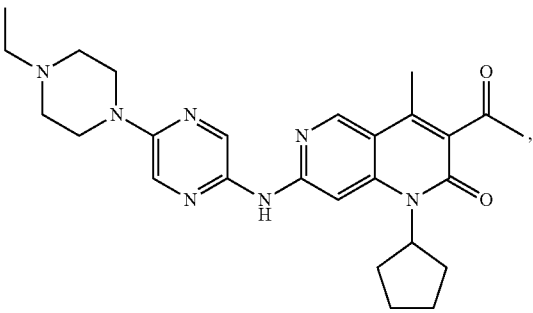

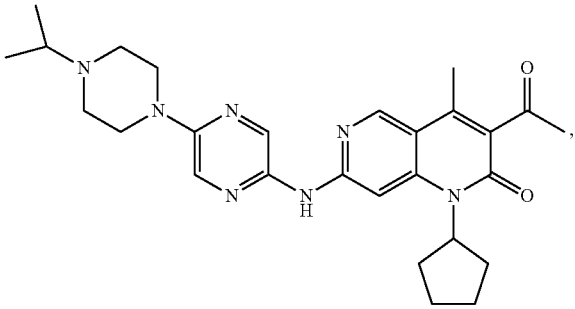

93
-continued
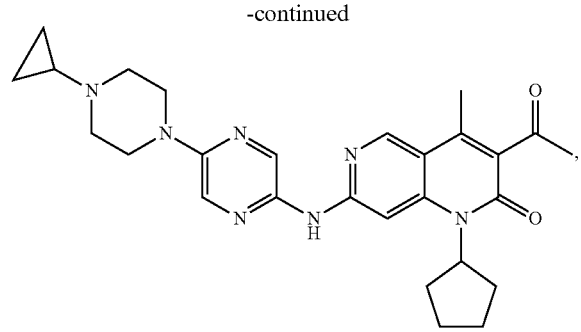
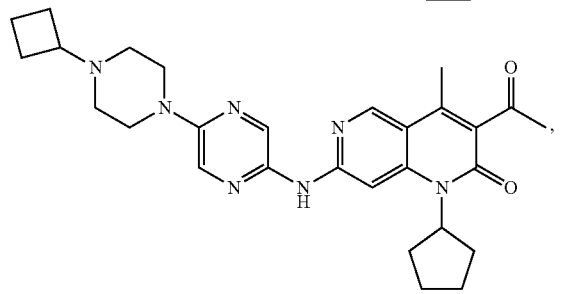
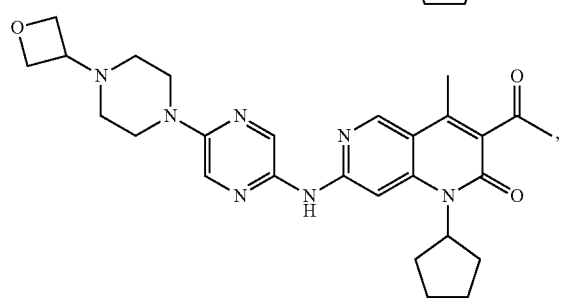
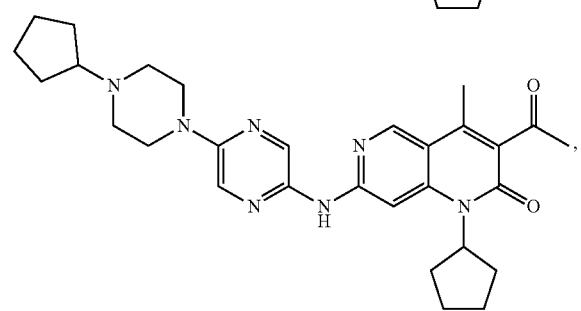
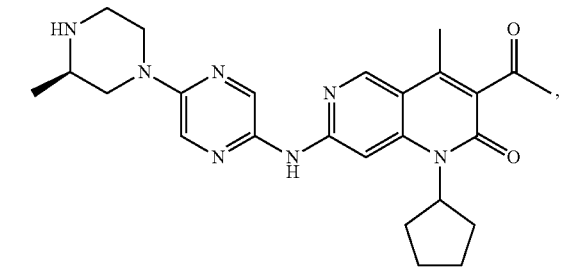
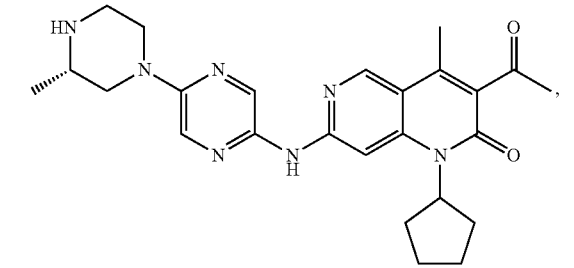
94
-continued
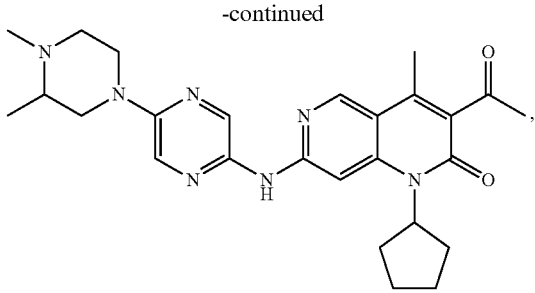
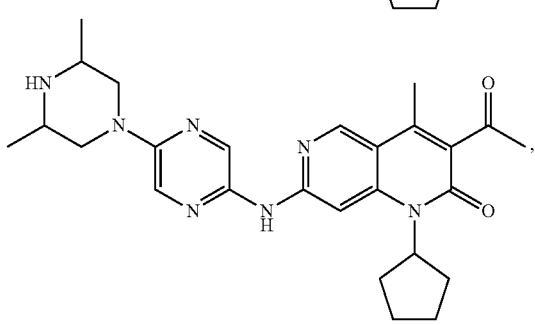
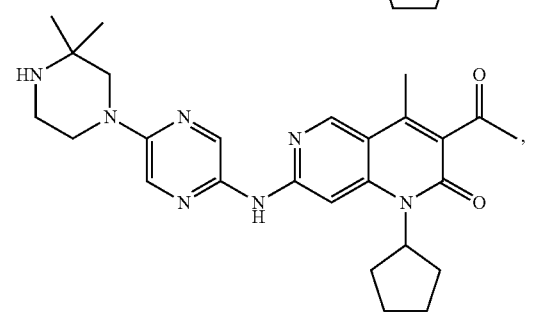
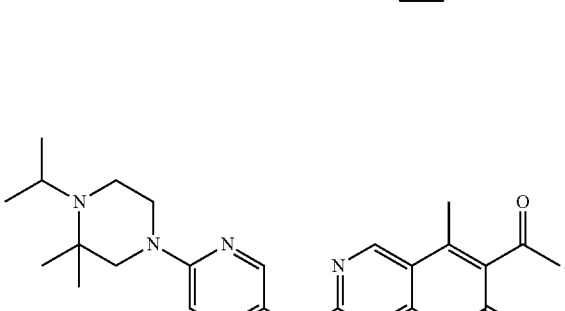
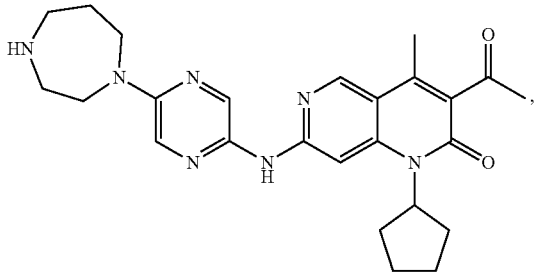

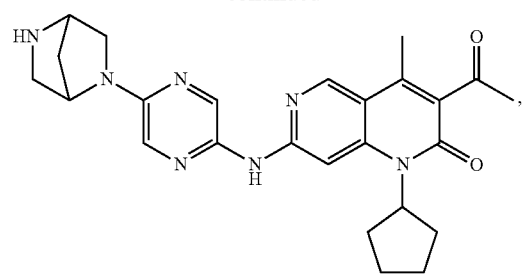
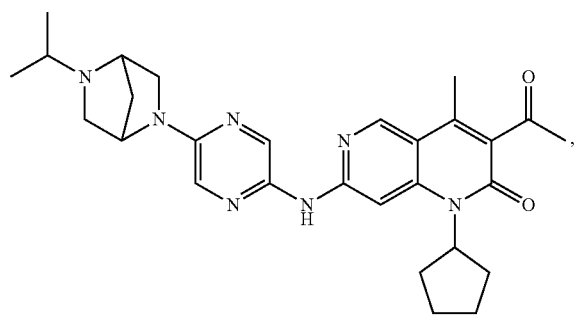
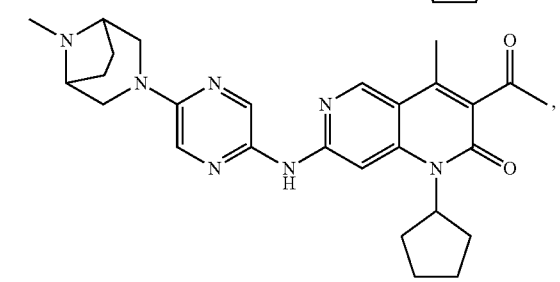
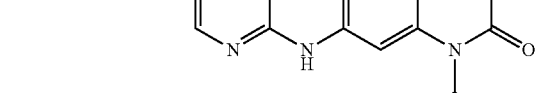
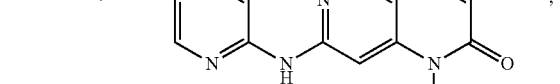
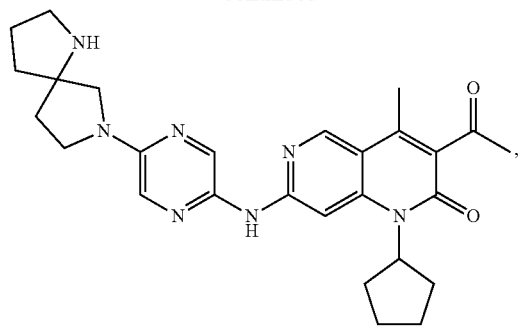
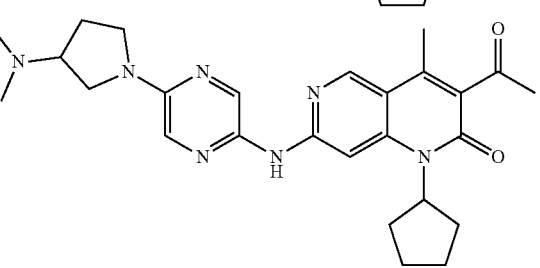
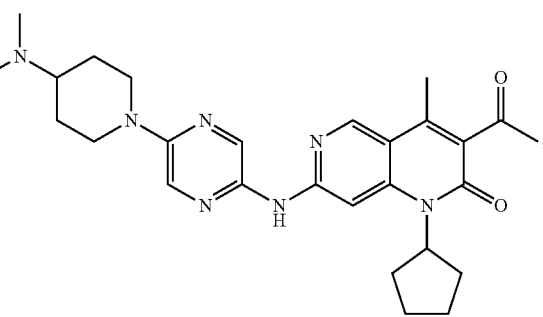
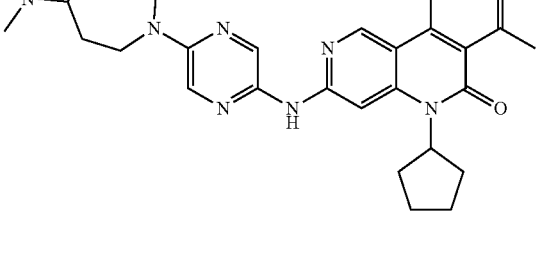
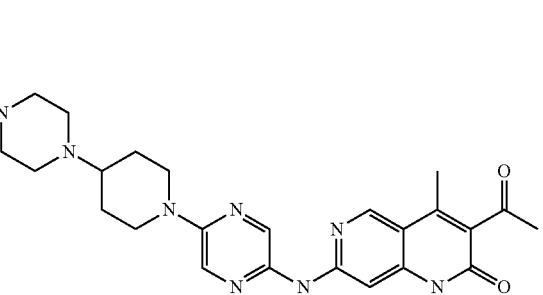

97
-continued
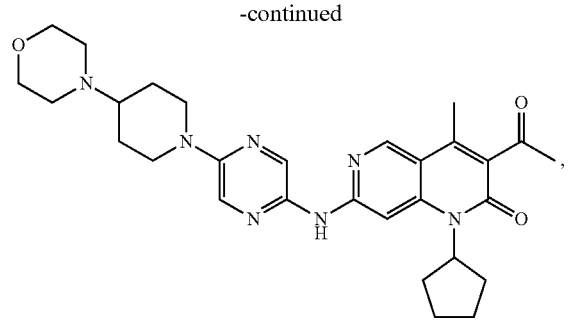
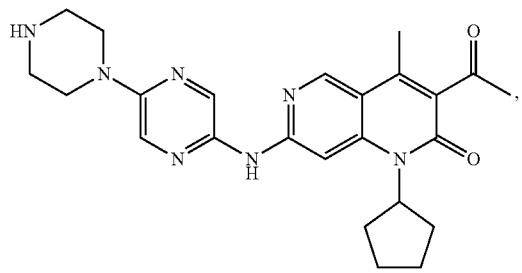
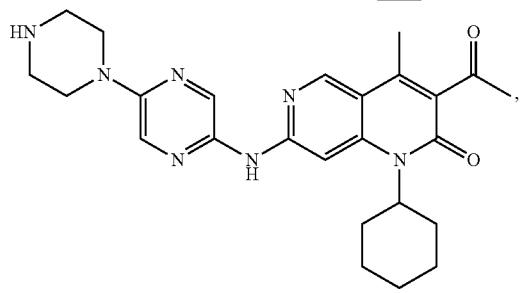
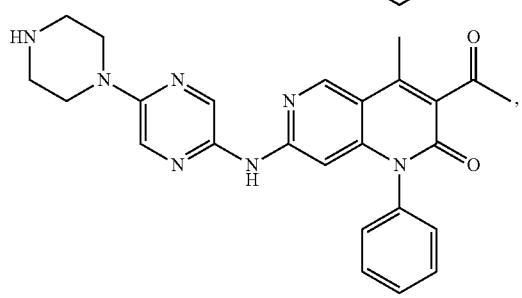
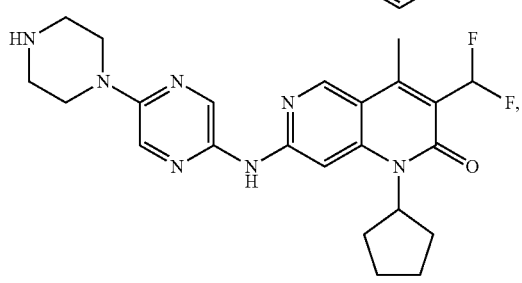
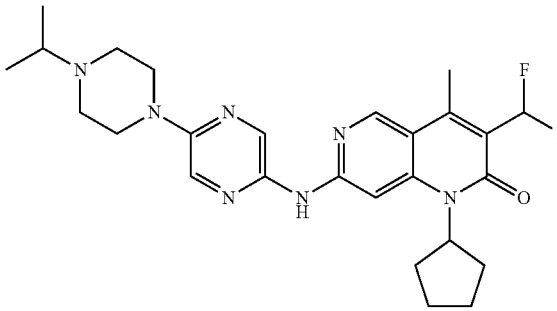
98
-continued
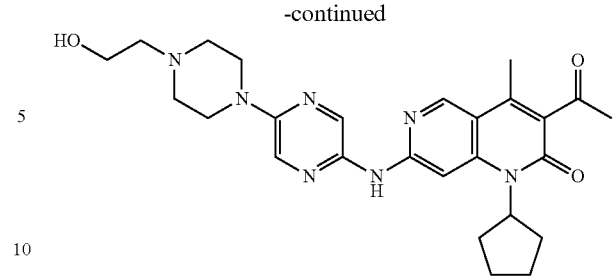
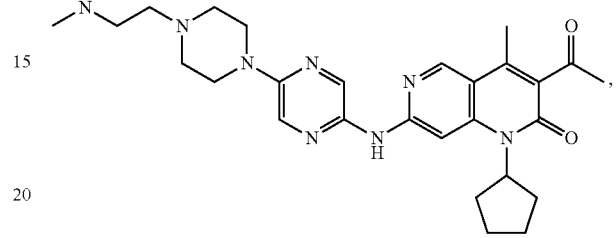
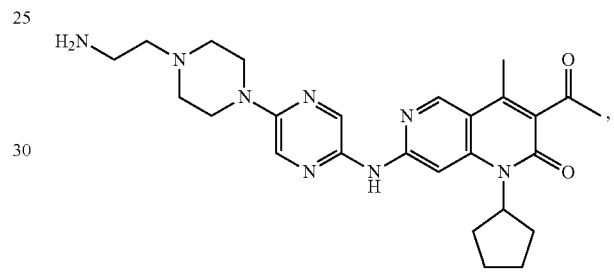
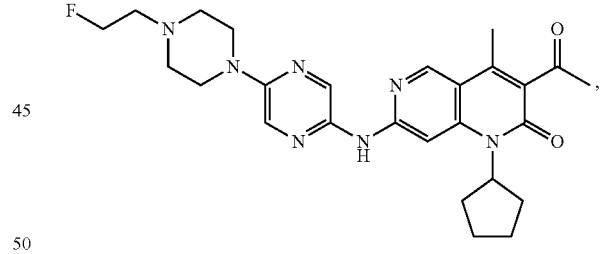
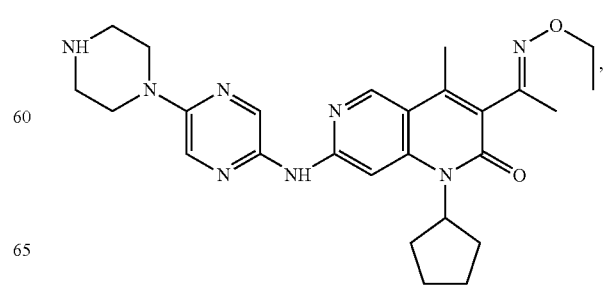

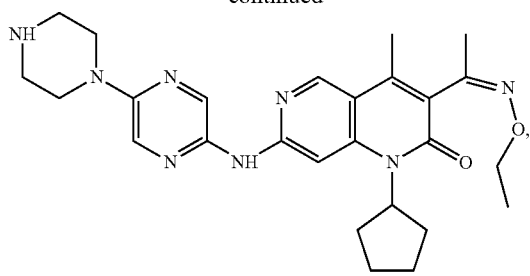

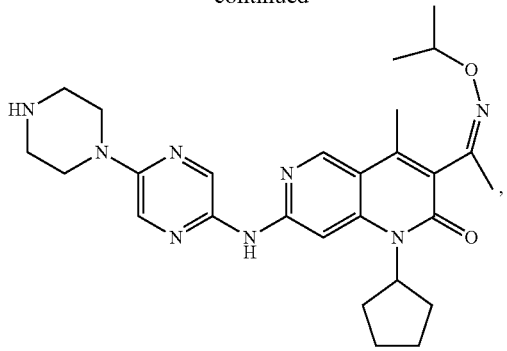

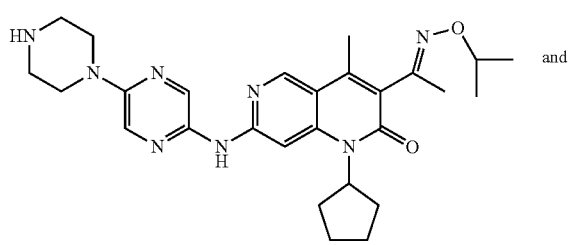
and or a pharmaceutically acceptable salt, stereoisomer or tautomer thereof.

20. A method for inhibiting cyclin-dependent kinase 4 activity and/or cyclin-dependent kinase 6 activity in a subject having cancer, comprising:
administering to the subject in need thereof a therapeutically effective amount of the compound according to claim 19, or a pharmaceutically acceptable salt, stereoisomer or tautomer thereof.

* * * * *